(12) United States Patent
Orbe Lopategui et al.

(10) Patent No.: US 9,440,989 B2
(45) Date of Patent: Sep. 13, 2016

(54) ANTIFIBRINOLYTIC COMPOUNDS

(71) Applicant: PROYECTO DE BIOMEDICINA CIMA, S.L., Zizur Mayor (ES)

(72) Inventors: Josune Orbe Lopategui, Pamplona (ES); Julen Oyarzabal Santamarina, Pamplona (ES); José Antonio Páramo Fernández, Pamplona (ES); José Antonio Rodriguez Garcia, Pamplona (ES)

(73) Assignee: PROYECTO DE BIOMEDICINA CIMA, S.L., Zizur Mayor (Navarra) (ES)

(*) Notice: Subject to any disclaimer, the term of this patent is extended or adjusted under 35 U.S.C. 154(b) by 0 days.

(21) Appl. No.: 14/415,474

(22) PCT Filed: Jul. 17, 2013

(86) PCT No.: PCT/EP2013/065071
§ 371 (c)(1),
(2) Date: Jan. 16, 2015

(87) PCT Pub. No.: WO2014/012964
PCT Pub. Date: Jan. 23, 2014

(65) Prior Publication Data
US 2015/0175618 A1  Jun. 25, 2015

(30) Foreign Application Priority Data
Jul. 18, 2012 (EP) .................................. 12382285

(51) Int. Cl.
| | | |
|---|---|---|
| C07D 491/107 | (2006.01) |
| C07D 401/12 | (2006.01) |
| C07D 401/04 | (2006.01) |
| C07D 221/20 | (2006.01) |
| C07C 317/48 | (2006.01) |
| C07D 401/06 | (2006.01) |
| C07D 265/34 | (2006.01) |
| C07D 211/34 | (2006.01) |
| C07C 317/14 | (2006.01) |
| C07D 409/06 | (2006.01) |
| C07D 471/10 | (2006.01) |
| C07D 471/20 | (2006.01) |

(52) U.S. Cl.
CPC ......... *C07D 491/107* (2013.01); *C07C 317/14* (2013.01); *C07C 317/48* (2013.01); *C07D 211/34* (2013.01); *C07D 221/20* (2013.01); *C07D 265/34* (2013.01); *C07D 401/04* (2013.01); *C07D 401/06* (2013.01); *C07D 401/12* (2013.01); *C07D 409/06* (2013.01); *C07D 471/10* (2013.01); *C07D 471/20* (2013.01); *C07C 2101/14* (2013.01); *C07C 2103/94* (2013.01)

(58) Field of Classification Search
CPC ..... C07D 401/04; C07D 401/06; C07D 265/34; C07D 491/107; C07D 221/20; C07D 471/10; C07D 409/06; C07D 401/12
USPC .......................... 546/17, 16; 544/71; 514/278
See application file for complete search history.

(56) References Cited

U.S. PATENT DOCUMENTS

| 3,868,411 A | 2/1975 | Vincent et al. |
|---|---|---|
| 4,483,867 A | 11/1984 | Svahn et al. |

(Continued)

FOREIGN PATENT DOCUMENTS

| WO | WO9837877 | * | 9/1998 |
|---|---|---|---|
| WO | WO9942436 | * | 8/1999 |

OTHER PUBLICATIONS

International Search Report for PCT/EP2013/065071, mailed Sep. 20, 2013, 10 pgs.

(Continued)

*Primary Examiner* — Rita Desai
(74) *Attorney, Agent, or Firm* — Squire Patton Boggs (US) LLP

(57) ABSTRACT

It relates to spirocyclic compounds of formula (I), or pharmaceutically or veterinary acceptable salts thereof, or any stereoisomers either of the compounds of formula (I) or of their pharmaceutically or veterinary acceptable salts, wherein A and B form a spirocyclic ring system wherein the spiro atom connecting A and B is a carbon atom and wherein A is a known 3- to 8-membered carbocyclic or heterocyclic monocyclic ring or a known 6- to 18-membered carbocyclic or heterocyclic polycyclic ring system; B is a known 4- to 7-membered carbocyclic or heterocyclic monocyclic ring; C is phenyl or a known 5- to 6-membered heteroaromatic ring; and $R^1$-$R^7$ are as defined herein. It also relates to a process for their preparation, as well as to the intermediates used in this process; to pharmaceutical or veterinary compositions containing them, and to their use in medicine, in particular as antifibrinolytic and antihemorragic agents.

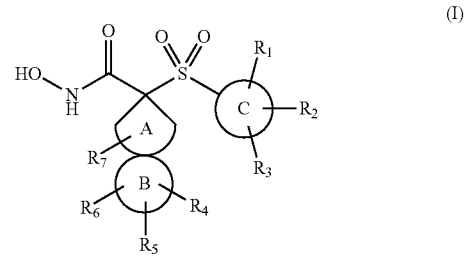

(I)

8 Claims, No Drawings

(56) References Cited

U.S. PATENT DOCUMENTS

| | | |
|---|---|---|
| 6,172,057 B1 * | 1/2001 | Venkatesan .......... A61K 31/165 514/212.01 |
| 6,197,791 B1 * | 3/2001 | Venkatesan .......... A61K 31/165 514/235.5 |
| 2002/0099035 A1 | 7/2002 | Sandanayaka et al. |

OTHER PUBLICATIONS

Bouyssi et al., "Rearrangement of oxaspiroheptanes to cyclohexanones mediated by lithium iodide", Synlett vol. 5, pp. 749-751 (2000).

Green et al., Protective Groups in Organic Chemistry, Wiley, 3rd ed., Chapter 2, pp. 17-200 (1999).

Green et al., Protective Groups in Organic Chemistry, Wiley, 3rd ed., Chapter 5, pp. 369-451 (1999).

Kitagawa et al., "Stereoselective Iodine Atom Transfer [3+2] Cycloaddition Reaction with Alkenes Using Unsymmetrical Allylated Active Methine Radicals", The Journal of Organic Chemistry vol. 69, No. 7, pp. 2607-2261 (2004).

* cited by examiner

ANTIFIBRINOLYTIC COMPOUNDS

The present invention relates to spirocyclic compounds of formula (I), to a process for their preparation, as well as to the intermediates used in this process. It also relates to pharmaceutical or veterinary compositions containing them, and to their use in medicine, in particular as antifibrinolytic and antihemorragic agents.

BACKGROUND ART

The haemostatic system is responsible for maintaining circulatory fluidity and for preventing haemorrhage in response to vascular injury. Physiological hemostasis is controlled by mechanisms of coagulation and the formation of fibrin and by those favouring the degradation of fibrin (fibrinolysis).

Hyperfibrinolytic states caused by congenital or acquired conditions predispose to important haemorrhagic complications, often requiring transfusions and the need for re-exploration having a detrimental effect on patient outcome. Hemorrhage is responsible for almost 50% of deaths occurring within 24 hours of traumatic injury and for up to 80% of intraoperative trauma mortality. In western countries about one third of in-hospital deaths due to trauma is caused by abnormal blood loss which is an important contributory factor for other causes of death, particularly multi-organ failure, requiring massive blood transfusion. Failure to start appropriate early management in bleeding trauma patients is a leading cause of preventable death from trauma. Post-partum hemorrhage (PPH) is another leading cause of death in the developing world, accounting for 25% of maternal deaths, and rose in the developed world from 1.5% in 1999 to 4.1% in 2009. The risk of haemorrhage can also be important in cardiovascular patients on anti-coagulant therapy. Pharmacological approaches are an important part of multimodal therapy aiming to reducing bleeding and transfusion in order to reverse specific defects associated with such states; among them, the role of fibrinolysis inhibitors is growing.

It is well known that subjects who bleed excessively in association with surgery or major trauma and need blood transfusions develop more complications than those who do not experience any bleeding. However, moderate bleeding requiring the administration of human blood products may lead to complications associated with the risk of transferring human viruses. Extensive bleeding requiring massive blood transfusions may lead to the development of multiple organ failure including lung or kidney function. Therefore, a major goal in surgery as well as in the treatment of major tissue damage is to avoid or minimise bleeding in order to ensure the formation of stable and solid haemostatic plugs that are not easily dissolved by fibrinolytic enzymes. Furthermore, it is of importance to ensure quick and effective formation of such plugs or clots.

Antifibrinolytic agents are widely used in major surgery to prevent fibrinolysis and reduce blood loss. Currently two synthetic lysine analogs, epsilon-aminocaproic acid (EACA) and tranexamic acid (TXA), are the only antifibrinolytics commercially available to control bleeding. These agents competitively inhibit activation of plasminogen to plasmin, an enzyme that degrades fibrin clots, fibrinogen and other plasma proteins. However, there are some concerns with these currently available antifibrinolytic agents due to the potential risk of thrombotic complications.

There is still a need for improved treatment of subjects experiencing bleeding episodes, including subjects where the bleeding episodes are due to surgery, trauma, or other forms of tissue damage, as well as in clinical scenarios characterized by excessive fibrinolysis.

SUMMARY OF THE INVENTION

Inventors have conceived and produced found a novel series of spirocyclic compounds that shows good antifibrinolytic and antihemorrhagic properties. In particular, the spirocyclic compounds which comprise spirocyclic ring system containing a carbon atom (spiro atom) attached to a hydroxamic acid and a sulfonyl group, show a significant delay in the lysis time in a thromboelastometry assay. In addition, the spirocyclic compounds of the invention also show an important reduction of the bleeding time in vivo animal models as it will be shown in detail in the examples. These characteristics of the compounds of the invention allow a rapid cessation of hemorrhage; favor an effective formation of plugs or clots; have a sustained action (persistence of the clot and prevention of hemorrhage) and aid in minimizing the adverse effects related to other antifibrinolytic/antihemorrhagic treatments having risk of thrombotic complications.

Therefore, a first aspect of the invention relates to a compound of formula (I) (hereinafter also referred as compounds of the invention), or a pharmaceutically or veterinary acceptable salt thereof, or any stereoisomer either of the compound of formula (I) or of its pharmaceutically or veterinary acceptable salt

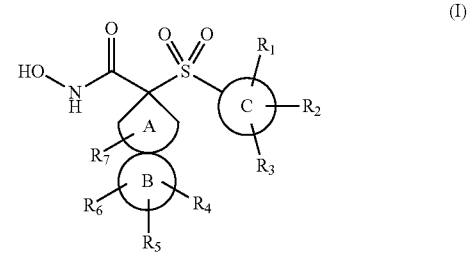

wherein
A and B form a spirocyclic ring system wherein the spiro atom connecting A and B is a carbon atom and wherein
A is a known 3- to 8-membered carbocyclic or heterocyclic monocyclic ring, saturated or partially unsaturated; or alternatively
A is a known 6- to 18-membered carbocyclic or heterocyclic polycyclic ring system, saturated, partially unsaturated, or partially aromatic; and
B is a known 4- to 7-membered carbocyclic or heterocyclic monocyclic ring, saturated or partially unsaturated;
C is phenyl or a known 5- to 6-membered heteroaromatic ring;
$R_1$-$R_3$ are independently selected from H, halogen, —$NO_2$, —CN, $R^a$, —$OR^{a'}$, —$OC(Y)R^{a'}$, —$OC(Y)OR^{a'}$, —$OC(Y)NR^bR^{a'}$, —$OSO_2OR^{a'}$, —$NR^bR^{a'}$, —$NR^bC(Y)R^{a'}$, —$NR^bC(Y)OR^{a'}$, —$NR^bC(Y)NR^bR^{a'}$, —$NR^bS(O)_2R^{a'}$, —$NR^bSO_2NR^bR^{a'}$, —$SR^{a'}$, —$S(O)R^{a'}$, —$S(O)OR^{a'}$, —$SO_2R^{a'}$, —$SO_2(OR^{a'})$, —$SO_2NR^bR^{a'}$, —$SC(Y)NR^bR^{a'}$, —$C(Y)R^{a'}$, —$C(Y)OR^{a'}$, —$C(Y)NR^bR^{a'}$, —$C(Y)NR^bOR^{a'}$, and —$C(O)NR^bSO_2R^{a'}$;
$R_4$-$R_7$ are independently selected from halogen, —$NO_2$, —CN, $R^c$, —$OR^c$, —$NR^dR^c$, —$NR^dC(Y)R^c$, —$NR^dC(Y)OR^c$, —$NR^dC(Y)NR^dR^c$, —$NR^dS(O)_2R^c$, —NR$^d$SO$_2$NR$^d$R$^c$, —SR$^c$, —S(O)R$^c$, —S(O)OR$^c$, —SO$_2$R$^c$, —SO$_2$R(OR$^c$), —SO$_2$NR$^d$R$^c$, —SC(Y)NR$^d$R$^c$, —C(Y)R$^c$, —C(Y)OR$^c$, —C(Y)NR$^d$R$^c$, —C(Y)NR$^d$OR$^c$, and —C(O)NR$^d$SO$_2$R$^c$ R$^a$ is a saturated or unsaturated (C$_1$-C$_{12}$)alkyl optionally substituted with one or more substituents R$^e$ and/or one Cy$^1$; or alternatively R$^a$ is Cy$^2$;

wherein Cy$^1$ and Cy$^2$ are independently optionally substituted with: one Cy$^3$ and/or one or more substituents R$^e$, and/or one or more saturated or unsaturated (C$_1$-C$_6$)alkyl groups optionally substituted with one or more substituents R$^e$ and/or one Cy$^3$; and wherein any Cy$^3$ is optionally substituted with one or more substituents independently selected from R$^e$ and saturated or unsaturated (C$_1$-C$_6$)alkyl optionally substituted with one or more substituents R$^e$;

each R$^{a'}$ and R$^b$ are independently H or R$^a$;

R$^c$ and each R$^d$ are independently selected from H, Cy$^4$, and saturated or unsaturated (C$_1$-C$_6$)alkyl optionally substituted with one or more substituents R$^h$ and/or one Cy$^5$;

wherein Cy$^4$ is optionally substituted with one or more substituents independently selected from R$^h$ and saturated or unsaturated (C$_1$-C$_6$)alkyl optionally substituted with one or more substituents R$^h$; and wherein Cy$^5$ is optionally substituted with one or more substituents independently selected from R$^h$ and saturated or unsaturated (C$_1$-C$_6$)alkyl optionally substituted with one or more substituents R$^h$;

each R$^e$ is independently selected from halogen, —NO$_2$, —CN, —OR$^f$, —OC(Y)R$^f$, —OC(Y)OR$^f$, —OC(Y)NR$^g$R$^f$, —NR$^g$R$^f$, —NR$^g$C(Y)R$^f$, —NR$^g$C(Y)OR$^f$, —NR$^g$C(Y)NR$^g$R$^f$, —NR$^g$S(O)$_2$R$^f$, —NR$^g$SO$_2$NR$^g$R$^f$, —SR$^f$, —S(O)R$^f$, —S(O)OR$^f$, —SO$_2$R$^f$, —SO$_2$(OR$^f$), —SO$_2$NR$^g$R$^f$, —SC(Y)NR$^g$R$^f$, —C(Y)R$^f$, —C(Y)OR$^f$, —C(Y)NR$^g$R$^f$, —C(Y)NR$^g$OR$^f$, and —C(O)NR$^g$SO$_2$R$^f$.

R$^f$ and each R$^g$ are independently selected from H, Cy$^6$, and saturated or unsaturated (C$_1$-C$_6$)alkyl optionally substituted with one or more substituents R$^h$ and/or one Cy$^7$;

wherein Cy$^6$ is optionally substituted with: one Cy$^7$, and/or one or more substituents R$^h$, and/or one or more saturated or unsaturated (C$_1$-C$_6$)alkyl groups optionally substituted with one or more substituents R$^h$ and/or one Cy$^7$; and wherein any Cy$^7$ is optionally substituted with one or more substituents independently selected from R$^h$ and (C$_1$-C$_4$)alkyl optionally substituted with one or more substituents R$^h$;

each R$^h$ is independently selected from halogen, —NO$_2$, —CN, —OR$^i$, —OC(O)R$^i$, —OC(O)OR$^i$, —OC(O)NR$^i$R$^i$, —NR$^i$R$^i$, —NR$^i$C(O)R$^i$, —NR$^i$C(O)OR$^i$, —NR$^i$C(O)NR$^i$R$^i$, —NR$^i$S(O)$_2$R$^i$, —NR$^i$SO$_2$NR$^i$R$^i$, —SR$^i$, —S(O)R$^i$, —SO$_2$R$^i$, —SO$_2$(OR$^i$), —SO$_2$NR$^i$R$^i$, —C(O)R$^i$, —C(O)OR$^i$, —C(O)NR$^i$R$^i$, and —C(O)NR$^i$OR$^i$ each R$^i$ is independently H or —(C$_1$-C$_4$)alkyl optionally substituted with one or more halogen atoms;

Y is O, S, or NR$^i$;

Cy$^1$, Cy$^2$, Cy$^4$ and Cy$^6$ are independently a C or N-attached known ring system selected from 3- to 8-membered carbocyclic or heterocyclic monocyclic ring, saturated or partially unsaturated; phenyl; 5- or 6-membered heteroaromatic ring; and 6- to 18-membered carbocyclic or heterocyclic polycyclic ring system, saturated, partially unsaturated, aromatic or partially aromatic;

Cy$^3$, Cy$^5$ and Cy$^7$ are independently a C or N-attached known ring system selected from 3- to 8-membered carbocyclic or heterocyclic monocyclic ring, saturated or partially unsaturated; phenyl; and 5- or 6-membered heteroaromatic ring;

wherein in the carbocyclic rings all ring members are carbon atoms; and in the heterocyclic and heteroaromatic rings one or more ring members are selected from N, O, and S; and wherein in all saturated or partially unsaturated rings one or two members of the rings are optionally C(O) and/or C(NH) and/or C[N(C$_1$-C$_4$)alkyl].

Another aspect of the invention relates to a pharmaceutical or veterinary composition which comprises an effective amount of a compound of formula (I) as defined above, or a pharmaceutically or veterinary acceptable salt thereof, or any stereoisomer either of the compound of formula (I) or of its pharmaceutically or veterinary acceptable salt, together with one or more pharmaceutically or veterinary acceptable excipients or carriers.

As previously described, the compounds of the invention are useful as antifibrinolytic and antihemorrhagic agents. Therefore, another aspect of the invention relates to a compound of formula (I) as defined above, or a pharmaceutically or veterinary acceptable salt thereof, or any stereoisomer either of the compound of formula (I) or of its pharmaceutically or veterinary acceptable salt, for use as a medicament.

Another aspect of the invention relates to a compound of formula (I) as defined above, or a pharmaceutically or veterinary acceptable salt thereof, or any stereoisomer either of the compound of formula (I) or of its pharmaceutically or veterinary acceptable salt, for use as antifibrinolytic and antihemorrhagic agent. Thus, this aspect relates to the use of a compound of formula (I) as defined above, for the manufacture of a medicament for use as antifibrinolytic and antihemorrhagic agent; and may also be formulated as a method for the treatment and/or prevention of hyperfibrinolysis and/or hemorrhages comprising administering an effective amount of the previously defined compound of formula (I), or a pharmaceutically or veterinary acceptable salt thereof, or any stereoisomer either of the compound of formula (I) or of its pharmaceutically or veterinary acceptable salt, and one or more pharmaceutically or veterinary acceptable excipients or carriers, in a subject in need thereof, including a human.

Processes for the preparation of compounds of formula (I) are also part of the invention as well as intermediates used in these processes. Accordingly, another aspect of the invention relates to a compound of formula (III)

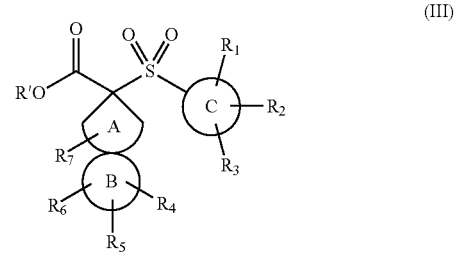

(III)

wherein A, B, C, R$_1$-R$_7$ are as defined above, and R' is H or a carboxy protective group, more particularly a carboxy protective group selected from the group consisting of (C$_1$-C$_6$)alkyl, benzyl, p-methoxyphenyl, trimethylsilyl and [2-(Trimethylsilyl)ethoxy]methyl (SEM), with the proviso that compound (III) is other than 7-methoxycarbonyl-7-phenylsulphonyl-2-oxaspiro[2.4]-heptane and (2S*,4R*)-2-Phenylsulfonyl-4-iodomethyl-6,11-dioxaspiro[4.6]-undecane-2-carboxylic acid methyl ester.

Another aspect of the invention relates to a compound of formula (II)

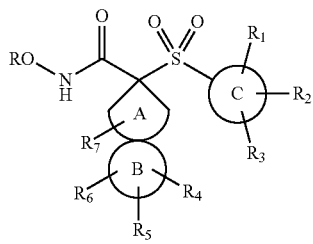

wherein A, B, C, $R_1$-$R_7$ are as defined above, and R is an hydroxamic acid protective group, more particularly an hydroxamic acid protective group selected from the group consisting of tetrahydro-2H-pyran-2-yloxy (THP), benzyl, 1-naphthylmethyl and dimethyloxybenzyl (DMB).

DETAILED DESCRIPTION OF THE INVENTION

All terms as used herein in this application, unless otherwise stated, shall be understood in their ordinary meaning as known in the art. Other more specific definitions for certain terms as used in the present application are as set forth below and are intended to apply uniformly through-out the specification and claims unless an otherwise expressly set out definition provides a broader definition.

For the purposes o the present invention, in the spirocyclic ring system formed by the ring system A and ring system B, the spiro atom connecting A and B is a carbon atom.

The term "carbocyclic" ring system refers to a known ring system wherein all the ring members are carbon atoms. The term "heterocyclic" ring system refers to a known ring system wherein one or more of the ring members, preferably 1, 2, 3, or 4 ring members, are selected from N, O, and S, where chemically possible. Unless otherwise specified, the "heterocyclic" ring system may be attached to the rest of the molecule through a C or a N atom. Both the carbocyclic and heterocyclic rings can be saturated or partially unsaturated, and may be unsubstituted or substituted as described herein, being the substituents placed on any available position.

According to the present invention, the term "polycyclic" ring refers to a ring system which is formed by two, three or four rings which can be fused, bridged-fused, spiro-fused or can contain different types of fusion. For the purposes of the present invention, in "fused" rings the fusion occurs through one bond which is common to two adjoining rings; in "bridged-fused" rings the fusion occurs through a sequence of atoms (bridgehead) which is common to two rings; and in "spiro-fused" rings, the fusion occurs through only one atom (spiro atom), preferably a carbon atom, which is common to two adjoining rings (including bridged rings)

The polycyclic ring system can be saturated, partially unsaturated, aromatic (except in the case of ring system A) or partially aromatic; and may be unsubstituted or substituted as described herein, being the substituents placed on any available position.

The term "heteroaromatic" ring refers to a known aromatic ring system, wherein one or more of the ring members, preferably 1, 2, 3, or 4 ring members, are selected from N, O, and S where chemically possible. The heteroaromatic ring and phenyl may be unsubstituted or substituted as described herein, being the substituents placed on any available position.

The term "known" ring system as used herein refers to a ring system which is chemically feasible and is known in the art and so intends to exclude those ring systems that are not chemically possible.

For the purposes of the present invention, in all saturated or partially unsaturated rings, one or two members of the rings are optionally C(O) and/or C(NH) and/or C[N($C_1$-$C_4$) alkyl].

The term saturated or unsaturated ($C_1$-$C_n$)alkyl refers to a saturated branched or linear hydrocarbon chain which contains from 1 to n carbon atoms. When the ($C_1$-$C_n$)alkyl is saturated it contains only single bonds. When the ($C_1$-$C_n$) alkyl is unsaturated it contains one or two double bonds and/or one or two triple bonds. The saturated or unsaturated ($C_1$-$C_n$)alkyl may be substituted or unsubstituted as described herein.

A halogen substituent means fluoro, chloro, bromo or iodo.

"Protective group" (PG) refers to a grouping of atoms that when attached to a reactive group in a molecule masks, reduces or prevents that reactivity.

The expression "substituted with one or more" means that a group can be substituted with one or more, preferably with 1, 2, 3 or 4 substituents, provided that this group has enough positions susceptible of being substituted.

For the purposes of the invention, room temperature is 20-25° C.

As mentioned above, a first aspect of the invention relates to compounds of formula (I) or pharmaceutically or veterinary acceptable salts thereof, or any stereoisomer either of the compound of formula (I) or of its pharmaceutically or veterinary acceptable salt. There is no limitation on the type of salt that can be used, provided that these are pharmaceutically or veterinary acceptable when they are used for therapeutic purposes. The term "pharmaceutically or veterinary acceptable salts", embraces salts commonly used to form alkali metal salts and to form addition salts of free acids or free bases.

The preparation of pharmaceutically or veterinary acceptable salts of the compounds of formula (I) can be carried out by methods known in the art. For instance, they can be prepared from the parent compound, which contains a basic or acidic moiety, by conventional chemical methods. Generally, such salts are, for example, prepared by reacting the free acid or base forms of these compounds with a stoichiometric amount of the appropriate pharmaceutically or veterinary acceptable base or acid in water or in an organic solvent or in a mixture of them. The compounds of formula (I) and their salts may differ in some physical properties but they are equivalent for the purposes of the present invention.

The compounds of the invention may be in crystalline form either as free solvation compounds or as solvates (e.g. hydrates) and it is intended that both forms are within the scope of the present invention. Methods of solvation are generally known within the art. In general, the solvated forms with pharmaceutically or veterinary acceptable solvents such as water, ethanol and the like are equivalent to the unsolvated form for the purposes of the invention.

Some compounds of formula (I) can have chiral centres that can give rise to various stereoisomers. The present invention relates to each of these stereoisomers and also mixtures thereof. Moreover, some of the compounds of the present invention can show cis/trans isomers. The present invention relates to each of the geometric isomers and mixtures thereof.

Diastereoisomers can be separated by conventional techniques such as chromatography or fractional crystallization. Optical isomers can be resolved by conventional techniques of optical resolution to give optically pure isomers. This resolution can be carried out on any chiral synthetic intermediate or on products of general formula (I). Optically pure isomers can also be individually obtained using enantiospecific synthesis.

In one embodiment, the invention refers to a compound of formula (I) as defined above, wherein A is a known 3- to 8-membered carbocyclic or heterocyclic monocyclic ring or a known 6- to 10-membered carbocyclic or heterocyclic bicyclic ring system.

In another embodiment, the invention refers to a compound of formula (I), wherein A is a monocyclic ring selected from a 3- to 6-membered carbocyclic ring, and a 5- to 6-membered heterocyclic ring.

In another embodiment, the invention refers to a compound of formula (I), wherein A is a carbocyclic monocyclic ring; or a polycyclic ring system, preferably a bicyclic ring system, wherein the ring containing the spiro atom attached to the hydroxamic acid and the sulfonyl group is a carbocyclic ring.

In another embodiment, the invention refers to a compound of formula (I), wherein A is selected from cyclopropane, cyclobutane, cyclopentane, cyclohexane, tetrahydrofuran, pyrrolidine, bicyclo[2.2.1]heptane, 2,3-dihydro-1H-indene, hexahydropyrrolizin-3-one, and 4-azaspiro[4.4]nonane.

In another embodiment, the invention refers to a compound of formula (I), wherein A is unsubstituted, i.e. $R_7$ is H.

In another embodiment, the invention refers to a compound of formula (I), wherein B is a 6- to 7-membered carbocyclic or heterocyclic monocyclic ring.

In another embodiment, the invention refers to a compound of formula (I), wherein B is a saturated monocyclic ring, carbocyclic or heterocyclic, wherein at least one of the ring members of the heterocyclic ring is $NR_4$.

In another embodiment, the invention refers to a compound of formula (I), wherein B is selected from cyclohexane, piperidine, morpholine, azepane, piperazine, pyrrolidine, and azetidine.

In another embodiment, B is piperidine, morpholine, azepane, pyrrolidine, and azetidine, wherein $R_4$ is placed on the N atom of these rings and $R_5$-$R_6$ are H. In another embodiment, B is piperazine, wherein $R_4$ and $R_5$ are placed on the N atoms and $R_6$ is H.

In another embodiment, the invention refers to a compound of formula (I), wherein A and B form a spirocyclic ring system selected from the group consisting of:

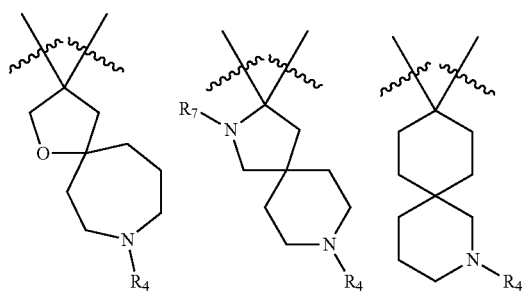

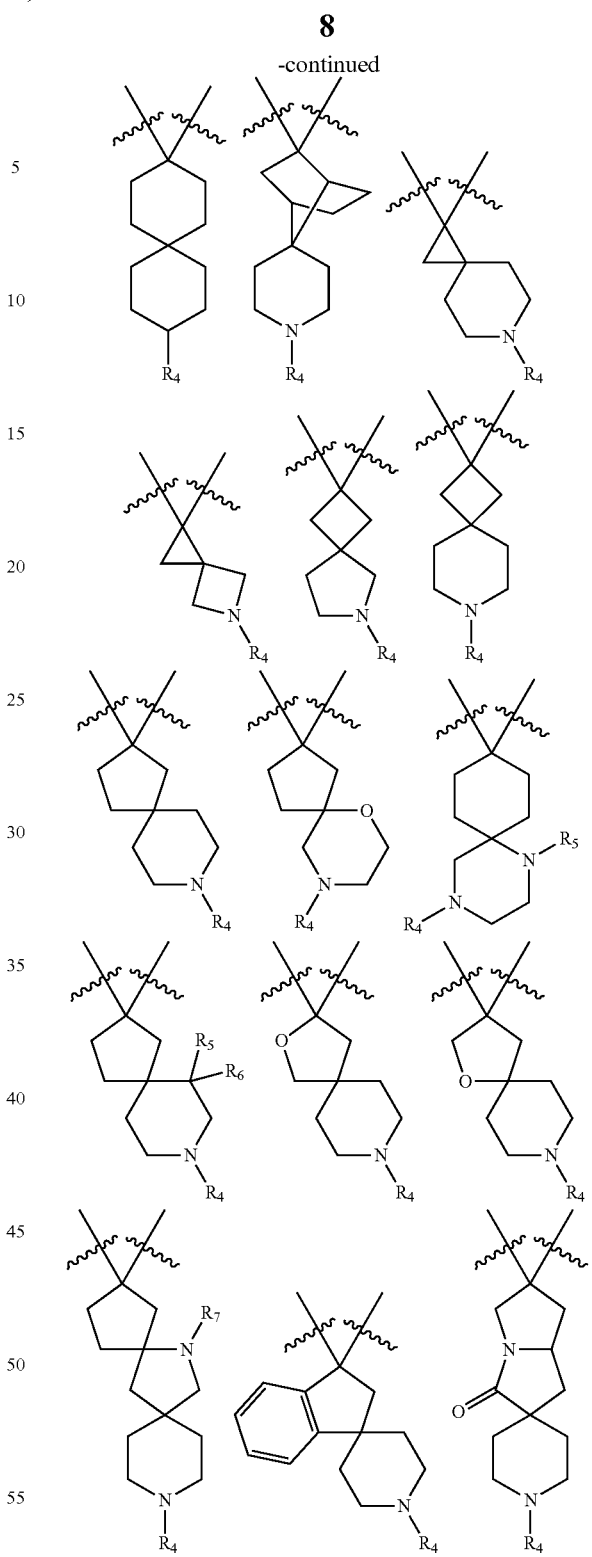

In another embodiment, the invention refers to a compound of formula (I), wherein C is phenyl. In another embodiment, C is phenyl substituted with $R^1$ at the orto, meta or para position, and $R_2$ and $R_3$ are independently selected from H, halogen, $R^a$, —$OR^{a'}$, and —$NR^bR^{a'}$; wherein $R^a$, $R^{a'}$ and $R^b$ are independently selected from H and —($C_1$-$C_4$)alkyl optionally substituted with one or more halogen atoms. In another embodiment, C is phenyl substituted with $R_1$ at the para position and $R_2$ and $R_3$ are H. In another embodiment, C is phenyl substituted with $R^1$ at the orto position and $R_2$ and $R_3$ are H. In another embodiment, C is phenyl substituted with $R^1$ at the meta position and $R_2$ and $R_3$ are H. In another embodiment, C is phenyl substituted with $R^1$ at the meta position, and $R_2$ at the para position, $R_3$ being H; or alternatively, C is phenyl substituted with $R^1$ at the para position, and $R_2$ at the meta position, $R_3$ being H; wherein $R_2$ is selected from H, halogen, $R^a$, —$OR^{a'}$, and —$NR^bR^{a'}$; and $R^a$, $R^{a'}$ and $R^b$ are independently selected from H and —($C_1$-$C_4$)alkyl optionally substituted with one or more halogen atoms.

In another embodiment, the invention refers to a compound of formula (I), wherein in $R^b$ (relating to $R_1$-$R_3$), $Cy^1$ and $Cy^2$ are independently optionally substituted with one or more substituents selected from $R^e$ and saturated or unsaturated ($C_1$-$C_6$)alkyl optionally substituted with one or more substituents $R^e$; and $Cy^6$ is optionally substituted with one or more substituents independently selected from $R^h$ and saturated or unsaturated ($C_1$-$C_6$)alkyl optionally substituted as previously defined, more particularly with one or more substituents $R^h$.

In a more particular embodiment, the invention refers to a compound of formula (I), wherein in $R^b$ (relating to $R_1$-$R_3$), $R^b$ is H and saturated or unsaturated ($C_1$-$C_{12}$)alkyl optionally substituted with one or more substituents $R^e$, more particularly wherein in $R^e$, $R^f$ and each $R^g$ are independently selected from H and saturated or unsaturated ($C_1$-$C_6$)alkyl optionally substituted with one or more fluorine atoms.

In another embodiment, the invention refers to a compound of formula (I), wherein in $R_1$-$R_3$, $R^e$ is selected from halogen, —$NO_2$, —CN, —$OR^f$, —$OC(O)R^f$, —$OC(O)OR^f$, —$OC(O)NR^gR^f$, —$NR^gR^f$, —$NR^gC(O)R^f$, —$NR^gC(O)OR^f$, —$NR^gC(O)NR^gR^f$, —$NR^gS(O)_2R^f$, —$SR^f$, —$S(O)R^f$, —$SO_2R^f$, —$SO_2NR^gR^f$, —$C(O)R^f$, —$C(O)OR^f$, —$C(O)NR^gR^f$, and —$C(O)NR^gOR^f$.

In another embodiment, the invention refers to a compound of formula (I), wherein in $R_1$-$R_3$, $R^f$ and each $R^g$ are independently selected from H and saturated or unsaturated ($C_1$-$C_6$)alkyl optionally substituted with one or more fluorine atoms.

In another embodiment, the invention refers to a compound of formula (I), wherein in $R_1$-$R_3$, $Cy^1$ and $Cy^2$ are independently optionally substituted with one or more substituents selected from $R^e$ and saturated or unsaturated ($C_1$-$C_6$)alkyl optionally substituted as previously defined; and $Cy^6$ is optionally substituted with one or more substituents independently selected from $R^h$ and saturated or unsaturated ($C_1$-$C_6$)alkyl optionally substituted as previously defined.

In another embodiment, the invention refers to a compound of formula (I), wherein $R_1$-$R_3$ are independently selected from H, halogen, —$NO_2$, —CN, $R^a$, —$OR^{a'}$, —$OC(O)R^{a'}$, —$OC(O)OR^{a'}$, —$OC(O)NR^bR^{a'}$, —$NR^bR^{a'}$, —$NR^bC(O)R^{a'}$, —$NR^bC(O)OR^{a'}$, —$NR^bC(O)NR^bR^{a'}$, —$NR^bS(O)_2R^{a'}$, —$SR^{a'}$, —$S(O)R^{a'}$, —$SO_2R^{a'}$, —$SO_2NR^bR^{a'}$, —$C(O)R^{a'}$, —$C(O)OR^{a'}$, —$C(O)NR^bR^{a'}$, and —$C(O)NR^bOR^{a'}$.

In another embodiment, the invention refers to a compound of formula (I), wherein in $R_4$-$R_7$, $R^h$ is selected from halogen, —$NO_2$, —CN, —$OR^i$, —$OC(O)R^i$, —$OC(O)OR^i$, —$OC(O)NR^iR^i$, —$NR^iR^i$, —$NR^iC(O)R^i$, —$NR^iC(O)OR^i$, —$NR^iC(O)NR^iR^i$, —$NR^iS(O)_2R^i$, —$SR^i$, —$S(O)R^i$, —$SO_2R^i$, —$SO_2NR^iR^i$, —$C(O)R^i$, —$C(O)OR^i$, and —$C(O)NR^iR^i$.

In another embodiment, the invention refers to a compound of formula (I), wherein $R_4$-$R_7$ are independently selected from halogen, —$NO_2$, —CN, $R^c$, —$OR^c$, —$NR^dR^c$, —$NR^dC(O)R^c$, —$NR^dC(O)OR^c$, —$NR^dC(O)NR^dR^c$, —$NR^dS(O)_2R^c$, —$SR^c$, —$S(O)R^c$, —$SO_2R^c$, —$SO_2NR^dR^c$, —$C(O)R^c$, —$C(O)OR^c$, and —$C(O)NR^dR^c$.

In another embodiment, the invention refers to a compound of formula (I), wherein $R_2$ and $R_3$ are independently selected from H, halogen, $R^a$, —$OR^{a'}$, and —$NR^bR^{a'}$; and $R_5$-$R_7$ are independently selected from H, halogen, $R^c$, —$OR^c$, and —$NR^dR^c$, wherein $R^a$, $R^{a'}$, $R^b$, $R^c$ and $R^d$ are independently selected from H and —($C_1$-$C_4$)alkyl optionally substituted with one or more fluorine atoms.

In another embodiment, the invention refers to a compound of formula (I), wherein $R_1$ is selected from H, halogen, —$NO_2$, —CN, $R^a$, —$OR^{a'}$, —$OR^{a'}$, —$OC(O)R^{a'}$, —$OC(O)OR^{a'}$, —$OC(O)NR^bR^{a'}$, —$NR^bR^{a'}$, —$NR^bC(O)R^{a'}$, —$NR^bC(O)OR^{a'}$, —$NR^bC(O)NR^bR^{a'}$, —$NR^bS(O)_2R^{a'}$, —$SR^{a'}$, —$S(O)R^{a'}$, —$SO_2R^{a'}$, —$SO_2NR^bR^{a'}$, —$C(O)R^{a'}$, —$C(O)OR^{a'}$, —$C(O)NR^bR^{a'}$, and —$C(O)NR^bOR^{a'}$; $R_4$ is selected from halogen, —$NO_2$, —CN, $R^c$, —$OR^c$, —$NR^dR^c$, —$NR^dC(O)R^c$, —$NR^dC(O)OR^c$, —$NR^dC(O)NR^dR^c$, —$NR^dS(O)_2R^c$, —$SR^c$, —$S(O)R^c$, —$SO_2R^c$, —$SO_2NR^dR^c$, —$C(O)R^c$, —$C(O)OR^c$, and —$C(O)NR^dR^c$; and $R_2$, $R_3$, and $R_5$-$R_7$ are independently selected from H, halogen, —($C_1$-$C_4$)alkyl, —OH, —O[($C_1$-$C_4$)alkyl], —$NH_2$, —NH[($C_1$-$C_4$)alkyl], —N[($C_1$-$C_4$)alkyl]$_2$, wherein each ($C_1$-$C_4$)alkyl is independently optionally substituted with one or more fluorine atoms.

The present invention also relates to the combination of any of the specific embodiments defined above for any of the variables A, B, C, and $R_1$-$R_7$.

In another embodiment of the invention, the compound of formula (I) is selected from the group consisting of:

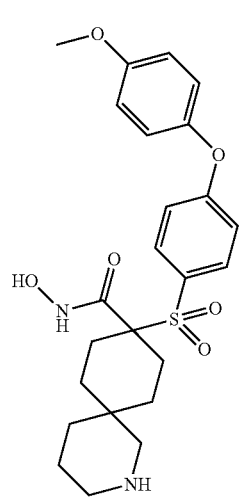

1-01

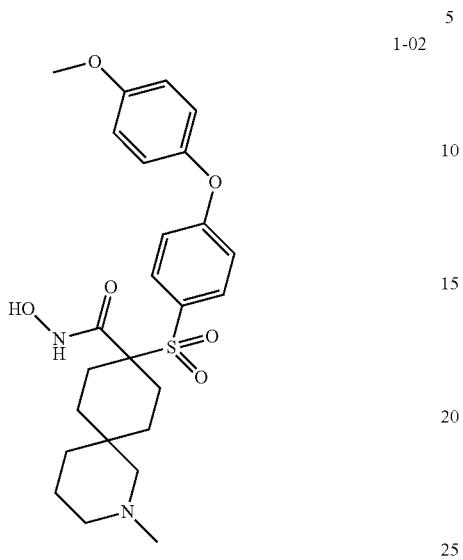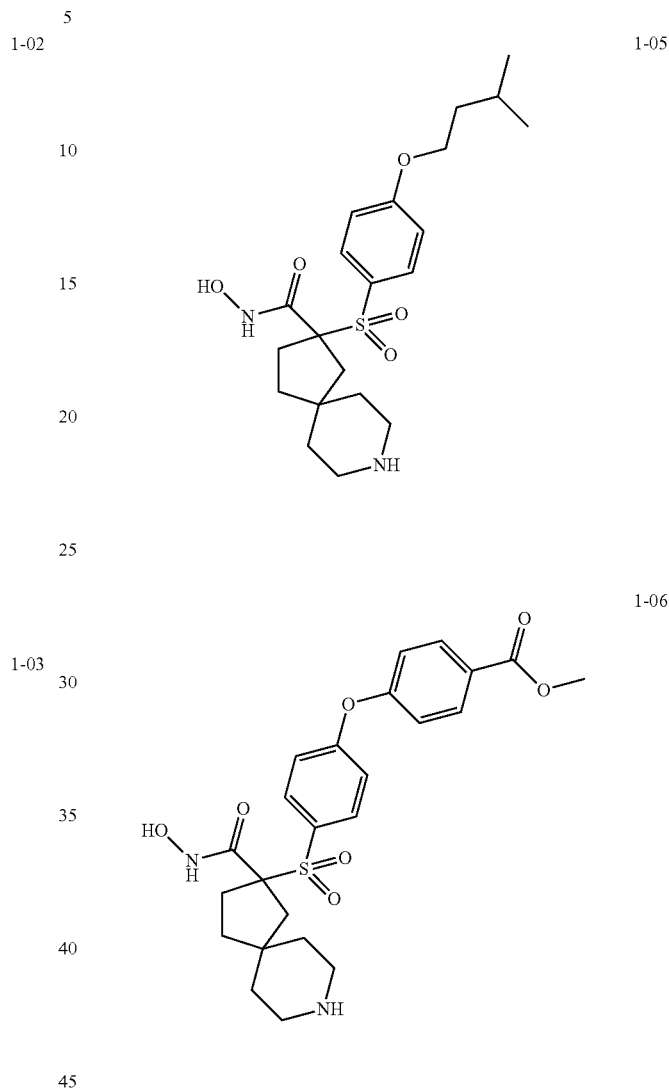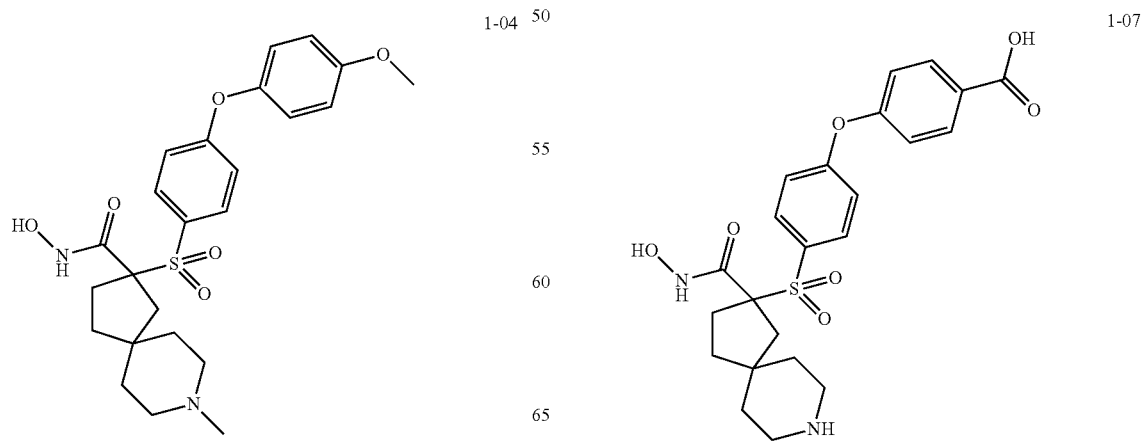

-continued
1-08
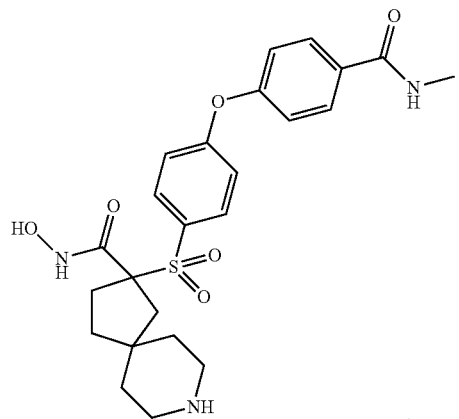
1-09
1-10
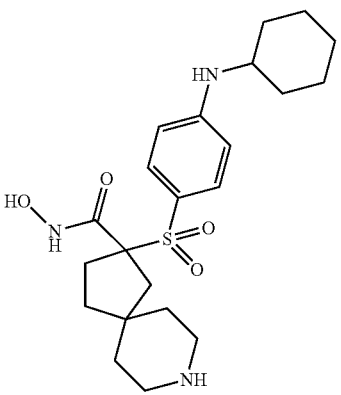
1-11
-continued
1-12
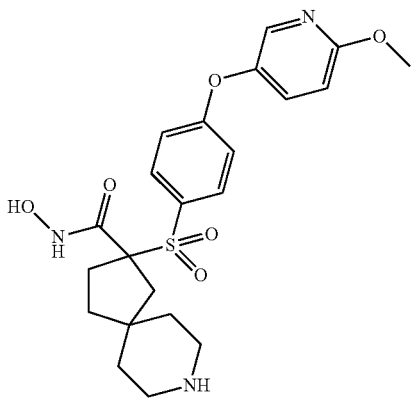
1-13
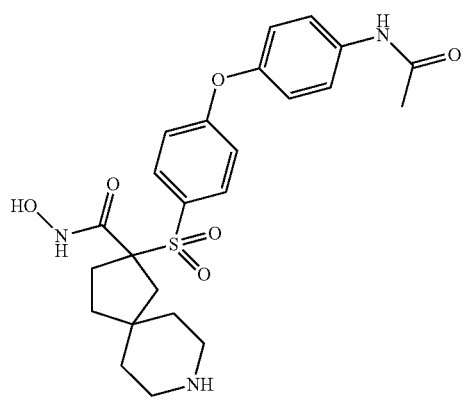
1-14
1-15
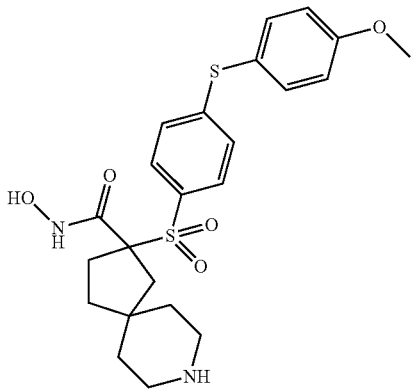

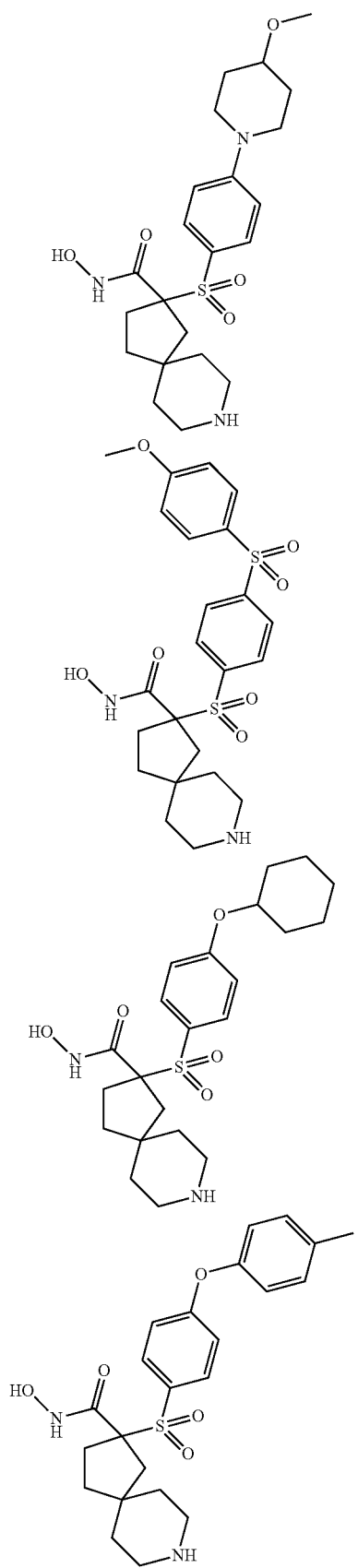
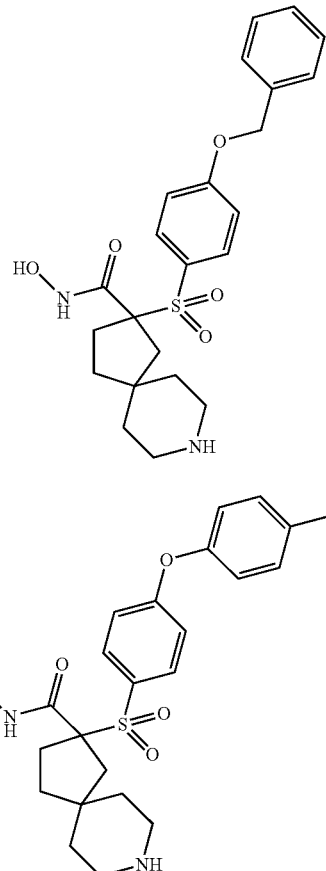
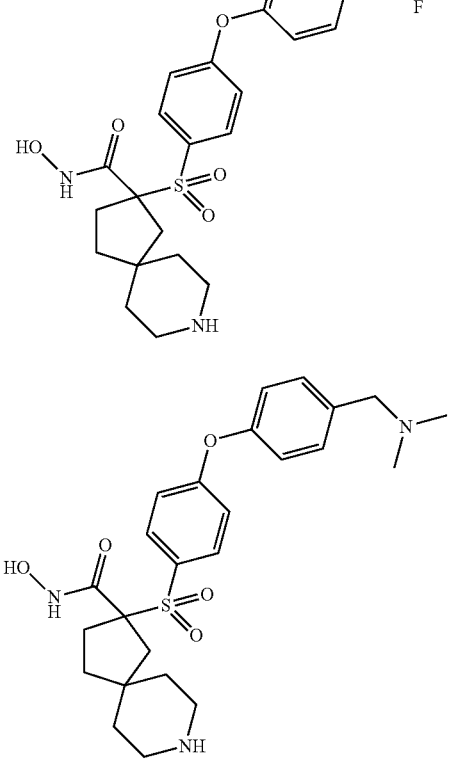
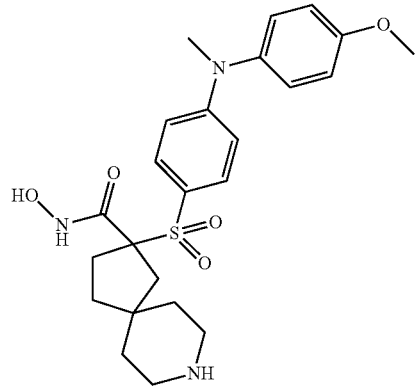

1-24
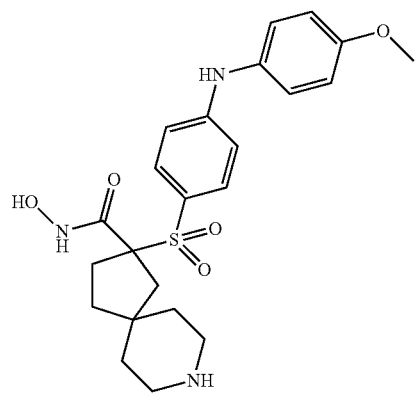
1-25
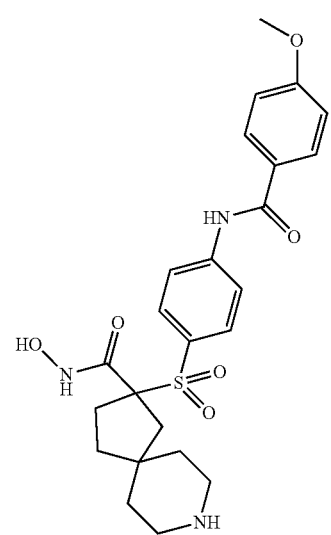
1-26
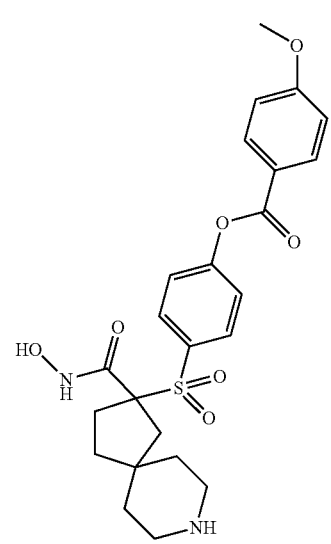
1-27
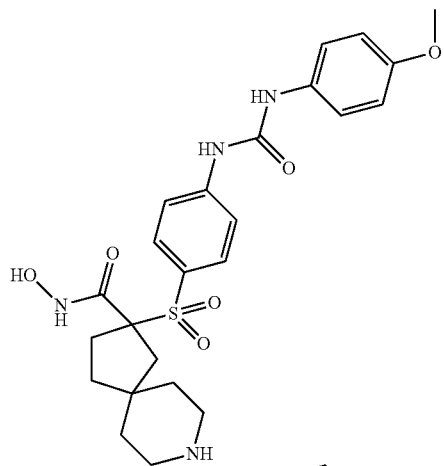
1-28
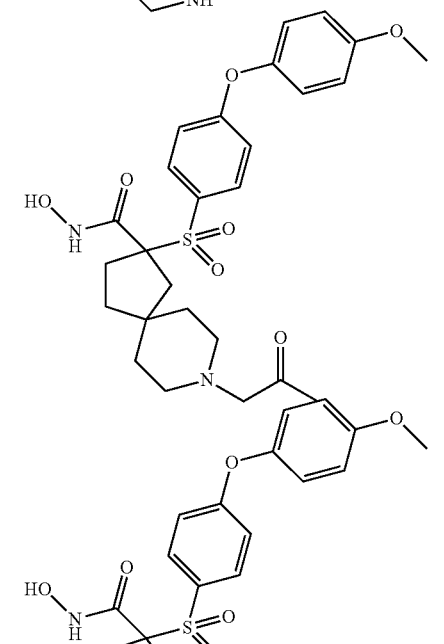
1-29
1-30
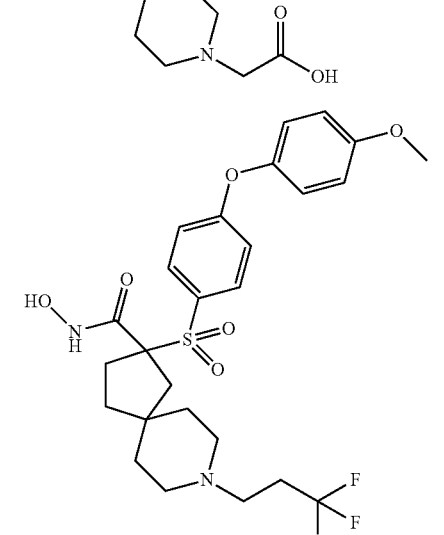

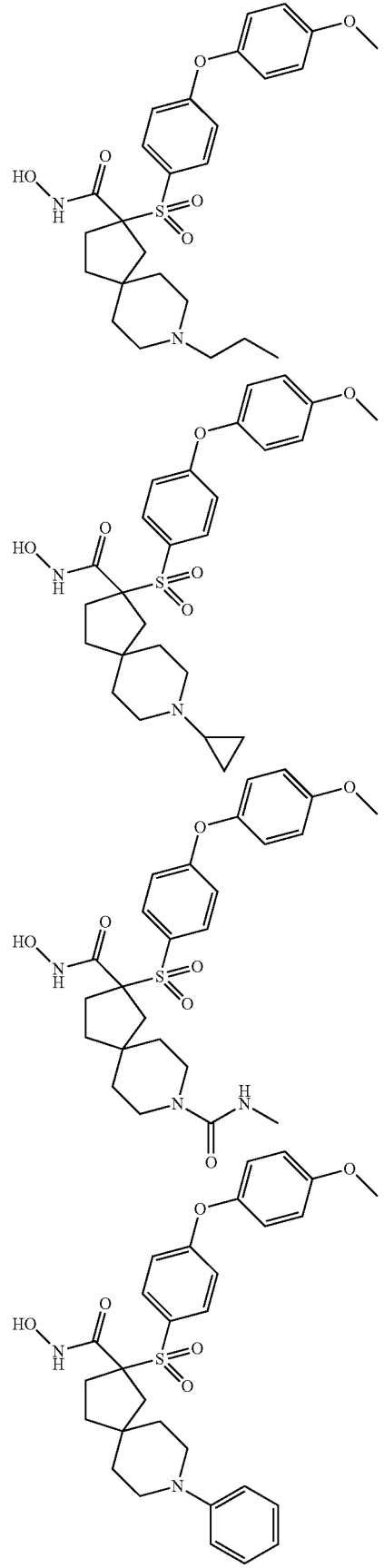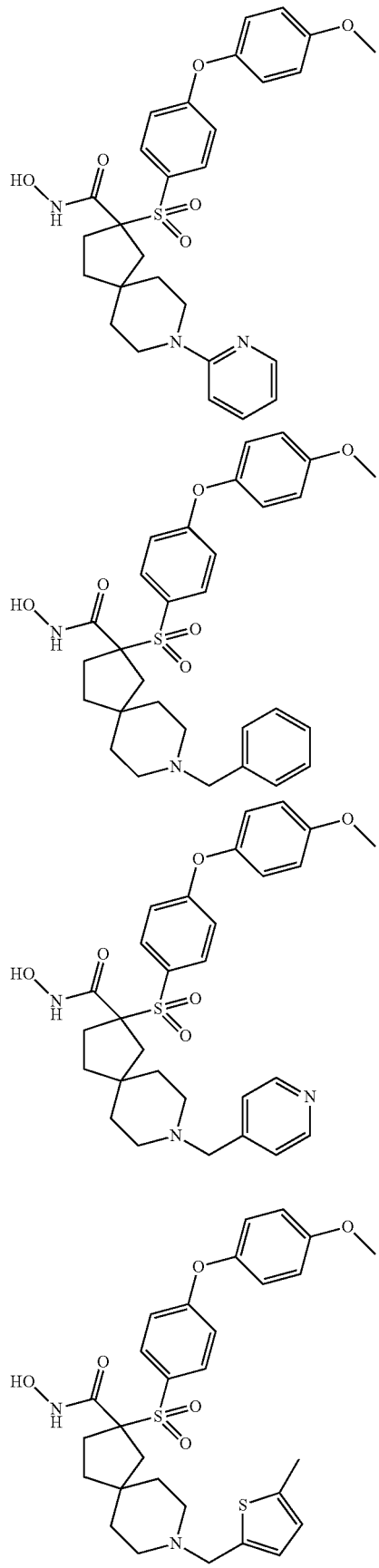

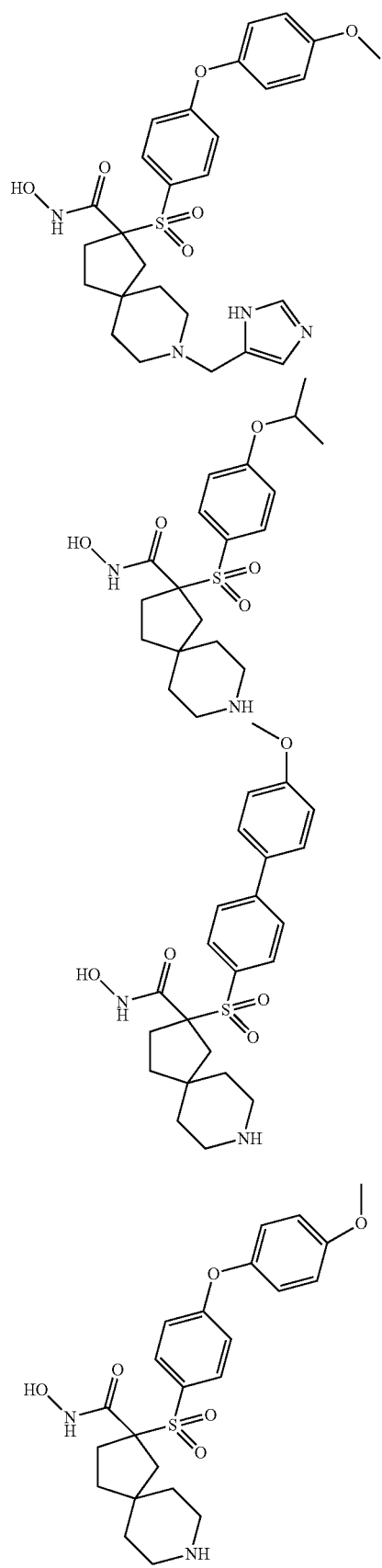
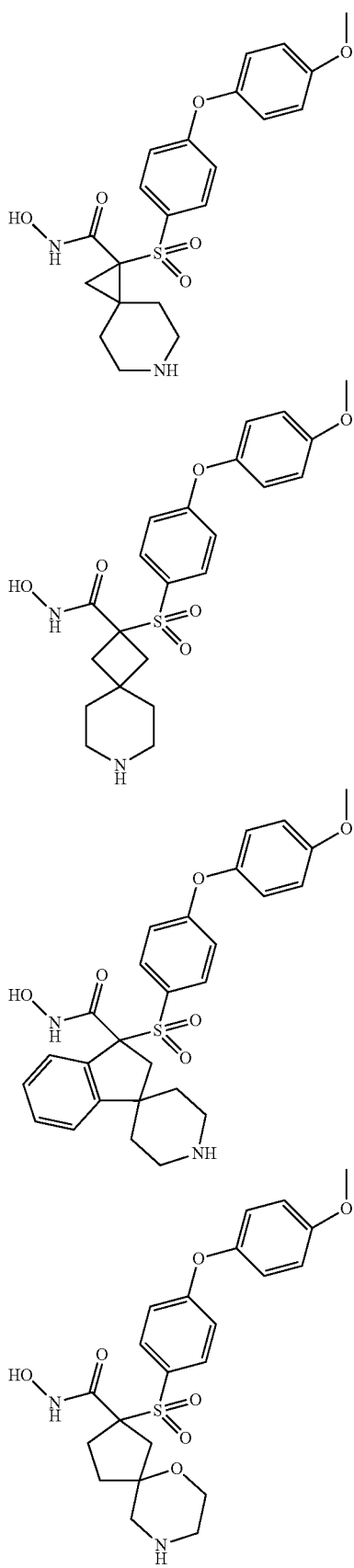

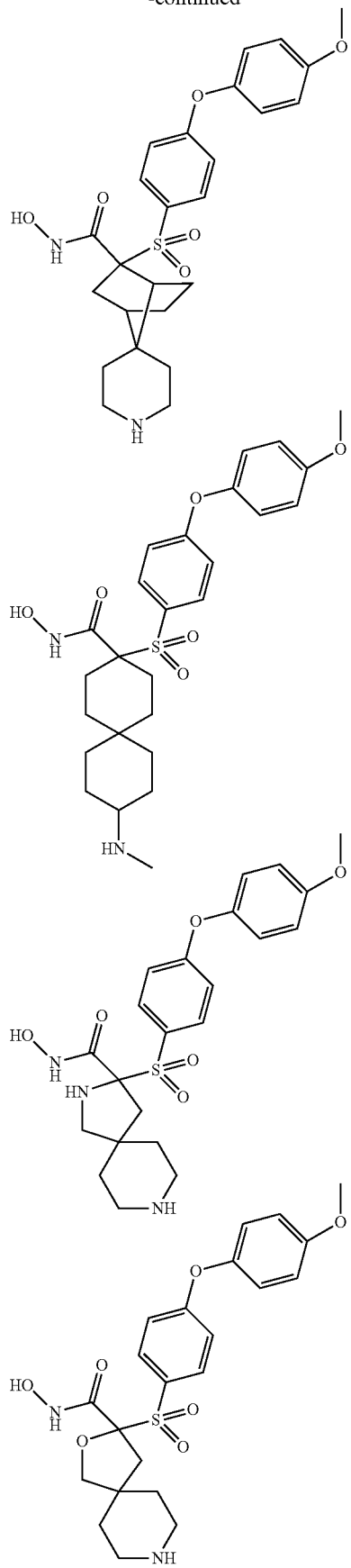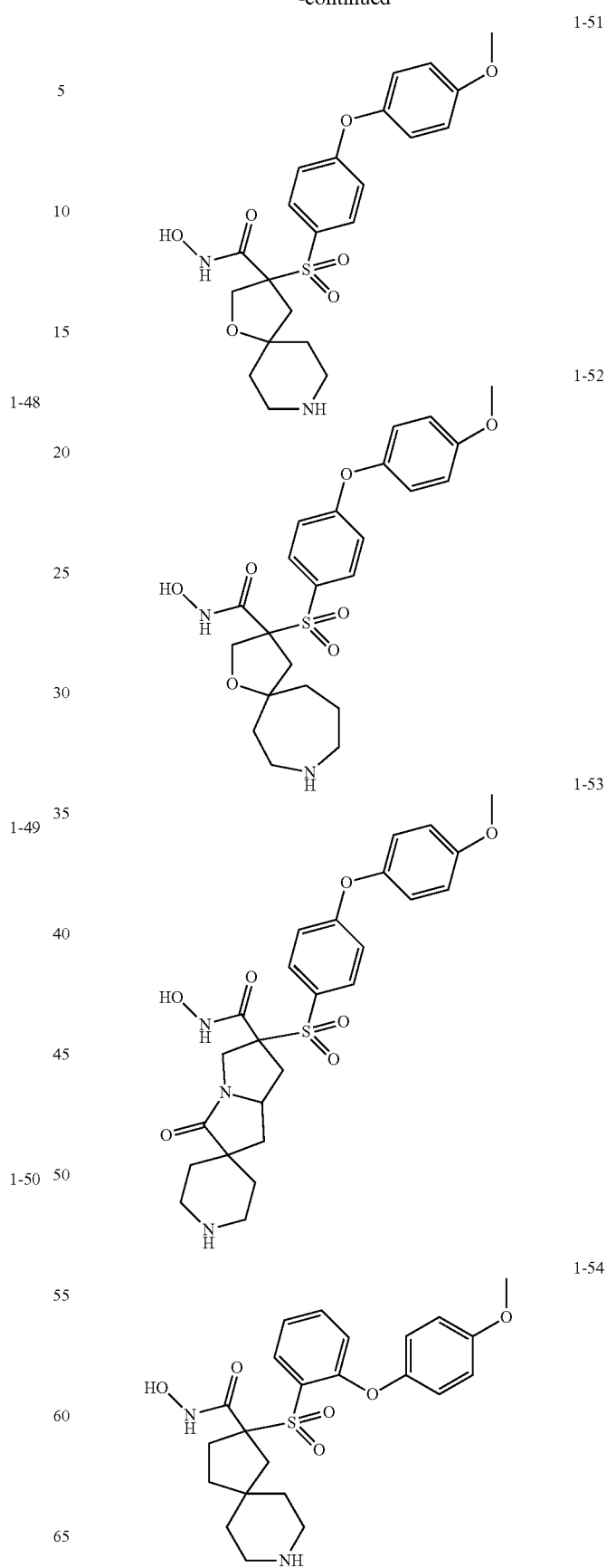

1-55 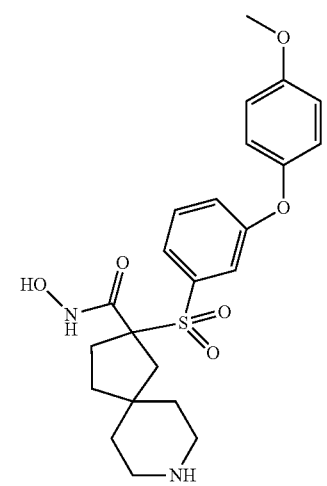
1-56 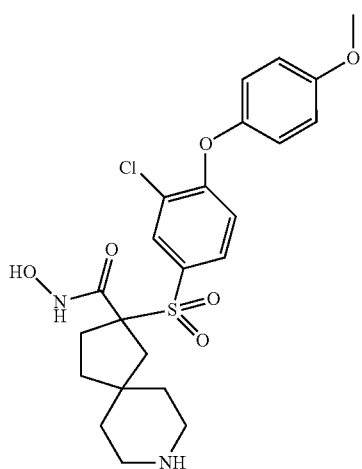
1-57 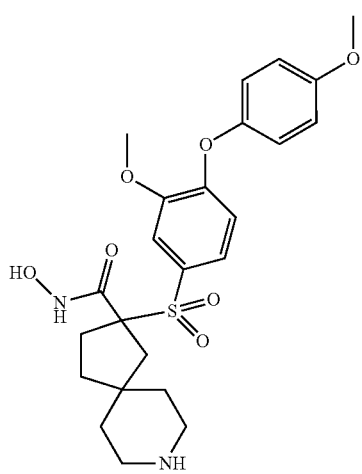
1-58 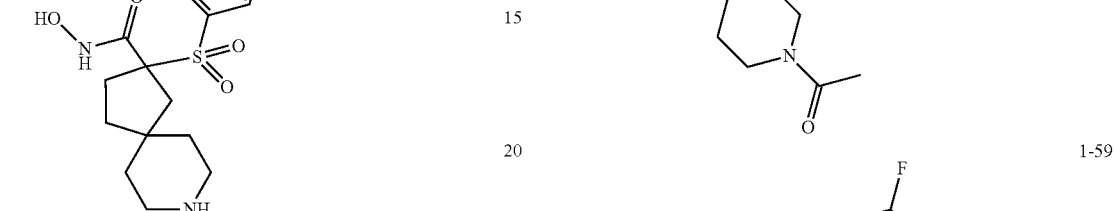
1-59 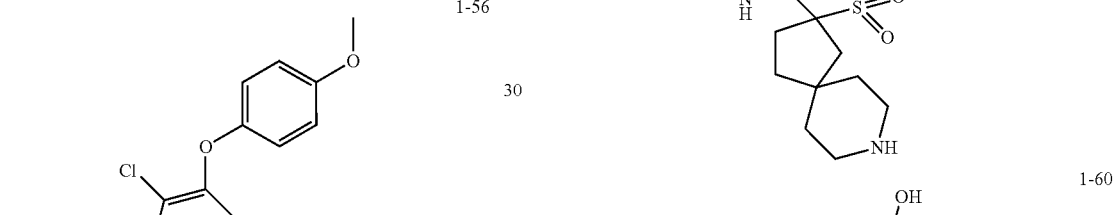
1-60 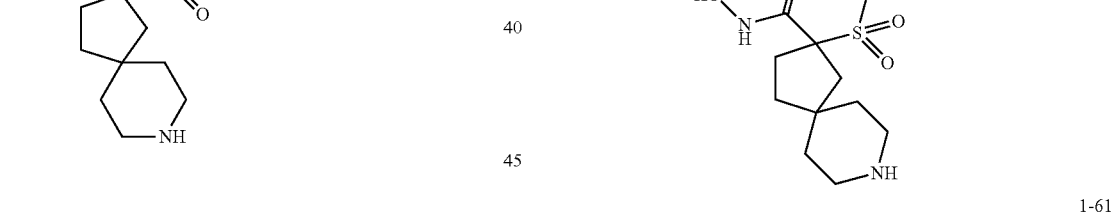
1-61 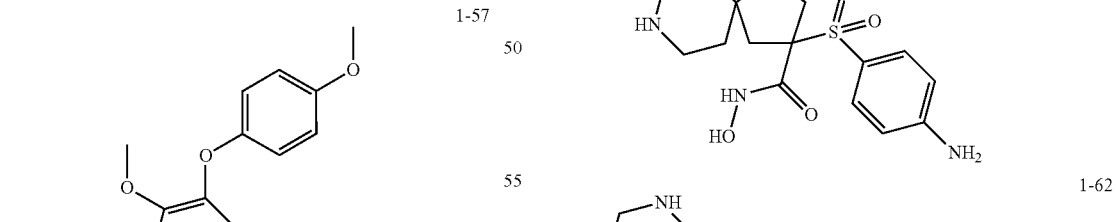
1-62 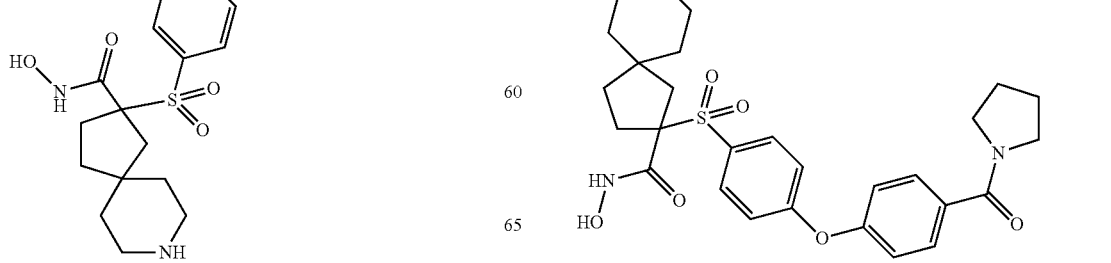

-continued
1-63
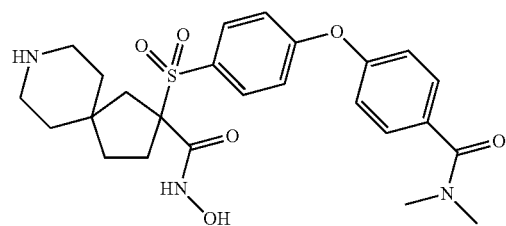
1-64
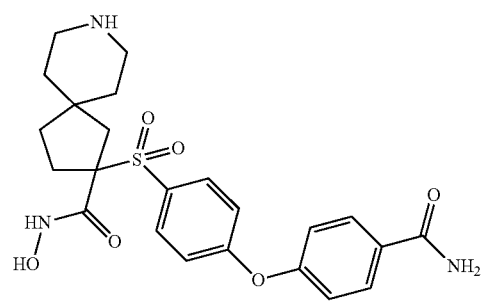
1-65
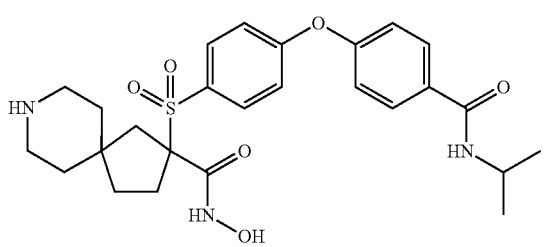
1-66
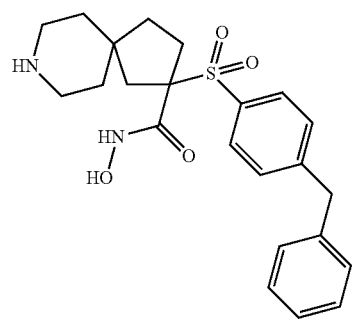
1-67
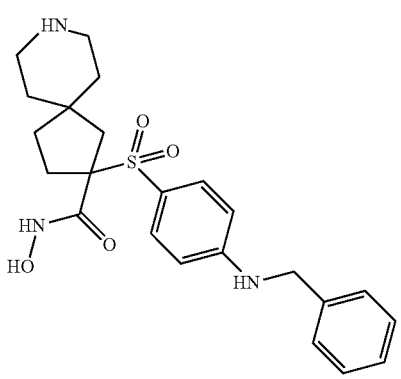
-continued
1-68
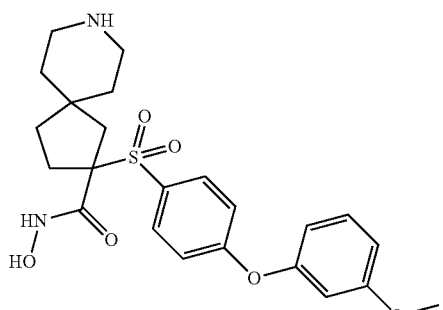
1-69
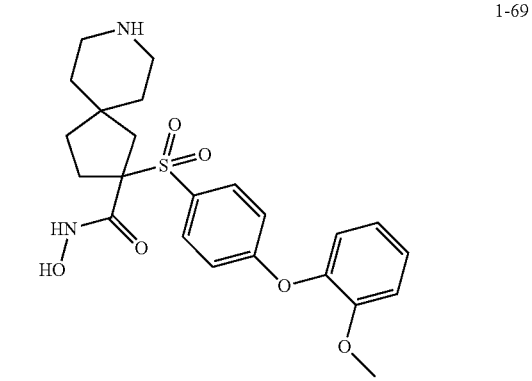
1-70
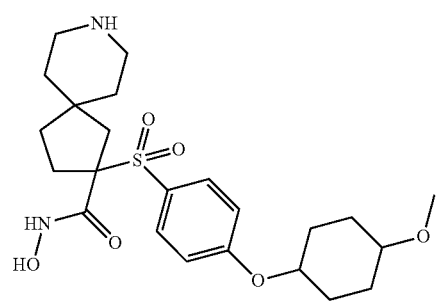
1-71
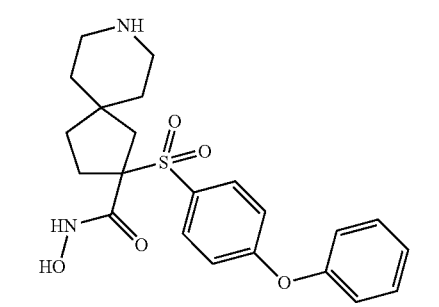
1-72
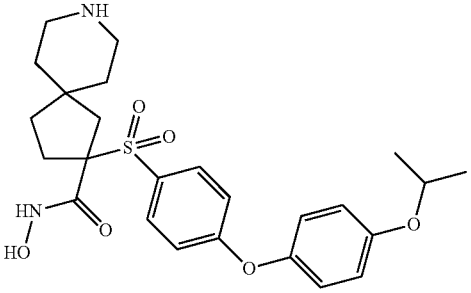

1-73 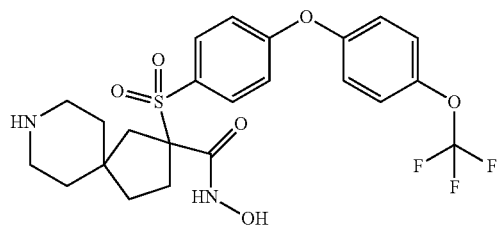
1-74 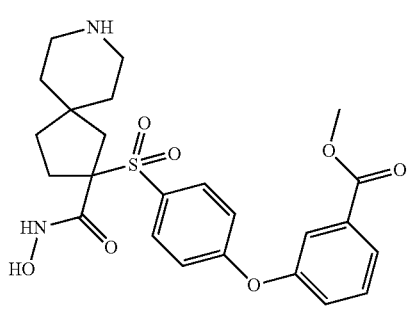
1-75 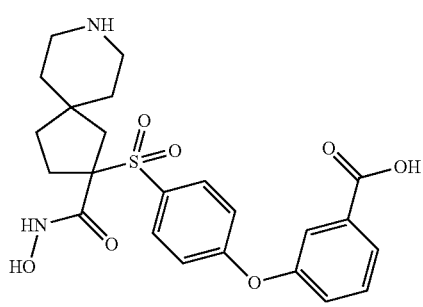
1-76 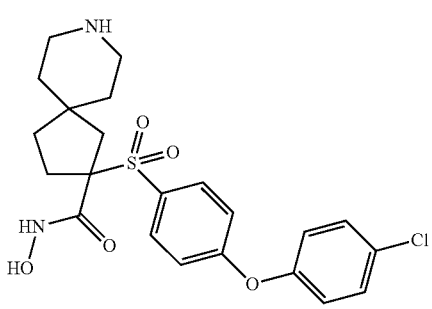
1-77 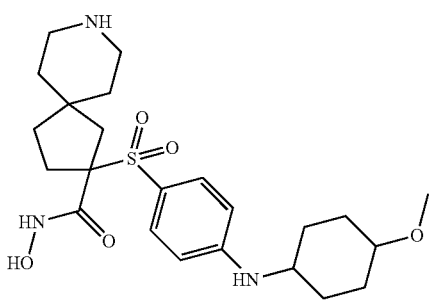
1-78 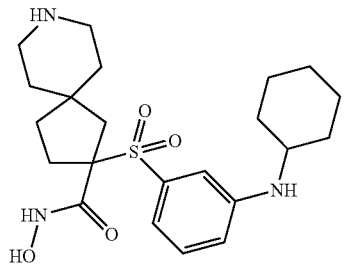
1-79 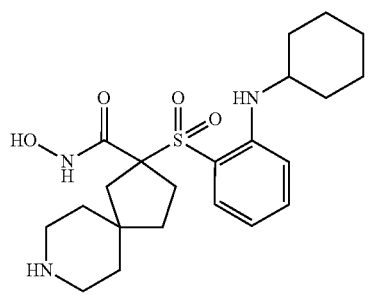
1-80 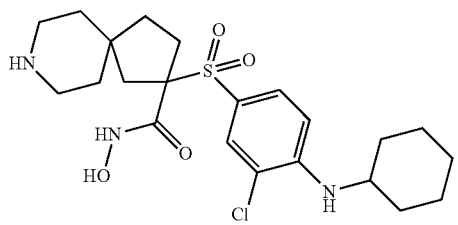
1-81 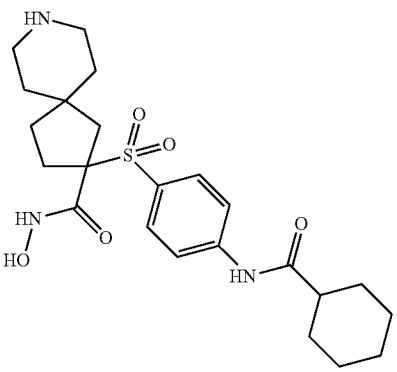
1-82 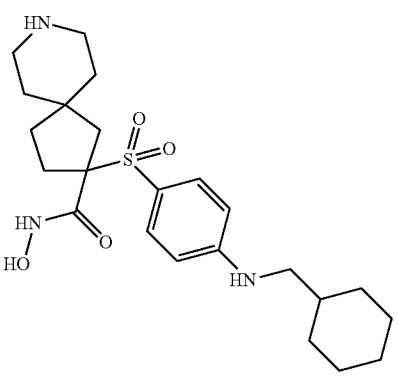

1-83
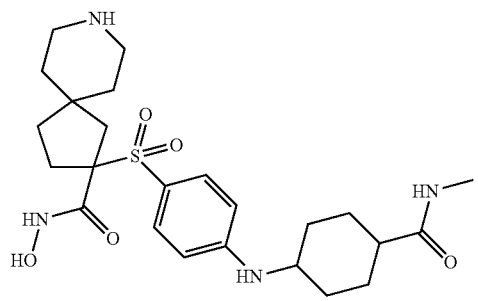
1-84
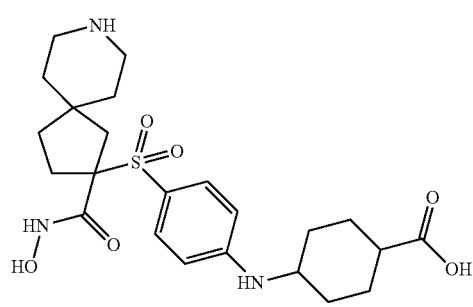
1-85
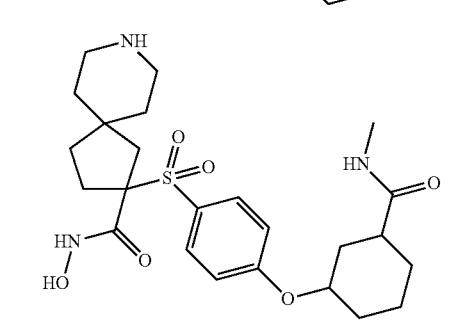
1-86
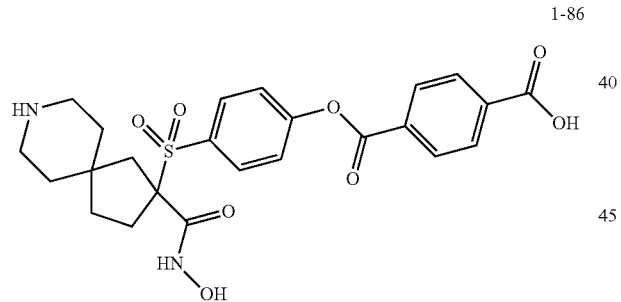
1-87
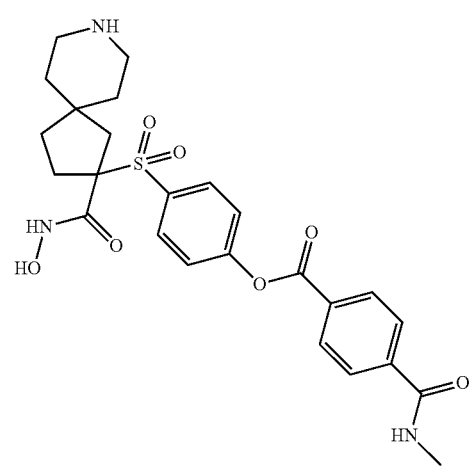
1-88
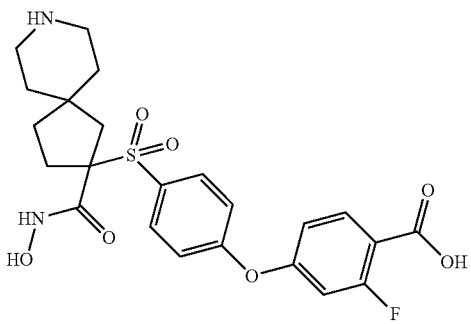
1-89
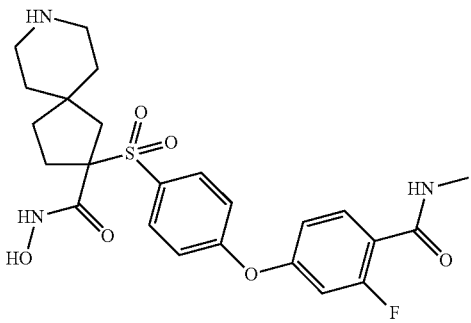
1-90
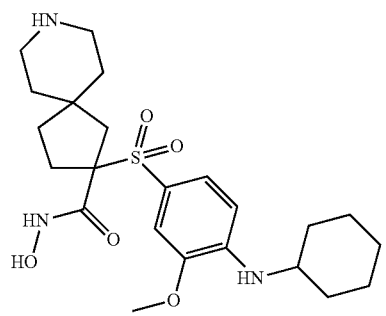
1-91
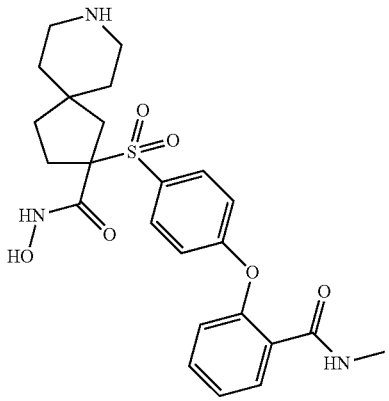

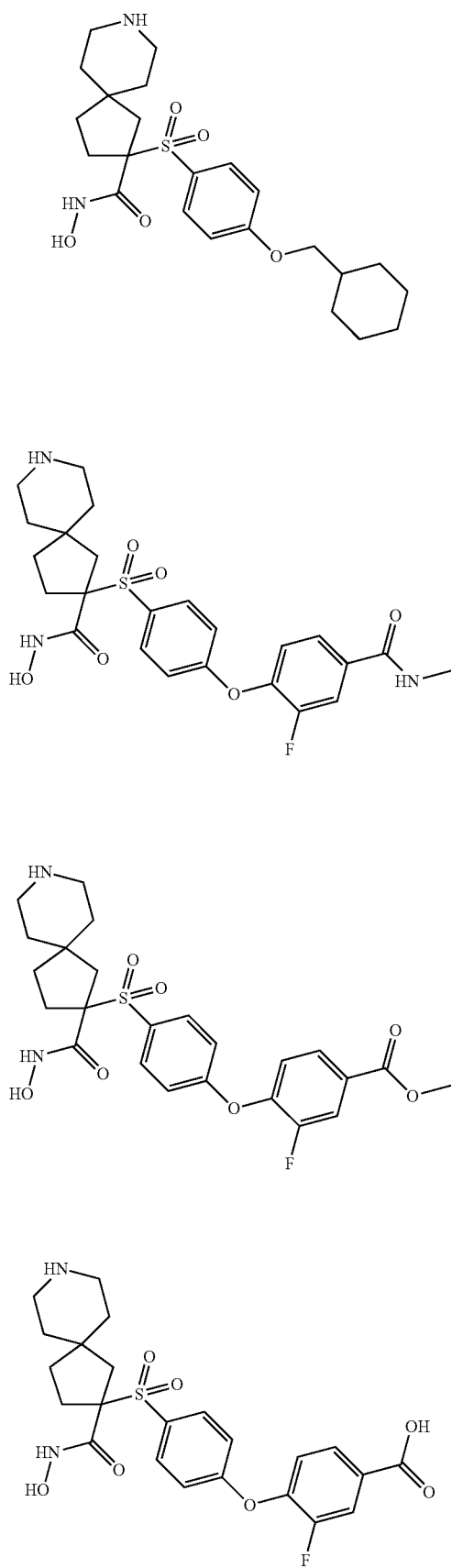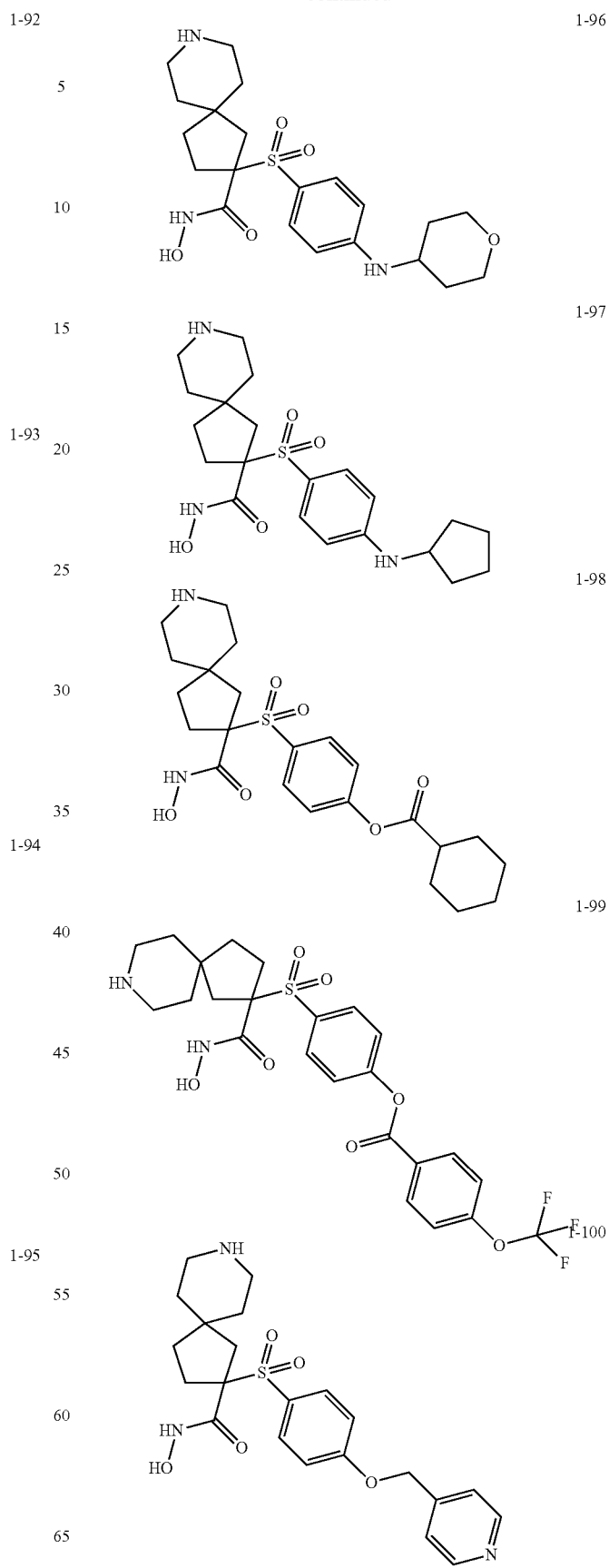

1-101 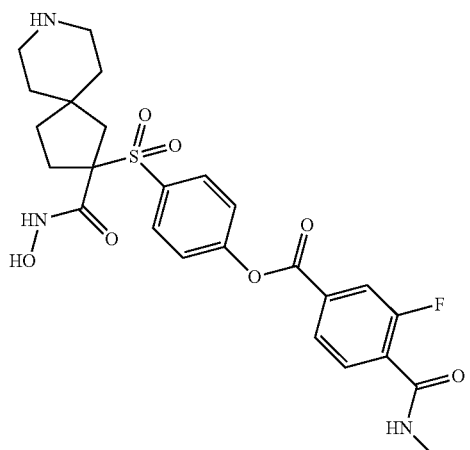
1-102 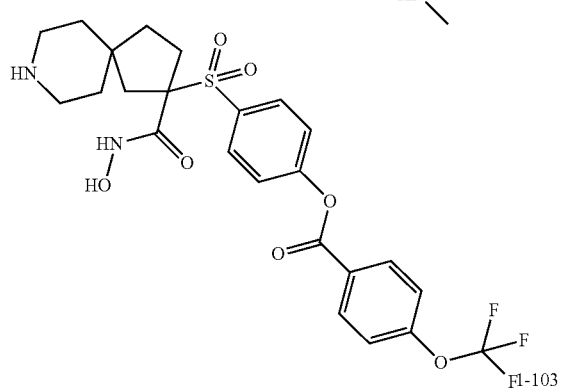
1-103 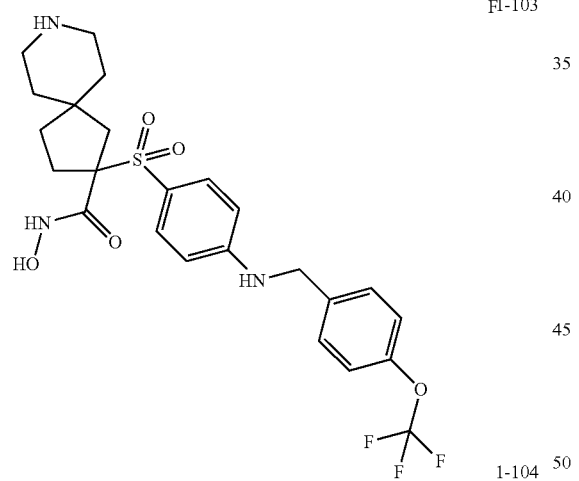
1-104 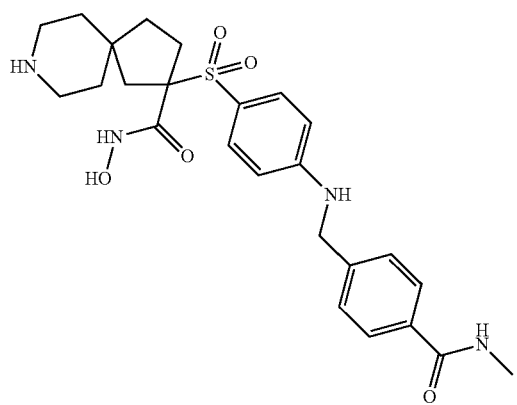
1-105 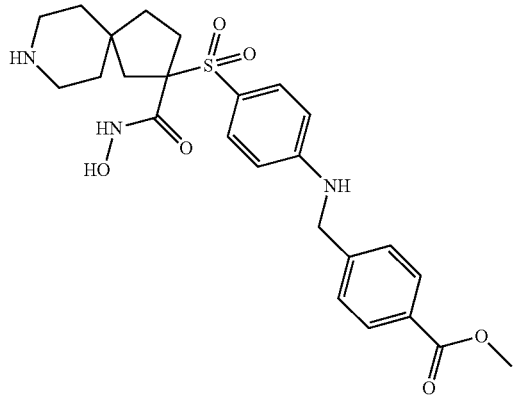
1-106 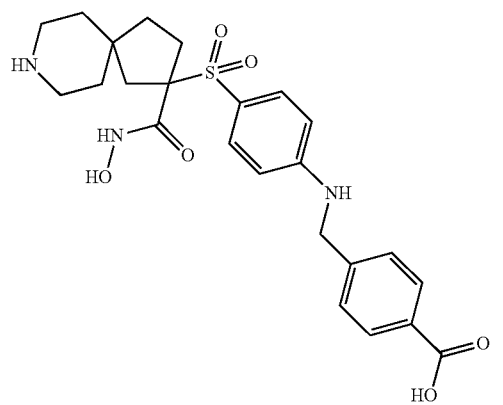
1-107 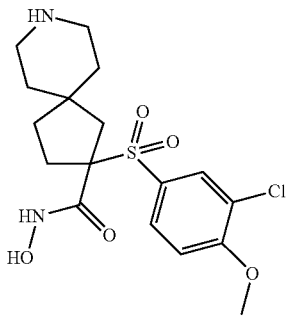
1-108 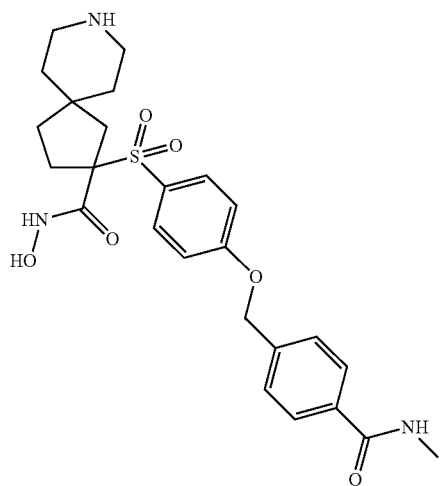

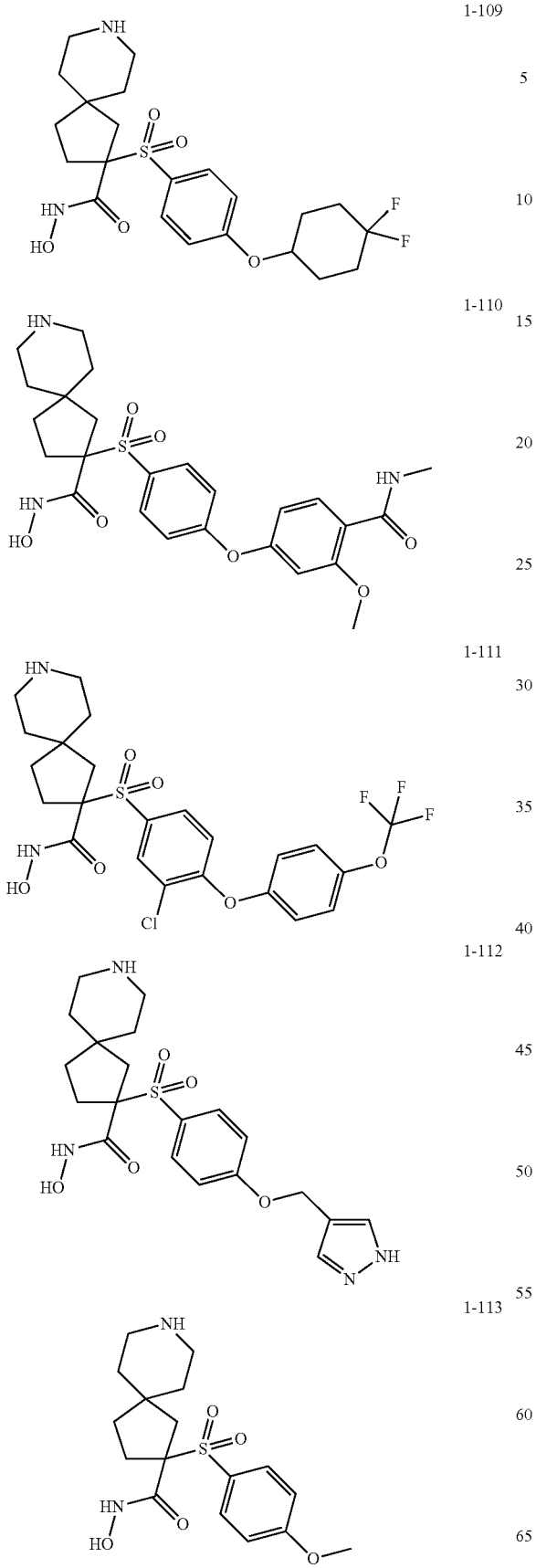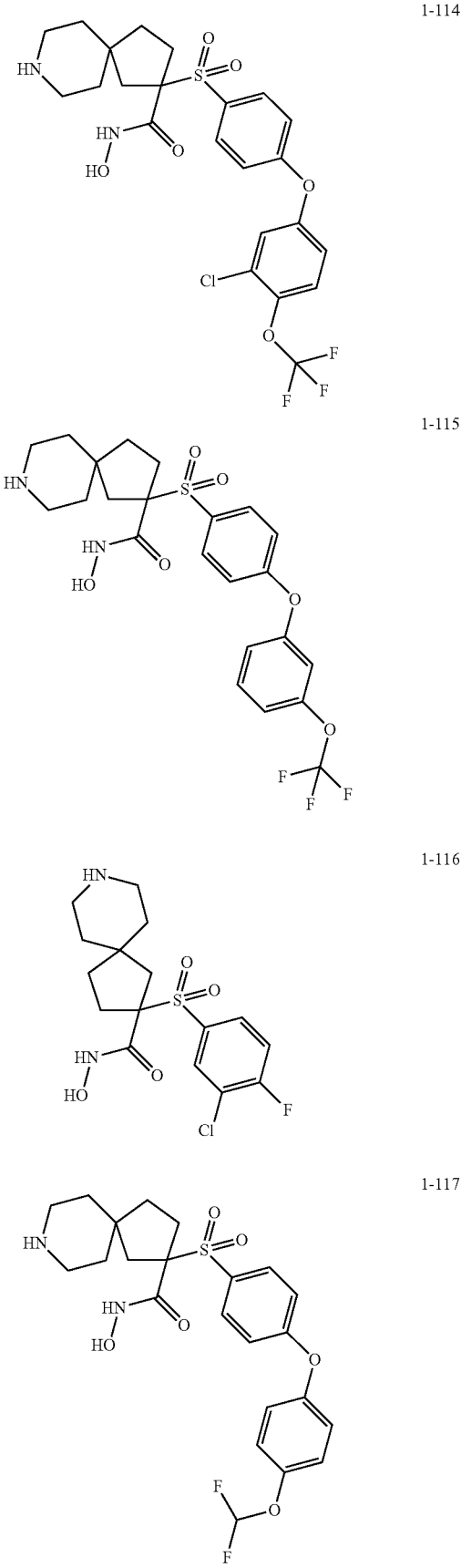

1-118
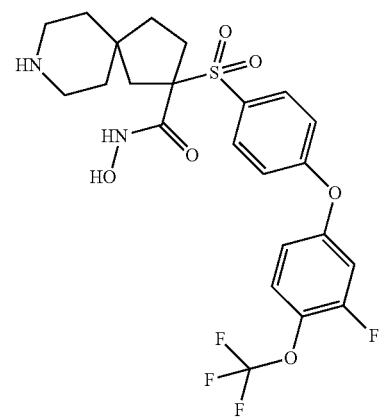
1-119
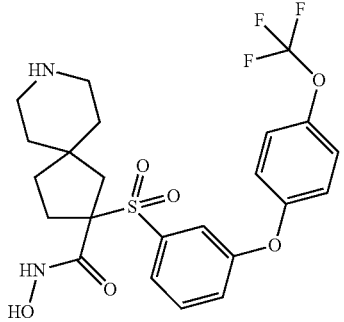
1-120
1-121
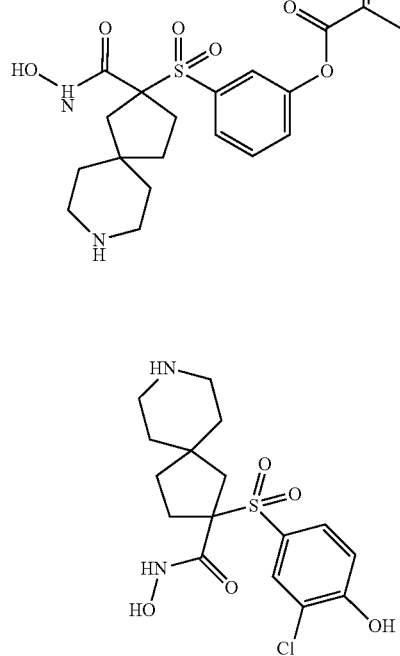
1-122
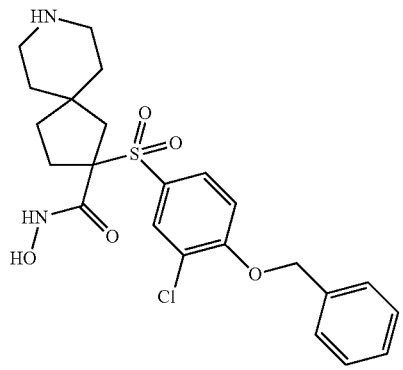
1-123
1-124
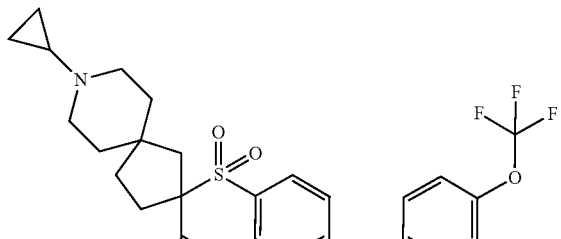
1-125
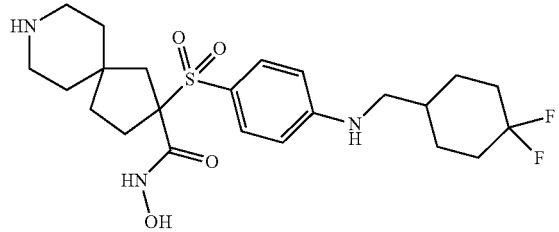
1-126
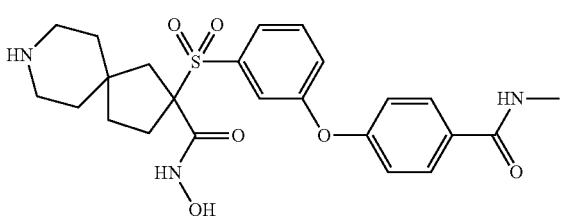

1-127
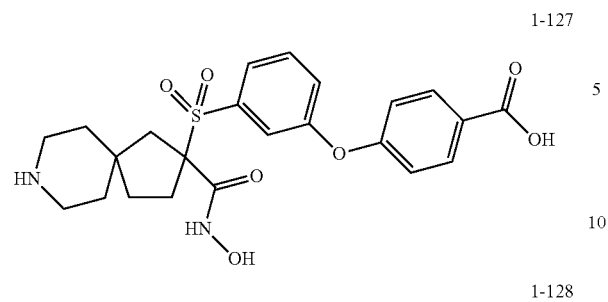
1-128
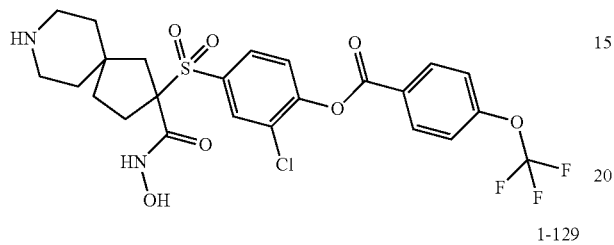
1-129
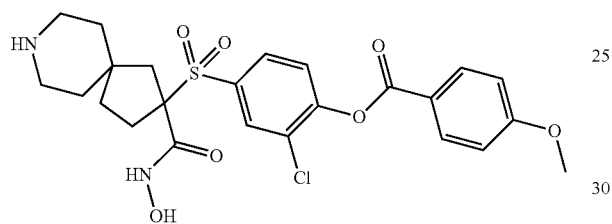
1-130
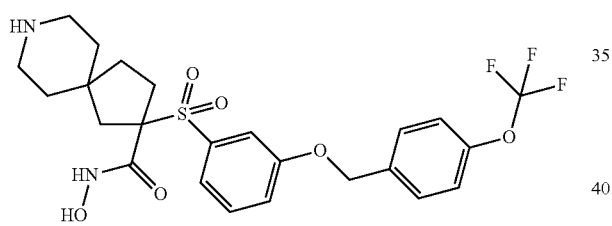
1-131
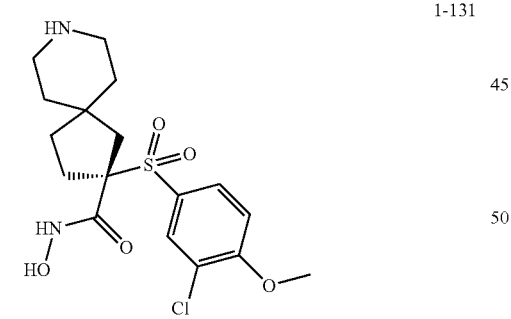
1-132
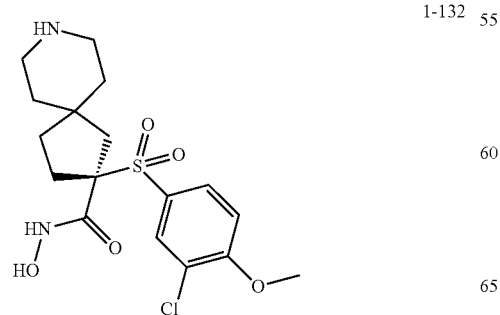
1-133
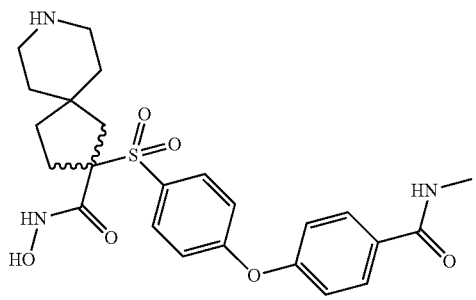
Isomer A*
1-134
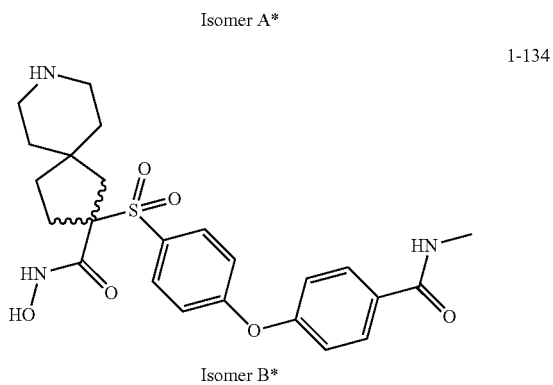
Isomer B*
1-135
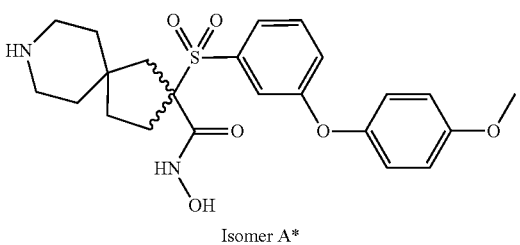
Isomer A*
1-136
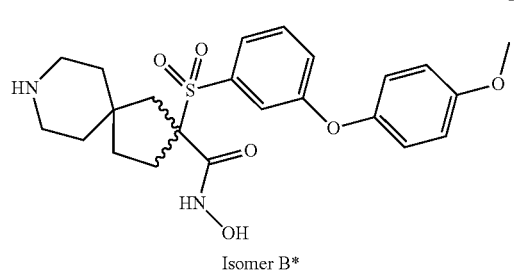
Isomer B*
1-137
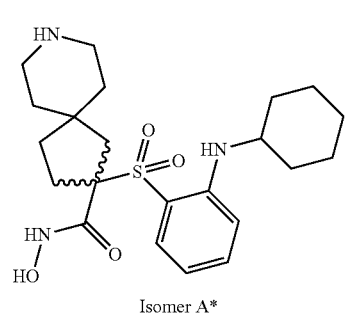
Isomer A*

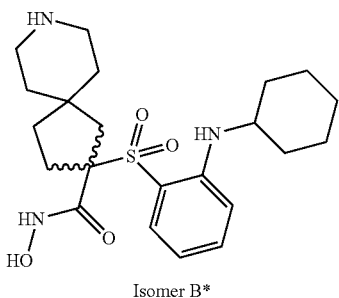

1-138

Isomer B*

Generally, compounds of formula (I) as defined above may be obtained by reacting a compound of formula (III)

*Regarding these compounds, no attempt has been made to identify the absolute configurations. However, in the examples it is clearly indicated which of the two isomers is concerned in relative terms by differentiating unambiguously between their physical and/or spectroscopic properties.

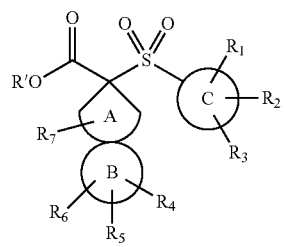

(III)

with a hydroxylamine of formula RO—NH$_2$ (IV), wherein A, B, C, R$_1$-R$_7$ are as previously defined; R' is H; and R is an hydroxamic acid protective group, more particularly an hydroxamic acid protective group selected from the group consisting of tetrahydro-2H-pyran-2-yloxy (THP), benzyl, 1-naphthylmethyl and dimethyloxybenzyl (DMB), to give a compound of formula (II)

(II)

and subsequently removing the protective group of the hydroxamic acid to give a compound of formula (I).

The first conversion can be carried out in the presence of an activating agent such as 1-ethyl-3-(3-dimethylaminopropyl)carbodiimide hydrochloride (EDC.HCl) and Hydroxybenzotriazole (HOBt), preferably in the presence of a base, such as N-methylmorpholine (NMM), in a suitable solvent, such as dichloromethane, chloroform or dimethylformamide, at a temperature comprised from room temperature to the temperature of the boiling point of the solvent, preferably at room temperature.

The removal of the protective group of the hydroxamic acid is carried out by standard methods well-known in the art as described for example in T. W. Green and P. G. M. Wuts, Protective Groups in Organic Chemistry (Wiley, 3rd ed. 1999, Chapter 2, pp. 17-200). Representative hydroxy protective groups include those where the hydroxy group is either acylated or alkylated such as benzyl, and trityl ethers as well as alkyl ethers, tetrahydropyranyl ethers, trialkylsilyl ethers and allyl ethers. For example, the hydroxamic acid protective group is tetrahydro-2H-pyran-2-yloxy (THP), benzyl, 1-naphthylmethyl or dimethyloxybenzyl (DMB). When the hydroxamic acid protective group is THP, the deprotection is carried out in acidic medium, for example with HCl, in a suitable solvent such as dioxane.

Intermediate compounds of formula (II), wherein A, B, C, R$_1$-R$_7$ and R are as previously defined, also form part of the invention.

Compounds of formula (III) wherein R' is H can be obtained by removing the protective group of a compound of formula (III) wherein R' is a carboxy protective group by standard methods well-known in the art as described for example in T. W. Green and P. G. M. Wuts, Protective Groups in Organic Chemistry (Wiley, 3rd ed. 1999, Chapter 5, pp. 369-451). Representative carboxy protective groups include alkyl, aryl or benzyl esters, sylil esters, amides or hydrazides. For example, the carboxy protective group is (C$_1$-C$_6$)alkyl, benzyl, p-methoxyphenyl, trimethylsilyl, or [2-(Trimethylsilyl)-ethoxy]methyl (SEM). When the carboxy protective group is (C$_1$-C$_6$)alkyl, the deprotection is carried out in basic medium, for example with LiOH in a suitable solvent such as tetrahydrofuran-methanol.

Intermediate compounds of formula (III) wherein A, B, C, R$_1$-R$_7$ are as previously defined and R' is H or a carboxy protective group, more particularly a carboxy protective group selected from the group consisting of (C$_1$-C$_6$)alkyl, benzyl, p-methoxyphenyl, trimethylsilyl and [2-(Trimethylsilyl)ethoxy]methyl (SEM) form also part of the invention, with the proviso that compound (III) is other than 7-methoxycarbonyl-7-phenylsulphonyl-2-oxaspiro[2.4]heptane and (2S*,4R*)-2-Phenylsulfonyl-4-iodomethyl-6,11-dioxaspiro[4.6]undecane-2-carboxylic acid methyl ester, form also part of the invention. These compounds are cited in D. Bouyssi et al., "Rearrangement of oxaspiroheptanes to cyclohexanones mediated by lithium iodide", Synlett 2000, vol. 5, pp. 749-751 and Osamu Kitagawa et al., "Stereoselective Iodine Atom Transfer [3+2] Cycloaddition Reaction with Alkenes Using Unsymmetrical Allylated Active Methine Radicals", The Journal of Organic Chemistry 2004, vol. 69, pp. 2607-2610, respectively, which describe only a synthetic process without describing any therapeutical application. Given that the chemical structure of intermediate compounds of formula (II) and formula (III) coincides largely with the chemical structure of the final compounds of formula (I), the particular embodiments defined above for the compounds of formula (I) regarding the variables A, B, C, and R$_1$-R$_7$ are also particular embodiments of the intermediate compounds of formula (II) and formula (III).

Compounds of formula (III) can be generally obtained by coupling a compound of formula (V) with a compound of formula (VI):

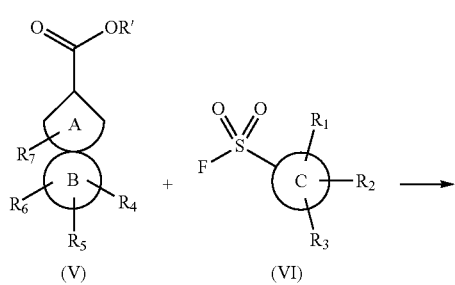

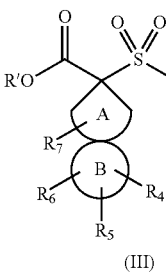

wherein A, B, C, $R_1$-$R_7$ are as previously defined and R' is carboxy protective group. This conversion is carried out in the presence of a base such as lithium diisopropylamide (LDA), in a suitable solvent such as tetrahydrofuran, and at a suitable temperature, preferably −78° C.

Additionally, compounds of formula (I), wherein $R^1$ is Q-$Cy^2$, wherein Q is O, S, SO or $SO_2$ and $Cy^2$ is as defined above (i.e. compound of formula (Ia)) may be obtained in general as shown in the following scheme:

A compound of formula (V), wherein A, B, $R_4$-$R_7$ are as previously defined and R' is carboxy protective group, is reacted as described above with a compound of formula (VIa) wherein C, $R_2$ and $R_3$ are as previously defined, to give a compound of formula (IIIa), which is deprotected to give the carboxylic acid of formula (IIIb) and subsequently reacted with a compound of formula (IV) as already described to give compound (IIa).

Compound of formula (IIa) is reacted with a compound of formula H-Q'-$Cy^2$ (VII), wherein Q' is O or S, and $Cy^2$ is as defined above, to give a compound of formula (IIb). This reaction is carried out in the presence of a base, such as cesium carbonate, optionally in a suitable solvent or without solvent, and preferably heating.

Further, a compound of formula (IIb) wherein Q is S can be oxidized to a compound of formula (IIb) wherein Q is SO or $SO_2$ in the presence of an oxidizing agent, such as m-chloroperbenzoic acid, in a suitable solvent, such as dichlorormethane, and preferably at room temperature.

Deprotection of a compound of formula (IIb) yields a compound of formula (Ia) as defined above.

Additionally, compounds of formula (I), wherein $R^1$ is Q-alk, Q is O or S, and alk is saturated or unsaturated —($C_1$-$C_{12}$)alkyl optionally substituted (i.e. compound of formula (Ib)) may be obtained in general as shown in the following scheme:

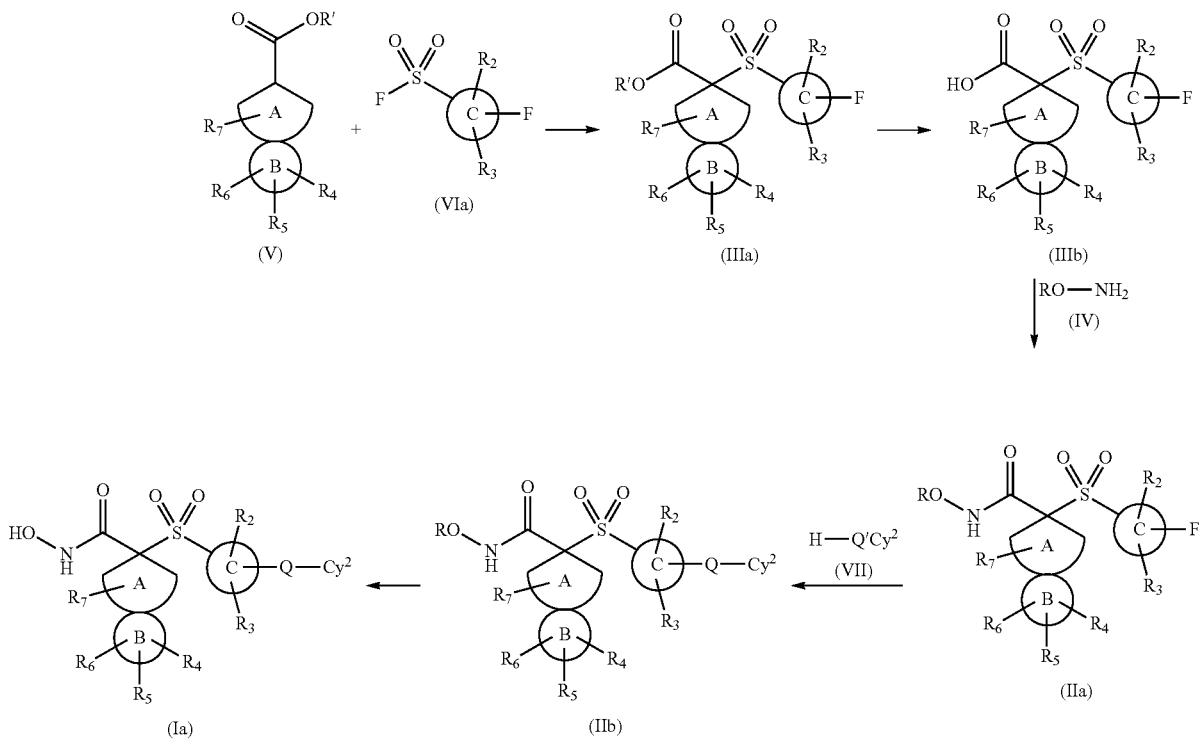

Scheme 1

Scheme 2

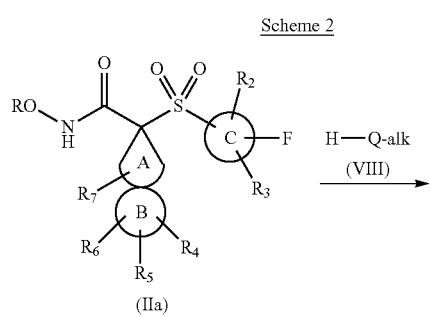

Thus, a compound of formula (IIa) can be reacted with a compound of formula H-Q-alk (VIII) in the presence of a base, such as NaH, optionally in a suitable solvent or without solvent, and preferably heating. After removal of the protective group in the resulting compound of formula (IIc), compound of formula (Ib) is obtained.

Compounds of formula (I), wherein $R^1$ is —$NR^bR^{a'}$, $R^b$ is saturated or unsaturated —$(C_1-C_{12})$alkyl optionally substituted and $R^{a'}$ is H or saturated or unsaturated —$(C_1-C_{12})$alkyl optionally substituted (i.e. compound of formula (Ic)) may be obtained in general as shown in the following scheme:

Scheme 3

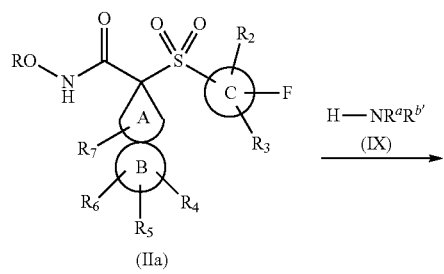

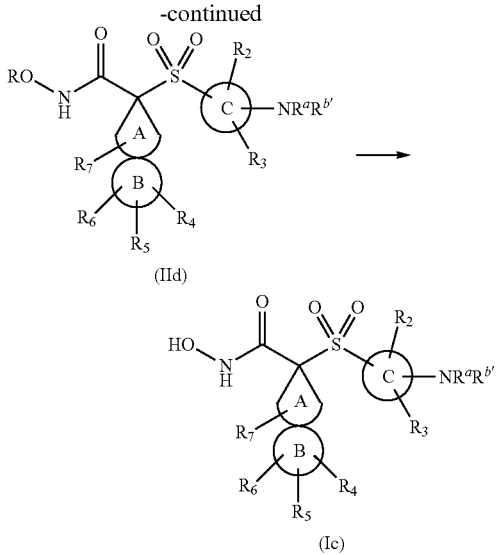

Thus, a compound of formula (IIa) can be reacted with a compound of formula H—$NR^bR^{a'}$ (IX), optionally in a suitable solvent or without solvent, and preferably heating. After removal of the protective group in the resulting compound of formula (IId), compound of formula (Ic) is obtained.

Compounds of formula (I), wherein $R^1$ is —$NCy^2R^{a'}$ and $Cy^2$ is an optionally substituted aromatic, heteroaromatic or aliphatic ring (i.e. compound of formula (Id)) may be obtained in general as shown in the following scheme:

Scheme 4

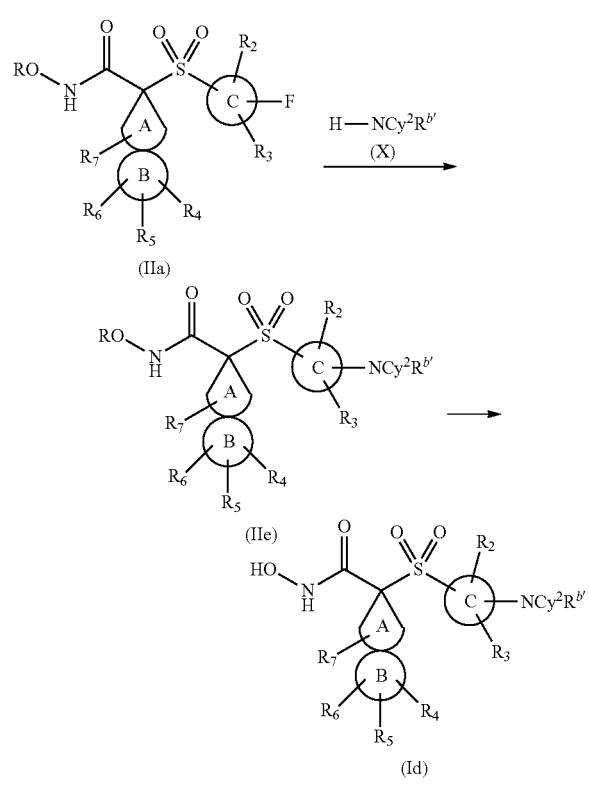

Thus, a compound of formula (IIa) can be reacted with a compound of formula H—$NCy^2R^{a'}$ (X), optionally in a suitable solvent or without solvent, and preferably heating. After removal of the protective group in the resulting compound of formula (IIe), compound of formula (Id) is obtained.

Compounds of formula (I), wherein $R^1$ is —$NR^bC(Y)R^{a'}$, —$NR^bC(Y)OR^{a'}$, —$NR^bC(Y)NR^bR^a$, —$NR^bS(O)_2R^{a'}$, —$NR^bSO_2NR^bR^{a'}$ (i.e. compound of formula (Ie)) may be obtained from a compound of formula (IIg), which can be prepared as shown in the following scheme:

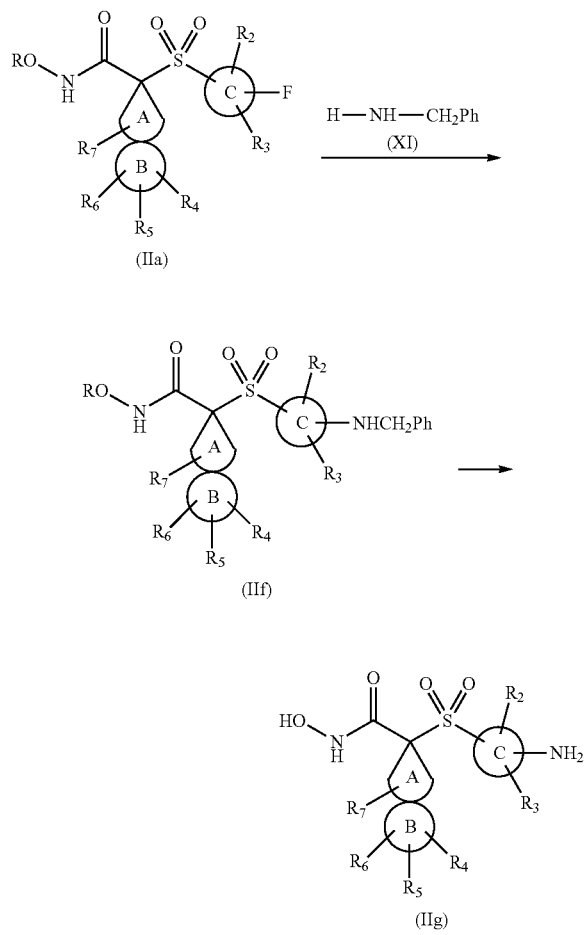

In a first step, compound of formula (IIa) is reacted with benzylamine, preferably heating to give a compound of formula (IIf) which can be hydrogenated in the presence of Pd/C to give a compound of formula (IIg). This compound can be reacted for example with an acyl halide in the presence of a base, such as triethylamine, in a suitable solvent, such as tetrahydrofuran, at a temperature comprised from room temperature to the reflux temperature of the solvent, to give an amide; or with an isocyanate to give a urea.

Compounds of formula (I), wherein $R^1$ is —$OC(Y)R^{a'}$ (i.e. compound of formula (If)) may be obtained from a compound of formula (IIi), which can be prepared as shown in the following scheme:

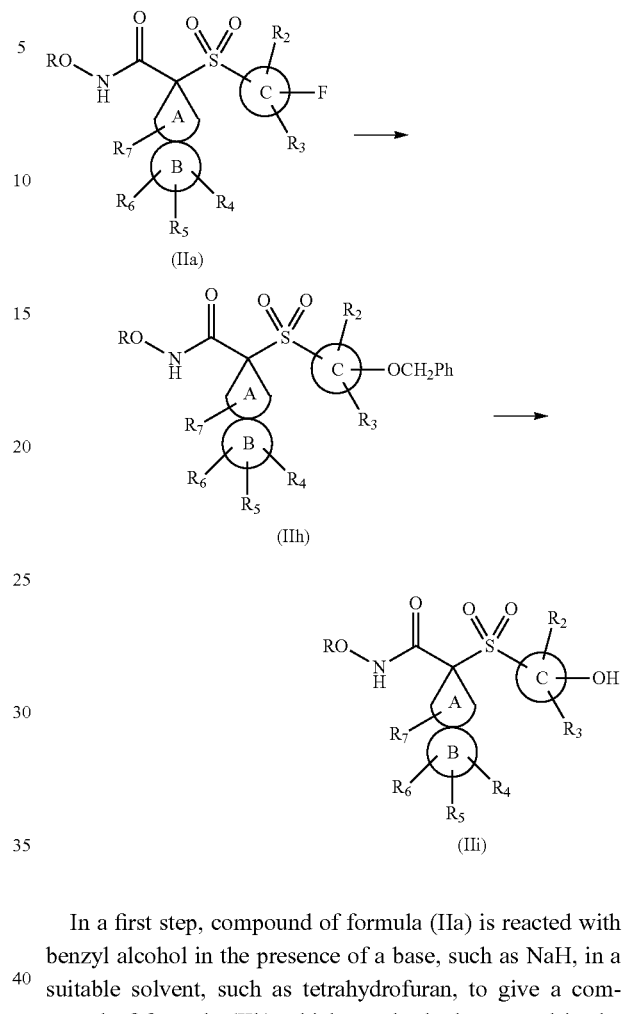

In a first step, compound of formula (IIa) is reacted with benzyl alcohol in the presence of a base, such as NaH, in a suitable solvent, such as tetrahydrofuran, to give a compound of formula (IIh) which can be hydrogenated in the presence of Pd/C to give a compound of formula (IIi). This compound can be reacted for example with an acyl halide in the presence of a base, such as triethylamine, in a suitable solvent, preferably at room temperature to give an ester.

Compounds of formula (I), wherein $R^1$ is $R^a$ (i.e. compound of formula (Ig)) may be obtained from a compound of formula (IIk), which can be prepared as shown in the following scheme:

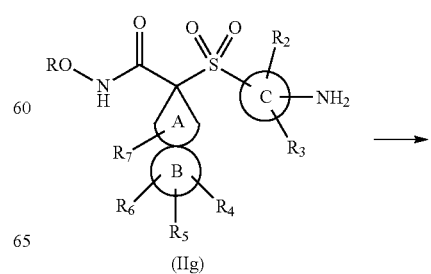

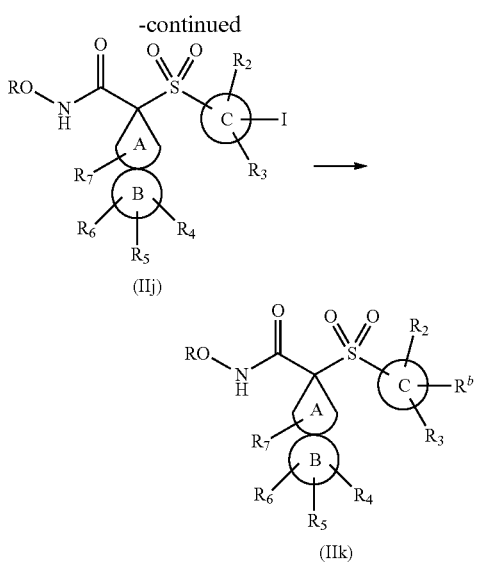

In a first step, compound of formula (IIg) is reacted with potassium iodide and $NaNO_2$ in a suitable solvent, such as acetonitrile and then an acid, such as concentrated HCl, is added to give a compound of formula (IIj). This compound can be reacted for example with boronic acid derivatives in the presence of a palladium catalyst (Suzuki coupling) to give a compound of formula (IIk).

The same type of reactions shown above for $R_1$ can be applied to $R_2$-$R_7$.

Alternatively, the reactions described above can be carried out in a different order. Thus, the reactions carried out on compounds of formula (II) (i.e. on the protected hydroxamic acid) can be carried out on compounds of formula (III) (i.e. the carboxylic ester), and can be deprotected to give the corresponding carboxylic acids, which can be converted to the compounds of formula (I) as described above.

The compounds of formulas (V) to (XI) are commercially available or can be obtained by conventional synthetic processes.

The present invention also relates to a pharmaceutical or veterinary composition comprising an effective amount of a compound of formula (I) as defined above, or a pharmaceutically or veterinary acceptable salt thereof, or any stereoisomer either of the compound of formula (I) or of its pharmaceutically or veterinary acceptable salt, together with pharmaceutically or veterinary acceptable excipients or carriers.

The expression "effective amount" as used herein, refers to the amount of a compound that, when administered, is sufficient to prevent development of, or alleviate to some extent, one or more of the symptoms of the disease which is addressed. The specific dose of the compound of the invention to obtain a therapeutic benefit may vary depending on the particular circumstances of the individual patient including, among others, the size, weight, age and sex of the patient, the nature and stage of the disease, the aggressiveness of the disease, and the route of administration. For example, a dose of from about 0.01 to about 300 mg/kg may be used.

The expression "pharmaceutically or veterinary acceptable excipients or carriers" refers to pharmaceutically or veterinary acceptable materials, compositions or vehicles. Each component must be pharmaceutically or veterinary acceptable in the sense of being compatible with the other ingredients of the pharmaceutical or veterinary composition. It must also be suitable for use in contact with the tissue or organ of humans and animals without excessive toxicity, irritation, allergic response, immunogenicity or other problems or complications commensurate with a reasonable benefit/risk ratio.

The election of the pharmaceutical or veterinary formulation will depend upon the nature of the active compound and its route of administration. Any route of administration may be used, for example oral, parenteral and topical administration.

For example, the pharmaceutical or veterinary composition may be formulated for oral administration and may contain one or more physiologically compatible carriers or excipients, in solid or liquid form. These preparations may contain conventional ingredients such as binding agents, fillers, lubricants, and acceptable wetting agents.

The pharmaceutical or veterinary composition may be formulated for parenteral administration in combination with conventional injectable liquid carriers, such as water or suitable alcohols. Conventional pharmaceutical or veterinary excipients for injection, such as stabilizing agents, solubilizing agents, and buffers, may be included in such compositions. These pharmaceutical or veterinary compositions may be injected intramuscularly, intraperitoneally, or intravenously.

The pharmaceutical or veterinary composition may be formulated for topical administration. Formulations include creams, lotions, gels, powders, solutions and patches wherein the compound is dispersed or dissolved in suitable excipients. The topical compositions of the invention may be administered by means of a carrier material, which can be a solid support. Thus, it also forms part of the invention a topical composition comprising a carrier material, which can be a solid support. Illustrative, non-limiting examples of solid supports include intelligent textiles, dressings, coatings, sponges, band-aids, sanitary pads, compresses, plasters, etc. The manufacture of such compositions can be obtained by conventional methods, for example, by mixing the combinations of the invention and the material carrier.

The pharmaceutical or veterinary compositions may be in any form, including, among others, tablets, pellets, capsules, aqueous or oily solutions, suspensions, emulsions, or dry powdered forms suitable for reconstitution with water or other suitable liquid medium before use, for immediate or retarded release.

The appropriate excipients and/or carriers, and their amounts, can readily be determined by those skilled in the art according to the type of formulation being prepared.

The compounds of the present invention are useful as antihemorrhagic and antifibrinolytic agents and can be used in a broad range of therapeutic applications. In surgery, antifibrinolytic agents, in addition to reducing post-operative hemorrhage, can be an alternative to blood transfusion and other hemoderivatives for example in heart, liver and orthopedic surgery, and also in the setting of oncologic surgery in organs rich in fibrinolysis activators (prostate, uterus). In trauma patients antifibrinolytic agents can reduce all-cause mortality and death due to bleeding. Further, the antifibrinolytic agents of the invention can also be used to control bleeding in trombolytic therapy, e.g. in cases of acute heart attack and ischemic stroke, and major or intracraneal hemorrhages. Moreover, the antifibrinolytic agents of the invention are useful in the treatment of local hemorrhages, e.g. after teeth extraction, in particular in patients with congenital coagulopathies, such as hemophilia, or patients with diabetes; in the treatment of menorrhage in women associated with congenital or acquired coagulopathies, as well as in post-partum haemorrhage, and in the treatment of hemorrhages of gastrointestinal and urologic origin, including prostatectomy.

Throughout the description and claims the word "comprise" and variations of thereof, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples are provided by way of illustration, and they are not intended to be limiting of the present invention. Furthermore, the present invention covers all possible combinations of particular and preferred embodiments described herein.

EXAMPLES

General Procedure for Prep-HPLC Purification Method:

The HPLC measurement was performed using Gilson 281 from 233 pump (binary), an autosampler, and a UV detector. The fractions was detected by LC-MS. The MS detector was configured with an electrospray ionization source. The source temperature was maintained at 300-350° C.

Method 1

Reverse phase HPLC was carried out on Luna C18 (100×30 mm; 4 um). Solvent A: water with 0.075% trifluoroacetic acid; Solvent B: acetonitrile with 0.075% trifluoroacetic acid. Gradient: At room temperature, 20% of B to 40% of B within 6 min at 25 mL/min; then 40% B at 25 mL/min over 2 min, UV detector.

The following abbreviations have been used in the examples:
Boc: tert-butoxycarbonyl
DCM: dichloromethane
DMF: dimethylformamide
Et$_3$N: triethylamine
TLC: Thin Layer Chromatography
PE: Petroleum ether
AE/EtOAc: ethyl acetate
ACN: acetonitrile
r.t.: room temperature
Rt: retention time
THF: tetrahydrofuran
LDA Lithium diisopropylamide
EDC.HCl: 1-ethyl-3-(3-dimethylaminopropyl)carbodiimide hydrochloride
HOBt: Hydroxybenzotriazole
THP—O—NH$_2$: N-(tetrahydro-2H-pyran-2-yloxy)amine
MeOH: methanol
NMM: N-Methylmorpholine
m-CPBA: m-chloroperbenzoic acid
DCM: dichloromethane
DMSO: dimethylsulfoxide
Synthetic Route 1a

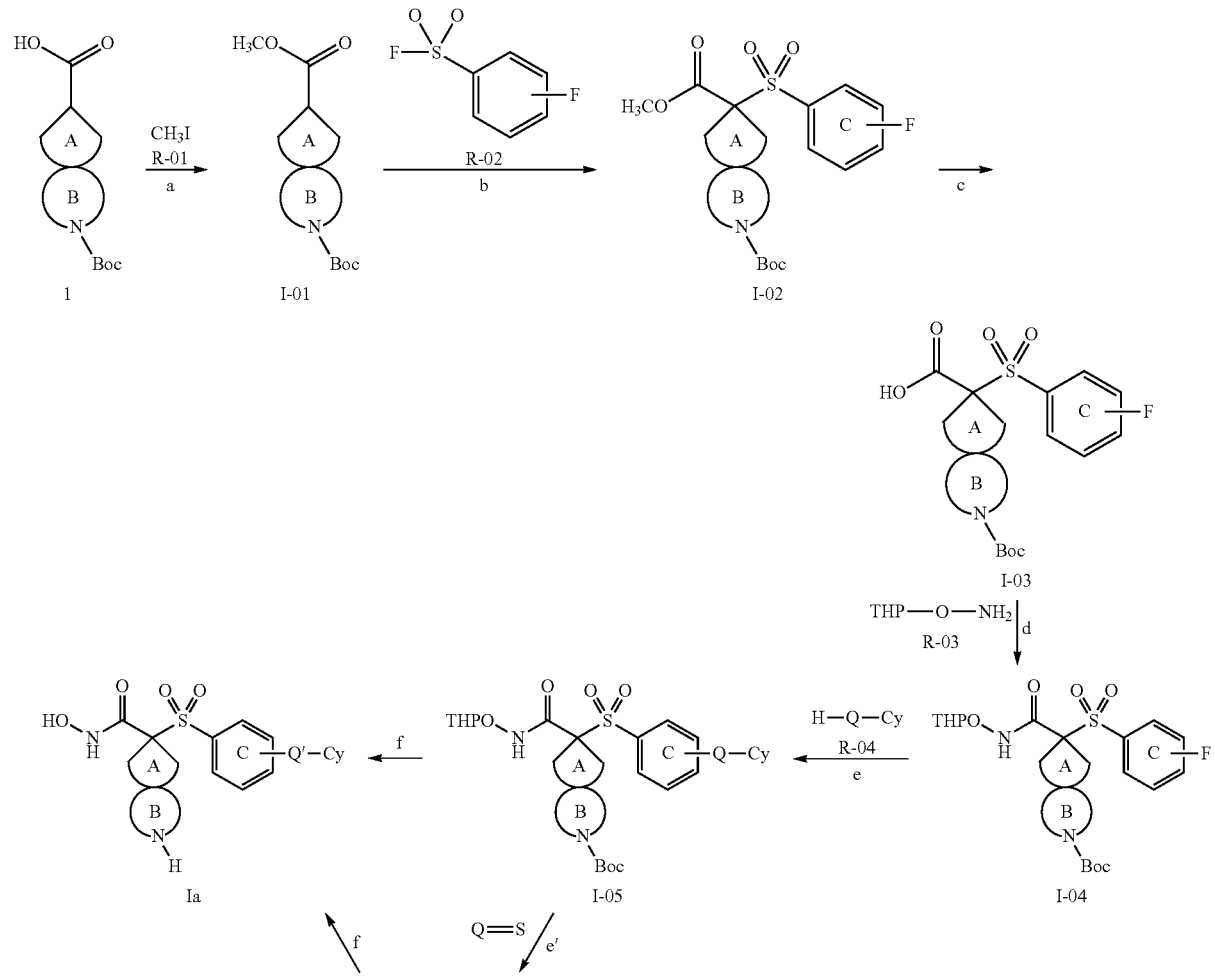

-continued

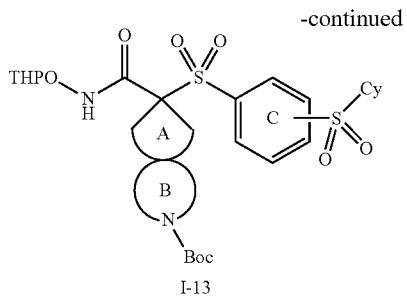

I-13

Conditions: a. K₂CO₃ (2 eq), CH₃I (1.5 eq) IN DMF, r.t.; b. LDA (1.25 M) in THF, 1 hour at -78° C.; then, R-02 (2 eq), 1 hour at -78° C.; c. LiOH·H₂O (10 eq) in THF/MeOH/H₂O (3/3/2), r.t.; d. EDC·HCl (2 eq), HOBt (2 eq), THP—O—NH₂ (1.5 eq), NMM (3 eq) in DMF, r.t.; e. R-04 (1.5-3 eq), Cs₂CO₃ (2-3 eq), 12 hours at 90° C.; e'. m-CPBA (4 eq) in DCM, r.t. (Q═S to Q'═SO₂); f. -HCl/Dioxane, r.t. for 1 hour.

In the scheme above Q is O or S, Q' is Q or SO₂ and Cy is phenyl or a 5- to 6-membered heteroaryl and can be optionally substituted.

Preparation of Intermediate I-01a 8-tert-butoxycarbonyl-8-azaspiro[4.5]decane-3-carboxylic Acid Methyl Ester To a solution of 8-tert-butoxycarbonyl-8-azaspiro[4.5]decane-3-carboxylic acid (20 g, 0.071 mol), commercially available from Wuxi Apptec, in DMF (200 mL) was added K₂CO₃ (18.59 g, 2 eq), then compound CH₃I (14.34 g, 1.5 eq) was added dropwise. The reaction mixture was stirred at room temperature for 2 h.

After TLC (PE/AE 5:1) showed the starting material was consumed, the mixture was quenched with water and extracted with EtOAc, the organic layer was washed with brine, dried over anhydrous Na₂SO₄, concentrated to give the crude compound 8-tert-butoxycarbonyl-8-azaspiro[4.5]decane-3-carboxylic acid methyl ester (20.38 g, 97.09%) as a pale yellow oil which was used for the next step without further purification. ESI-MS (M+1): 298 calc. for $C_{16}H_{27}NO_4$.

Preparation of Reagent R-02a

4-Fluorobenzenesulfonyl fluoride

To a solution of compound 4-Fluorobenzenesulfonyl chloride (50 g, 0.256 mol) in ACN (500 mL) was added KF (74.36 g, 5 eq) and 18-crown-6 (2 g) at r.t., then the mixture was stirred at r.t. overnight. The mixture was detected by LC-MS, then saturated aqueous NaHCO₃ was added and the mixture was extracted with EtOAc, the organic layer was washed with saturated aqueous NaHCO₃, brine, dried over anhydrous Na₂SO₄, concentrated to give the crude compound 4-Fluorobenzenesulfonyl fluoride (46.70 g) as pale yellow oil which was used for the next step without further purification. ESI-MS (M+1): 179 calc. for $C_6H_4F_2O_2S$.

Preparation of Intermediate I-02a 8-tert-butoxycarbonyl-3-(4-fluorophenylsulfonyl)-8-azaspiro[4.5]decane-3-carboxylic Acid Methyl Ester To a solution of compound I-01a (18.38 g, 0.062 mol) in THF (200 mL) was added LDA (102 mL, 1.25 M) at −78° C. After stirring at −78° C. for 1 h, the compound 4-Fluorobenzenesulfonyl fluoride (22.23 g, 2 eq) was added to the solution, the reaction was stirred at −78° C. for 1 hour, and then the mixture was stirred at r.t. overnight. After TLC (PE/AE 5:1) showed the starting material was consumed, the mixture was quenched with aqueous NH₄Cl and extracted with EtOAc, the organic layer was washed with brine, dried over anhydrous Na₂SO₄, concentrated to give the crude product which was purified by column chromatography (eluting with EA/PE=100:1 to 10:1) to give pure compound I-02a (18.94 g, 67.03%) as a pale yellow oil. ESI-MS (M+1): 456 calc. for $C_{22}H_{30}FNO_6S$.

Preparation of Intermediate I-03a 8-tert-butoxycarbonyl-3-(4-fluorophenylsulfonyl)-8-azaspiro[4.5]decane-3-carboxylic Acid To a solution of compound I-02a (10 g, 0.022 mol) in THF/MeOH/H₂O (3/3/2, 80 mL) was added LiOH H₂O (9.23 g, 10 eq). The resulting mixture was stirred at r.t. for 4 h, after TLC (PE/AE 5:1) showed the staring materials were consumed completely, then the mixture was diluted with water and adjusted pH to 2-3 with 1N HCl and the mixture was extracted with EtOAc, washed with brine, dried over anhydrous Na₂SO₄, concentrated to give the crude product I-03a (9.60 g, 98.97%) as a pale yellow oil which was used in the next step. ESI-MS (M+1): 442 calc. for $C_{21}H_{28}FNO_6S$.

Preparation of Intermediate I-04a 8-tert-butoxycarbonyl-3-(4-fluorophenylsulfonyl)-N-(tetrahydro-2H-pyran-2-yloxy)-8-azaspiro[4.5]decane-3-carboxamide To a solution of compound I-03a (9.60 g, 0.022 mol) in DMF (100 mL) was added EDC.HCl (8.40 g, 2 eq), HOBt (5.85 g, 2 eq), THP—O—NH₂ (3.86 g, 1.5 eq), NMM (6.67 g, 3 eq) at r.t., then the mixture was stirred at room temperature overnight. The mixture was quenched with aqueous water and extracted with EtOAc, the organic layer was washed with brine, dried over anhydrous Na₂SO₄, concentrated to give the crude product which was purified by column chromatography (eluting with EA/PE=50:1 to 2:1) to give pure compound I-04a (9.0 g, 75.76%) as a pale yellow solid. ESI-MS (M+1): 541 calc. for $C_{26}H_{37}FN_2O_7S$.

Preparation of Intermediate I-05a 8-tert-butoxycarbonyl-3-[4-(4-methoxyphenoxy)Phenylsulfonyl]-Netrahydro-2H-pyran-2-yloxy)-8-azaspiro[4.5]decane-3-carboxamide To a solution of I-04a (200 mg, 0.37 mmol) in DMF (5 mL) was added p-methoxyphenol (69 mg, 1.5 eq)

and Cs$_2$CO$_3$ (241 mg, 2 eq), then the reaction mixture was stirred at 90° C. overnight. After TLC (PE/AE 2:1) showed the starting material was consumed, the mixture was quenched with water and extracted with EtOAc, the organic layer was washed with brine, dried over anhydrous Na$_2$SO$_4$, concentrated to give the crude compound which was purified by Prep-TLC (PE/AE 2:1) to give pure compound I-05a (150 mg, 63.03%) as a pale yellow oil. ESI-MS (M+1): 645 calc. for C$_{33}$H$_{44}$N$_2$O$_9$S.

Preparation of Compound 1-03

N-hydroxy-3-[4-(4-methoxyphenoxyl)Phenylsulfonyl]-8-azaspiro[4.5]decane-3-carboxamide A solution of intermediate I-05a (150 mg, 0.233 mmol) in HCl/dioxane (4 M/L, 5 mL) was stirred at r.t. for 1 h, then concentrated to give the crude product which was purified by prep-HPLC (General procedure, Method 1) to obtain pure compound 1-03 (50 mg, 46.73%) as a red solid. Rt: 2.63, ESI-MS (M+1): 461 calc. for C$_{23}$H$_{28}$N$_2$O$_6$S.

Preparation of compound 1-59

3-(4-fluorophenylsulfonyl)-N-hydroxy-8-azaspiro[4.5]decane-3-carboxamide

Following the same process as described for compound 1-03 but starting from of intermediate I-04a, compound 1-59 was obtained. Rt: 2.11, ESI-MS (M+1): 356 calc. for C$_{16}$H$_{21}$FN$_2$O$_4$S.

Following the same synthetic route 1a, and using the same reagents as for compound 1-03 unless otherwise indicated in the table below, the following compounds were obtained:

| Example | R$_t$ | [M + 1]$^+$ | LC-MS Method | Starting materials |
|---|---|---|---|---|
| 1-01 | 2.51 and 2.71 | 475.2 | 1 | 4-tert-butoxy-carbonyl-4-azaspiro[5.5]-undecane-9-carboxylic acid (1) |
| 1-06 | 2.74 | 489.2 | 1 | 4-(methoxycarbonyl) phenol (R-04) |
| 1-07 | 2.29 | 475.2 | 1 | 4-hydroxybenzoic acid (R-04) |
| 1-08 | 3.04 | 488.2 | 1 | 4-hydroxy-N-methylbenzamide (R-04) |
| 1-09 | 3.30 | 487.3 | 1 | 4-tert-butylphenol (R-04) |
| 1-12 | 3.23 | 462.2 | 1 | 6-methoxypyridin-3-ol (R-04) |
| 1-13 | 3.06 | 488.2 | 1 | N-(4-hydroxyphenyl)acetamide (R-04) |
| 1-15 | 3.77 | 477.2 | 1 | 4-methoxybenzenethiol (R-04) |
| 1-17 | 3.31 | 509.2 | 1 | 4-methoxybenzenethiol (R-04) via I-13 |
| 1-19 | 3.53 | 445.2 | 1 | p-cresol (R-04) |
| 1-22 | 2.58 | 488.3 | 1 | 4-((Dimethylamino)methyl) phenol (R-04) |
| 1-21 | 2.50 | 499.2 | 1 | p-trifluoromethylphenol (R-04) |
| 1-43 | 3.38 | 433.2 | 1 | 6-tert-butoxycarbonyl-6-azaspiro[2.5]octane-2-carboxylic acid (1) and p-methoxyphenol (R-04) |
| 1-54 | 2.31 | 461.2 | 1 | p-methoxyphenol (R-04) |
| 1-55 | 2.18 | 461.2 | 1 | p-methoxyphenol (R-04) |
| 1-62 | 3.28 | 528.2 | 1 | 4-hydroxyphenyl-pyrrolidin-1-yl-methanone (R-04) |
| 1-63 | 3.06 | 502.3 | 1 | 4-hydroxy-N,N-dimethyl-benzamide (R-04) |
| 1-64 | 2.82 | 474.2 | 1 | 4-hydroxybenzamide (R-04) |
| 1-65 | 3.24 | 516.2 | 1 | 4-hydroxy-N-isopropyl-benzamide (R-04) |
| 1-68 | 3.44 | 461.2 | 1 | m-methoxyphenol (R-04) |
| 1-69 | 3.31 | 461.2 | 1 | o-methoxyphenol (R-04) |
| 1-70 | 3.08 | 467.2 | 1 | 4-methoxycyclohexanol (R-04) |
| 1-71 | 3.35 | 432.1 | 1 | Phenol (R-04) |
| 1-72 | 3.81 | 489.2 | 1 | 4-isopropoxyphenol (R-04) |
| 1-73 | 3.90 | 515.2 | 1 | 4-(trifluoromethoxy)phenol (R-04) |
| 1-74 | 3.49 | 489.3 | 1 | Methyl 3-hydroxybenzoate (R-04) |
| 1-75 | 3.13 | 475.2 | 1 | 3-hydroxybenzoic acid (R-04) |
| 1-76 | 3.72 | 466.1 | 1 | 4-chlorophenol (R-04) |
| 1-85 | 2.82 | 488.1 | 1 | 3-hydroxy-N-methylbenzamide (R-04) |
| 1-88 | 1.89 | 493.2 | 1 | 2-fluoro-4-hydroxy benzoic acid (R-04) |
| 1-89 | 1.78 | 506.2 | 1 | 2-fluoro-4-hydroxy-N-methyl benzamide (R-04) |
| 1-91 | 3.41 | 488.1 | 1 | 2-hydroxy-N-methylbenzamide (R-04) |
| 1-93 | 2.10 | 506.2 | 1 | 3-fluoro-4-hydroxy-N-methylbenzamide (R-04) |
| 1-94 | 2.58 | 507.2 | 1 | Methyl 3-fluoro-4-hydroxybenzoate (R-04) |
| 1-95 | 3.48 | 493.2 | 1 | 3-fluoro-4-hydroxy-benzoic acid (R-04) |
| 1-110 | 2.69 | 518.3 | 1 | 4-hydroxy-2-methoxy-N-methyl benzamide (R-04) |
| 1-114 | 2.78 | 549.2 | 1 | 3-chloro-4-(trifluoromethoxy)phenol (R-04) |
| 1-115 | 2.60 | 515.2 | 1 | 3-(trifluoromethoxy)phenol (R-04) |
| 1-117 | 2.37 | 497.1 | 1 | 4-(difluoromethoxy)phenol (R-04) |
| 1-118 | 2.66 | 533.2 | 1 | 3-fluoro-4-(trifluoromethoxy)phenol (R-04) |
| 1-123 | 3.39 | 515.1 | 1 | 4-(trifluoromethoxy)phenol (R-04) |
| 1-126 | 1.71 | 488.1 | 1 | 4-hydroxy-N-methyl benzamide (R-04) |
| 1-127 | 1.85 | 475.2 | 1 | 4-hydroxy benzoic acid (R-04) |

Synthetic Route 2a

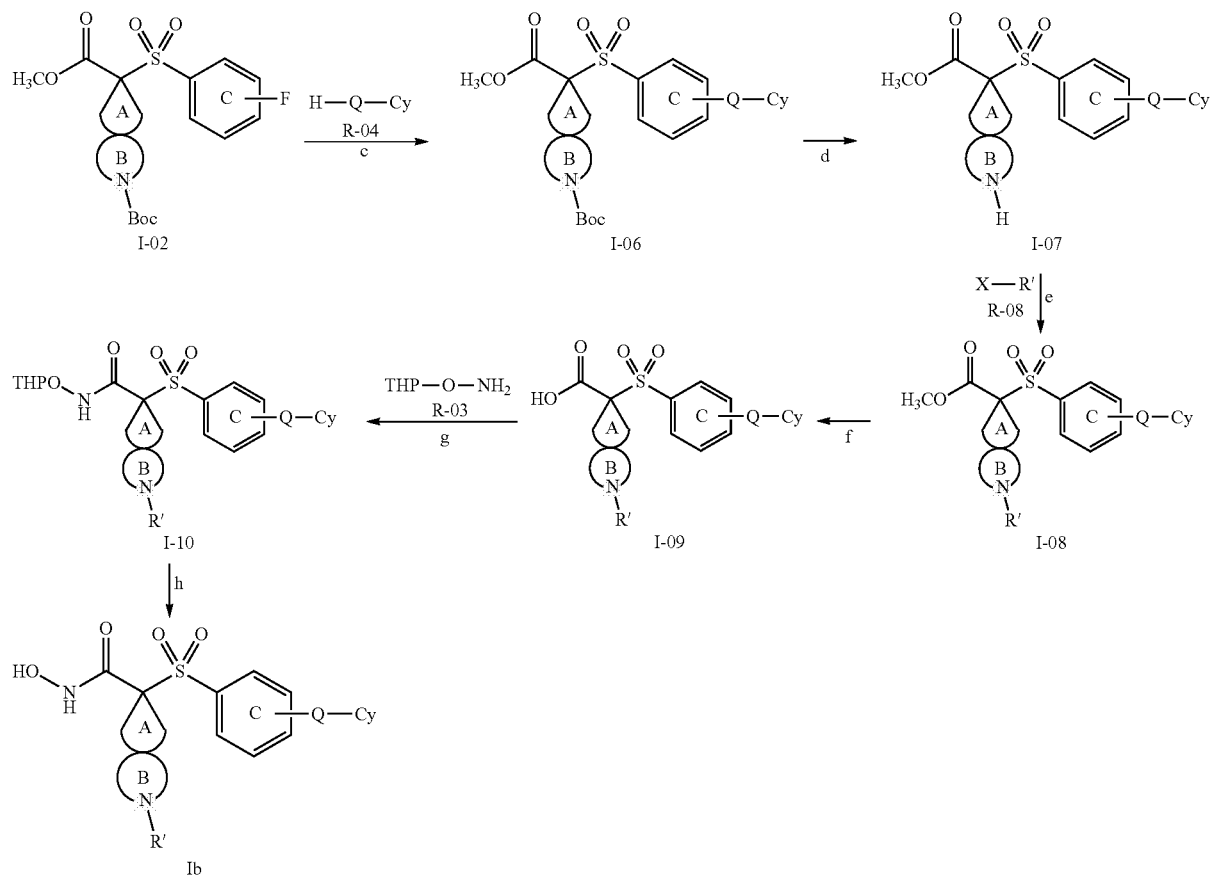

Conditions: c, R-04 (1.5-3 eq), Cs₂CO₃ (2-3 eq), 12 hours at 90° C.; d. HCl in dioxane (4M), r.t.; e. K₂CO₃(2 eq), R-08 (1.5 eq) in ACN, r.t.; f. LiOH•H₂O (10 eq) in THF/MeOH/H2O (3/3/2), r.t.; g. EDC•HCl (2 eq), HOBt (2 eq), THP—O—NH₂ (1.5 eq), NMM (3 eq) in DMF, r.t.; H. -HCl/Dioxane, r.t. for 1 hour.

In the scheme above Q is O or S; X is halogen; R' is a hydrocarbon chain optionally substituted; and Cy is phenyl or a 5- to 6-membered heteroaryl and can be optionally substituted.

Preparation of Intermediate I-06a 8-tert-butoxycarbonyl-3-[4-(4-methoxyphenoxyl) Phenylsulfonyl]-8-azaspiro[4.5]decane-3-carboxylic Acid Methyl Ester To a solution of compound I-02a (900 mg, 1.97 mmol) in DMF (120 mL) was added Cs₂CO₃ (1.92 g, 5.9 mol) and 4-methoxyphenol (490 mg, 3.95 mmol), the reaction mixture was stirred at 60° C. for 2 h. The mixture was diluted with EtOAc and washed with brine, dried over anhydrous Na₂SO₄ and concentrated to give the crude product which was purified by column chromatography (EA:PE=1:30-1:5) to give the compound I-06a (600 mg, 54.0%) as a pale yellow oil. ESI-MS (M+1): 560 calc. for $C_{29}H_{37}NO_8S$.

Preparation of Intermediate I-07a

3-[4-(4-methoxyphenoxyl)Phenylsulfonyl]-8-azaspiro[4.5]decane-3-carboxylic Acid Methyl Ester A solution of compound I-06a (500 mg, 0.89 mmol) in HCl/dioxane (4M, 6 mL) was stirred at r.t. for 3 h. The reaction mixture was concentrated to give the compound I-07a (500 mg, crude). ESI-MS (M+1): 461 calc. for $C_{24}H_{29}NO_6S$.

Preparation of Intermediate I-08a

3-[4-(4-methoxyphenoxyl)Phenylsulfonyl]-8-methyl-8-azaspiro[4.5]decane-3-carboxylic Acid Methyl Ester To a solution of intermediate I-07a (181 mg, 0.39 mmol) in CH₃CN (10 mL) was added K₂CO₃ (107 mg, 0.78 mmol), MeI (28 mg, 0.19 mmol). The reaction mixture was stirred at room temperature for 30 min. After TLC showed that most of starting material was consumed, the mixture was diluted with EtOAc and washed with brine, dried over anhydrous Na₂SO₄ and concentrated to give the crude compound I-08a (110 mg, 59.7%) as a pale yellow oil. ESI-MS (M+1): 588 calc. for $C_{26}H_{33}NO_6S$.

Preparation of Intermediate I-09a

3-[4-(4-methoxyphenoxyl)Phenylsulfonyl]-8-methyl-8-azaspiro[4.5]decane-3-carboxylic Acid To a solution of intermediate I-08 (110 mg, 0.23 mmol) in THF/MeOH/H₂O (3/3/2, 8 mL) was added LiOH H₂O (195 mg, 4.6 mmol). The resulting mixture was refluxed overnight. After TLC showed that most of the staring materials were consumed completely, the mixture was diluted with water and adjusted pH to 2-3. The mixture was extract with EtOAc and washed with brine, dried over anhydrous $Na_2SO_4$ and concentrated to give the crude product I-09a (100 mg, 94.0%) as a pale yellow solid. ESI-MS (M+1): 460 calc. for $C_{24}H_{29}NO_6S$.

Preparation of Intermediate I-10a

3-[4-(4-methoxyphenoxyl)Phenylsulfonyl]-8-methyl-N-(tetrahydro-2H-pyran-2-yloxy)-8-azaspiro[4.5]decane-3-carboxamide To a solution of intermediate I-09a (100 mg, 0.22 mmol) in DMF (10 mL) was added EDCI (84 mg, 0.44 mmol), HOBt (59 mg, 0.44 mmol), THP—O—$NH_2$ (51.5 mg, 0.44 mmol), NMM (66 mg, 0.66 mmol). The mixture was stirred at room temperature overnight. The mixture was diluted with EtOAc and washed with brine, dried over anhydrous $Na_2SO_4$ and concentrated to give the crude product which was purified by column chromatography (EA:PE=1:50-1:4) to give the compound I-10a (78 mg, 64.0%) as a pale yellow solid. ESI-MS (M+1): 559 calc. for $C_{29}H_{38}N_2O_7S$.

Preparation of Compound 1-04

N-hydroxy-3-[4-(4-methoxyphenoxy)-phenylsulfonyl]-8-methyl-8-azaspiro[4.5]decane-3-carboxamide A solution of intermediate I-10a (78 mg, 0.14 mmol) in HCl/dioxane (4 M/L, 10 mL) was stirred at r.t. for 3 h, the reaction mixture was concentrated to give the crude product which was purified by prep-HPLC (General procedure, Method 1) to obtain pure compound 1-04 (14.7 mg, 22.0%) as a pale yellow solid. Rt: 2.66, ESI-MS (M+1): 475 calc. for $C_{24}H_{30}N_2O_6S$.

Following the same synthetic route 2a, and using the same reagents as for compound 1-04 unless otherwise indicated in the table below, the following compounds were obtained:

Synthetic Route 1b

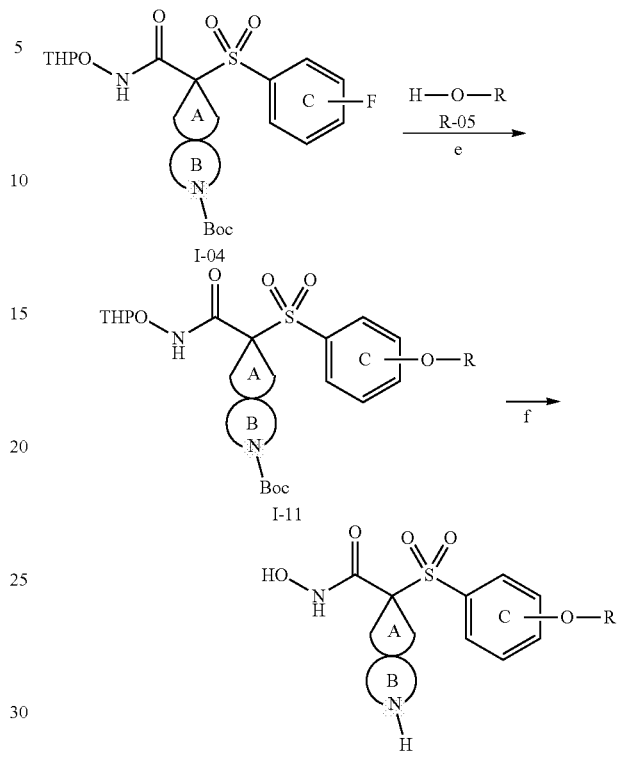

Conditions: e. R-05 (4 eq), NaH (0-4 eq), after 30 min at r.t., 12 h at 90° C.; f. -HCl/Dioxane, r.t. for 1 hour In the scheme above R is a hydrocarbon chain which can be optionally substituted.

Preparation of Intermediate I-11a 8-tert-butoxycarbonyl-3-(4-[2-(piperidin-1-yl)ethoxy]phenylsulfonyl)-N-(tetrahydro-2H-pyran-2-yloxy)-8-azaspiro[4.5]decane-3-carboxamide To a solution of 2-(piperidin-1-yl)ethanol (191 mg, 4 eq) in DMF (5 mL) was added NaH (36 mg, 4 eq), then the

| Example | $R_t$ | $[M + 1]^+$ | LC-MS Method | Starting materials |
|---|---|---|---|---|
| 1-02 | 2.59 and 2.74 | 489.3 | 1 | 4-tert-butoxy-carbonyl-4-azaspiro[5.5]-undecane-9-carboxylic acid (1) |
| 1-28 | 2.56 | 517.2 | 1 | 1-chloropropan-2-one (R-08) |
| 1-29 | 2.52 | 519.2 | 1 | tert-butyl 2-bromoacetate (R-08) |
| 1-30 | 2.96 | 557.2 | 1 | 3,3,3-Trifluoropropyl Bromide (R-08) |
| 1-31 | 2.80 | 503.2 | 1 | 1-Bromopropane (R-08) |
| 1-32 | 2.79 | 501.3 | 1 | Cyclopropyl bromide (R-08) |
| 1-33 | 3.09 | 518.2 | 1 | Methylcarbamic chloride (R-08) |
| 1-34 | 2.39 | 537.3 | 1 | Iodobenzene (R-08) |
| 1-35 | 2.26 | 538.3 | 1 | 2-Bromopyridine (R-08) |
| 1-36 | 3.12 | 551.3 | 1 | Benzyl bromide (R-08) |
| 1-37 | 2.52 | 552.3 | 1 | 4-(Bromomethyl) pyridine (R-08) |
| 1-39 | 2.47 | 541.2 | 1 | 4-(Bromomethyl)-1H-imidazole (R-08) |
| 1-58 | 3.21 | 503.2 | 1 | Acetyl chloride (R-08) |
| 1-124 | 3.53 | 555.2 | 1 | Cyclopropyl bromide (R-08) | mixture was stirred at r.t. for 0.5 h, intermediate I-04a (200 mg, 0.37 mmol) was added, then the reaction mixture was stirred at 90° C. overnight. After TLC (PE/AE 2:1) showed the starting material was consumed, the mixture was quenched with water and extracted with EtOAc, the organic layer was washed with brine, dried over anhydrous $Na_2SO_4$, concentrated to give the crude compound which was purified by Prep-TLC (PE/AE=2:1) to give pure intermediate I-11a (184 mg, 76.67%) as a pale yellow oil. ESI-MS (M+1): 650 calc. for $C_{33}H_{51}N_3O_8S$.

Preparation of Compound 1-11

N-hydroxy-3-(4-[2-(piperidin-1-yl)ethoxy]phenyl-sulfonyl)-8-azaspiro[4.5]decane-3-carboxamide A solution of intermediate I-11a (180 mg, 0.277 mmol) in HCl/dioxane (5 mL) was stirred at r.t. for 1 h, then concentrated to give the crude product by prep-HPLC (General procedure, Method 1) to obtain pure compound 1-11 (58.40 mg, 45.27%) as a pale yellow solid. Rt: 2.14. ESI-MS (M+1): 466 calc. for $C_{23}H_{35}N_3O_5S$.

Following the same synthetic route 1 b, and using the same reagents as for compound 1-11 unless otherwise indicated in the table below, the following compounds were obtained:

| Example | $R_t$ | $[M + 1]^+$ | LC-MS Method | Starting materials |
|---|---|---|---|---|
| 1-05 | 2.80 | 425.2 | 1 | 3-methylbutan-1-ol (R-05) |
| 1-10 | 2.50 | 466.2 | 1 | 1-(2-hydroxyethyl)pyrrolidin-2-one (R-05) |
| 1-18 | 3.67 | 437.2 | 1 | Cyclohexanol (R-05) |
| 1-20 | 3.50 | 445.2 | 1 | Benzyl alcohol (R-05) |
| 1-92 | 2.65 | 451.2 | 1 | Cyclohexylmethanol (R-05) |
| 1-99 | 3.30 | 529.0 | 1 | 4-(trifluoromethoxy)phenyl methanol (R-05) |
| 1-100 | 2.96 | 446.1 | 1 | Pyridin-4-yl methanol (R-05) |
| 1-108 | 1.98 | 502.3 | 1 | 4-(hydroxymethyl)-N-methyl-benzamide (R-05) |
| 1-112 | 2.57 | 435.1 | 1 | 1H-Pyrazol-4-ylmethanol (R-05) |
| 1-113 | 2.56 | 369.1 | 1 | Sodium methoxyde (R-05) |
| 1-130 | 2.97 | 529.2 | 1 | 4-(trifluoromethoxy)phenyl methanol (R-05) |

Synthetic Route 1c

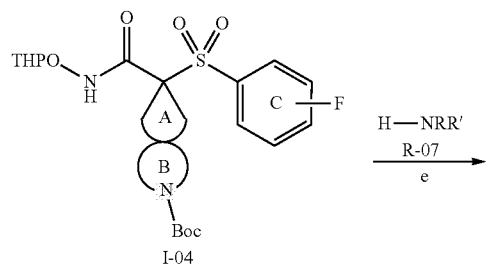

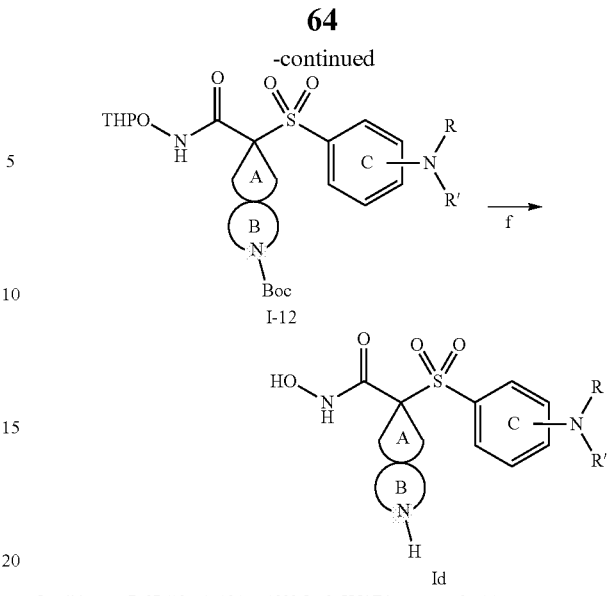

Conditions: e. R-07 (10 eq), 12 h at 100° C.; f. -HCl/Dioxane, r.t. for 1 hour

In the scheme above R' is R or H, and R is a hydrocarbon chain which can be optionally substituted.

Preparation of Intermediate I-12a 8-tert-butoxycarbonyl-3-[4-(4-methoxypiperidin-1-yl)phenylsulfonyl]-Netrahydro-2H-pyran-2-yloxy)-8-azaspiro[4.5]decane-3-carboxamide A solution of intermediate I-04a (100 mg, 0.185 mmol) and 4-methoxypiperidine (213 mg, 10 eq) was stirred at 100° C. overnight. After TLC (PE/AE 2:1) showed the starting material was consumed, the mixture was quenched with water and extracted with EtOAc, the organic layer was washed with brine, dried over anhydrous $Na_2SO_4$, concentrated to give the crude compound which was purified by prep-TLC (PE/AE 1:1) to give pure intermediate I-12a (50 mg, 42.74%) as a pale yellow oil. ESI-MS (M+1): 636 calc. for $C_{32}H_{49}N_3O_8S$.

Preparation of Compound 1-16

N-hydroxy-3-[4-(4-methoxypiperidin-1-yl)phenyl-sulfonyl]-8-azaspiro[4.5]decane-3-carboxamide A solution of intermediate I-12a (50 mg, 0.079 mmol) in HCl/dioxane (3 mL) was stirred at r.t. for 1 h, then concentrated to give the crude product which was purified by prep-HPLC (General procedure, Method 1) to obtain pure compound 1-16 (25.0 mg, 69.44%) as a pale yellow solid. ESI-MS (M+1): 452 calc. for $C_{22}H_{33}N_3O_5S$.

Following the same synthetic route 1c, and using the same reagents as for compound 1-16 unless otherwise indicated in the table below, the following compounds were obtained:

| Example | $R_t$ | $[M + 1]^+$ | LC-MS Method | Starting materials |
|---|---|---|---|---|
| 1-14 | 3.57 | 436.3 | 1 | Cyclohexylamine (R-07) |
| 1-61 | 1.99 | 354.2 | 1 | Benzylamine (R-07) |
| 1-67 | 2.51 | 444.3 | 1 | Benzylamine (R-07) |
| 1-77 | 3.00 | 466.3 | 1 | 4-methoxycyclohexanamine (R-07) |
| 1-78 | 1.83 | 436.3 | 1 | Cyclohexylnamine (R-07) |
| 1-79 | 2.15 | 436.3 | 1 | Cyclohexylnamine (R-07) |

-continued

| Example | $R_t$ | $[M + 1]^+$ | LC-MS Method | Starting materials |
|---|---|---|---|---|
| 1-82 | 2.02 | 450.1 | 1 | Cyclohexylmethanamine (R-07) |
| 1-83 | 2.94 | 493.2 | 1 | 4-amino-N-methyl-cyclohexanecarboxamide (R-07) |
| 1-84 | 2.40 | 480.2 | 1 | 4-aminocyclohexanecarboxylic acid (R-07) |
| 1-96 | 1.47 | 438.1 | 1 | Tetrahydropyran-4-amine (R-07) |
| 1-97 | 2.08 | 422.1 | 1 | Cyclopentanamine (R-07) |
| 1-103 | 2.58 | 528.2 | 1 | 4-(trifluoromethoxy)phenyl-methanamine (R-07) |
| 1-104 | 1.56 | 501.2 | 1 | 4-(aminomethyl)-N-methyl benzamide (R-07) |
| 1-105 | 3.30 | 502.2 | 1 | Methyl 4-(aminomethyl) benzoate (R-07) |
| 1-106 | 1.75 | 488.2 | 1 | 4-(aminomethyl) benzoic acid (R-07) |
| 1-109 | 3.65 | 472.2 | 1 | 4-4-difluorocyclohexylamine (R-07) |
| 1-125 | 2.20 | 486.2 | 1 | (4-4-difluorocyclohexyl)methanamine (R-07) |

Synthetic Route 1d

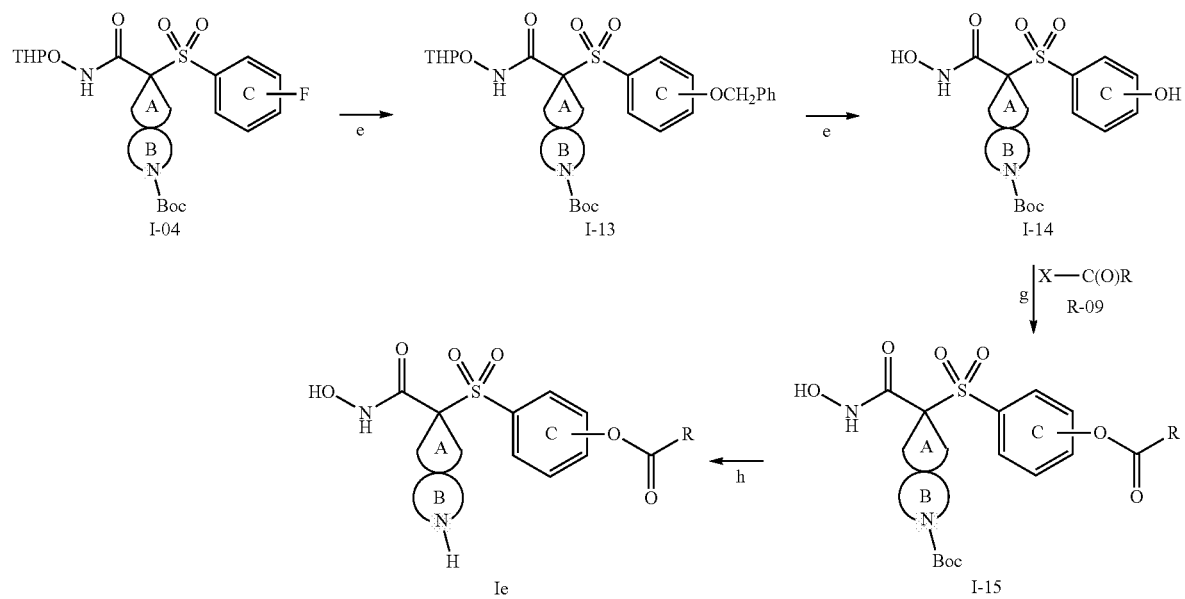

Conditions: e. Benzyl alcohol (4 eq), NaH (4 eq), after 30 min at r.t., 12 h at 90° C.; f. -Pd/C (0.5 g) at $H_2$ atmosphere, r.t. for 1 hour; g.-R-09 (1.2 eq), $Et_3N$ (3 eq) in DCM, r.t. overnight; h. -HCl/Dioxane, r.t. for 1 hour In the scheme above R is a hydrocarbon chain optionally substituted, a carbocyclic or heteroaliphatic ring optionally substituted, a phenyl or 5- to 6-membered heteroaryl optionally substituted.

Preparation of Intermediate I-13a

3-[4-(benzyloxy)phenylsulfonyl]-8-tert-butoxycarbonyl-N-(tetrahydro-2H-pyran-2-yloxy)-8-azaspiro[4.5]decane-3-carboxamide To a solution of phenylmethanol (500 mg, 5 eq) in THF (5 mL) was added NaH (110 mg, 5 eq), then the mixture was stirred at r.t for 0.5 h, intermediate I-04a (500 mg, 0.926 mmol) was added, then the reaction mixture was stirred at 80° C. overnight. After TLC (PE/AE 2:1) showed the starting material was consumed, the mixture was quenched with water and extracted with EtOAc, the organic layer was washed with brine, dried over anhydrous $Na_2SO_4$, concentrated to give the crude compound which was purified by prep-TLC (PE/AE 2:1) to give pure intermediate I-13a (380 mg, 65.29%) as a pale yellow oil. ESI-MS (M+1): 629 calc. for $C_{33}H_{44}N_2O_8S$.

Preparation of Intermediate I-14a 8-tert-butoxycarbonyl-3-[4-hydroxyphenylsulfonyl]-Netrahydro-2H-pyran-2-yloxy)-8-azaspiro[4.5]decane-3-carboxamide To a solution of intermediate I-13a (380 mg, 0.605 mmol) in MeOH (20 mL) was added Pd/C (0.5 g) at room temperature at $H_2$ atmosphere, then the mixture was stirred at room temperature for 1 h until TLC (PE/AE 2:1) showed the starting material was consumed, then filtered and the filtrate was concentrated to give the crude product I-14a (180 mg, 55.38%) which was used for the next step without further purification. ESI-MS (M+1): 539 calc. for $C_{26}H_{38}N_2O_8S$.

Preparation of Intermediate I-15a 8-tert-butoxycarbonyl-3-[4-(4-10 methoxybenzoyloxy)Phenylsulfonyl]-Netrahydro-2H-pyran-2-yloxy)-8-azaspiro[4.5]decane-3-carboxamide To a solution of intermediate I-14a (60 mg, 0.151 mmol) and Et$_3$N (46 mg, 3 eq) in DCM (5 mL) was added 4-methoxybenzoyl chloride (31 mg, 1.2 eq) at room temperature, then the mixture was stirred at r.t overnight. After TLC (PE/AE 2:1) showed the starting material was consumed, the mixture was extracted with DCM, the organic layer was washed with brine, dried over anhydrous Na$_2$SO$_4$, concentrated to give the crude compound which was purified by prep-TLC (PE/AE 2:1) to give pure compound I-15a (38 mg, 37.62%) as a pale yellow oil. ESI-MS (M+1): 673 calc. for $C_{34}H_{44}N_2O_{10}S$.

Preparation of Compound 1-26

N-hydroxy-3-[4-(4-methoxybenzoyloxyl)phenylsulfonyl]-8-azaspiro[4.5]decane-3-carboxamide A solution of intermediate I-15a (38 mg, 0.057 mmol) in HCl/dioxane (5 mL) was stirred at r.t for 1 h, then concentrated to give the crude product by prep-HPLC (General procedure, Method 1) to obtained pure compound 1-26 (22 mg, 78.57%) as a pale yellow solid. Rt: 2.71, ESI-MS (M+1): 489 calc. for $C_{24}H_{28}N_2O_7S$.

Preparation of Compound 1-60

N-hydroxy-3-(4-hydroxyphenylsulfonyl)-8-azaspiro[4.5]decane-3-carboxamide

Following the same process as described for compound 1-26 but starting from of intermediate I-14a, compound 1-60 was obtained. Rt: 2.11, ESI-MS (M+1): 354 calc. for $C_{16}H_{22}N_2O_5S$.

Following the same synthetic route Id, and using the same reagents as for compound 1-26 unless otherwise indicated in the table below, the following compounds were obtained:

| Example | R$_t$ | [M + 1]$^+$ | LC-MS Method | Starting materials |
|---|---|---|---|---|
| 1-86 | 3.12 | 503.1 | 1 | 4-chlorocarbonyl benzoic acid (R-09) |
| 1-87 | 2.79 | 516.2 | 1 | 4-(methylcarbamoyl)benzoyl chloride (R-09) |
| 1-98 | 2.47 | 465.3 | 1 | Cyclohexanecarbonyl chloride (R-09) |
| 1-101 | 1.84 | 534.2 | 1 | 3-fluoro-4-(methylcarbamoyl)benzoyl chloride (R-09) |
| 1-102 | 2.75 | 543.1 | 1 | 4-(trifluoromethoxy)benzoyl chloride (R-09) |
| 1-119 | 2.20 | 489.0 | 1 | 4-methoxybenzoyl chloride (R-09) |
| 1-120 | 2.61 | 543.1 | 1 | 4-(trifluoromethoxy)benzoyl chloride (R-09) |

Synthetic Route 1e

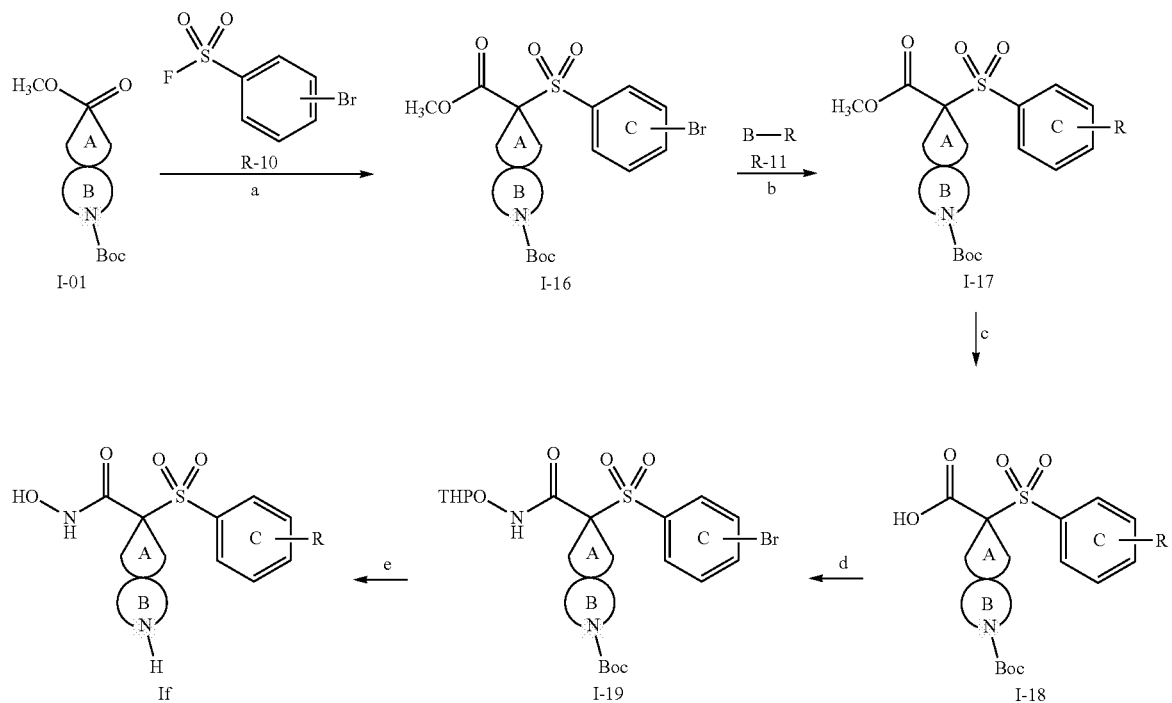

Conditions: a. LDA (2.0M) in THF, 1 hour at -78° C.; then, R-10 (1.2 eq), 1 hour at -78° C.; b. Pd(dppf)Cl$_2$ (0.1 eq) and Na$_2$CO$_3$ (2 eq) indioxane/H$_2$O, r.t. overnight; c. LiOH•H$_2$O (10 eq) in THF/MeOH/H$_2$O (3/3/2), r.t.; d. EDC•HCl (2 eq), HOBt (2 eq), THP—O—NH$_2$ (1.5 eq), NMM (3 eq) in DMF, r.t.; e. -HCl/Dioxane, r.t. for 1 hour.

In the scheme above B is boronic acids, boronate esters or trifluoroborate salts and R is phenyl or a 5- to 6-membered heteroaryl or a 3- to 7-heterocyclic or carbocyclic aliphatic ring or a hydrocarbon chain which can be optionally substituted.

Preparation of Reagent R-10a 4-bromobenzenesulfonyl Fluoride

To a solution of 4-bromobenzenesulfonyl chloride (2.29 g, 9 mmol) in $CH_3CN$ (45 mL) was added KF (2.1 g, 36 mmol) and 18-crown-6 (0.5 g), then the mixture was stirred at room temperature overnight. The mixture was quenched with aqueous water and extracted with EtOAc, the organic layer was washed with brine, dried over anhydrous $Na_2SO_4$, concentrated to give the crude product which was purified by column to give the reagent R-10a (1.6 g, 74.4%) as a pale yellow solid. ESI-MS (M+1): 239.2 calc. for $C_6H_4BrFO_2S$.

Preparation of Intermediate I-16a 8-tert-butoxycarbonyl-3-(4-bromophenylsulfonyl)-8-azaspiro[4.5]decane-3-carboxylic Acid Methyl Ester To a solution of compound I-01a (230 mg, 0.77 mmol) in THF (20 mL) was added LDA (0.6 mL, 2.0 M, 1.2 mmol) at −78° C. After stirring at −78° C. for 1 hour, the reagent R-10a (214 mg, 0.9 mmol) was added to the solution, the reaction was stirred at −78° C. for 1 hour, and then the mixture was stirred at r.t overnight. After TLC (PE/AE 5:1) showed the starting material was consumed, the mixture was quenched with aqueous $NH_4Cl$ and extracted with EtOAc, the organic layer was washed with brine, dried over anhydrous $Na_2SO_4$, concentrated to give the crude product which was purified by column chromatography (eluting with EA/PE=100:1 to 10:1) to give pure compound I-16a (150 mg, 38%) as a pale yellow oil. ESI-MS (M-55): 459.9 calc. for $C_{22}H_{30}BrNO_6S$.

Preparation of Intermediate I-17a 8-tert-butoxycarbonyl-3-(4-(4-methoxyphenyl)Phenylsulfonyl)-8-azaspiro[4.5]decane-3-carboxylic Acid Methyl Ester To a suspension of compound I-16a (50 mg, 0.1 mmol) and the commercially available 4-methoxyphenyl boronic acid (20 mg, 0.13 mmol, R-11 ), in dioxane (10 mL)/$H_2O$ (2 mL) was added $Pd(dppf)Cl_2$ (10 mg) and $Na_2CO_3$ (22 mg, 0.2 mmol). The mixture was stirred at reflux under $N_2$ overnight. The resulting mixture was cooled to room temperature and water was added. The organic layer was separated and the aqueous layer was extracted 3 times with EtOAc. The combined organic layer was washed with brine, dried over sodium sulfate and concentrated under reduced pressure and purified by prep-TLC to afford the desired product I-17a (52 mg, 95%). ESI-MS (M-55): 488.0 calc. for $C_{29}H_{37}NO_7S$.

Preparation of Intermediate I-18a 8-tert-butoxycarbonyl-3-(4-(4-methoxyphenyl)Phenylsulfonyl)-8-azaspiro[4.5]decane-3-carboxylic Acid To a solution of compound I-17a (52 mg, 0.096 mmol) in THF/MeOH/$H_2O$ (3/3/2, 8 mL) was added $LiOH.H_2O$ (42 mg, 10 eq). The resulting mixture was stirred at r.t. for 4 h, after TLC (PE/AE 5:1) showed the staring materials were consumed completely, then the mixture was diluted with water and adjusted pH to 3-4 with 1N HCl and the mixture was extracted with EtOAc, washed with brine, dried over anhydrous $Na_2SO_4$, concentrated to give the crude product 1-18a (50 mg, ~100%) as a pale yellow oil which was used directly in the next step. ESI-MS (M-55): 473.9; calc. for $C_{28}H_{35}NO_7S$ Preparation of Intermediate I-19a 8-tert-butoxycarbonyl-3-(4-(4-methoxyphenyl)Phenylsulfonyl)-N-(tetrahydro-2H-pyran-2-yloxy)-8-azaspiro[4.5]decane-3-carboxamide To a solution of compound I-18a (50 mg, 0.095 mmol) in DMF (15 mL) was added EDC.HCl (40 mg, 0.2 mmol), HOBt (27 mg, 0.2 mmol), $THPONH_2$ (24 mg, 0.2 mmol), NMM (40 mg, 0.4 mmol), then the mixture was stirred at room temperature overnight. The mixture was quenched with aqueous water and extracted with EtOAc, the organic layer was washed with brine, dried over anhydrous $Na_2SO_4$, concentrated to give the crude product which was purified by prep-TLC to give the compound I-19a (45 mg, 72%) as a pale yellow solid. ESI MS (M-139): 488.9; calc. for $C_{33}H_{44}N_2O_8S$.

Preparation of Compound 1-41

N-hydroxy-3-(4-(4-methoxyphenyl)Phenylsulfonyl)-8-azaspiro[4.5]decane-3-carboxamide A solution of intermediate I-19a (45 mg, 0.072 mmol) in HCl/dioxane (10 mL, 2 N) was stirred at r.t for 2 h, then concentrated to give the crude product which was purified by prep HPLC twice (General procedure, Method 1) to obtained pure compound 1-41 (6.6 mg, 16.8%) as a yellow solid. ESI-MS (M+1): 445.2 calc. for $C_{23}H_{28}N_2O_5S$. Rt is 2.01.

Following the same synthetic route 1e, and using the same reagents as for compound 1-41 unless otherwise indicated in the table below, the following compounds were obtained:

| Example | $R_t$ | $[M + 1]^+$ | LC-MS Method | Starting materials |
|---------|-------|-------------|--------------|---------------------|
| 1-66 | 2.26 | 429.2 | 1 | 1,3,2-Dioxaborolane, 4,4,5,5-tetramethyl-2-(phenylmethyl)-(R-11) |

Synthetic Route 1f

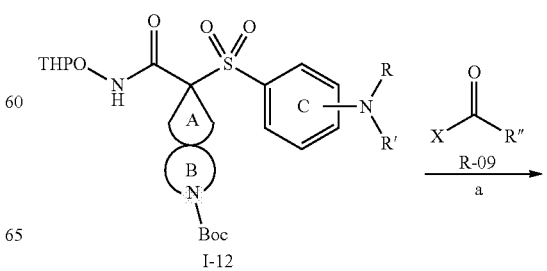

I-12

71

-continued

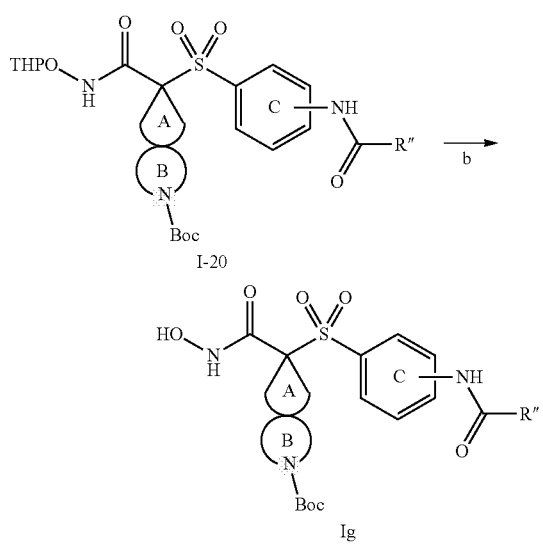

Conditions: a. R-09 (1.2 eq), Et₃N (2 eq) in DCM, r.t. overnight;
b. HCl/Dioxane, r.t. for 1 hour.

In the scheme above R and R' are hydrogen, X is a halogen and R" is phenyl or a 5- to 6-membered heteroaryl or a 3- to 7-heterocyclic or carbocyclic aliphatic ring or a hydrocarbon chain which can be optionally substituted.

72

Preparation of Intermediate I-20a 8-tert-butoxycarbonyl-3-(4-(cyclohexanecarbo-nylamino)Phenylsulfonyl)-N-(tetrahydro-2H-pyran-2-yloxy)-8-azaspiro[4.5]decane-3-carboxamide To a solution of compound I-12c (80 mg, 0.149 mmol), intermediate obtained to synthesize 1-61 (following synthetic route 1c), in DCM (3 mL) was added cyclohexanecarbonyl chloride (26.2 mg, 1.2 eq) and Et₃N (30.1 mg, 0.298 mmol), then the reaction mixture was stirred at r.t overnight. After TLC (PE/AE 5:1) showed the starting material was consumed, the mixture was quenched with water and extracted with EtOAc, the organic layer was washed with brine, dried over anhydrous Na₂SO₄, concentrated to give the crude compound which was purified by Prep-TLC (PE/AE 5:1) to give pure intermediate I-20a (65 mg, 67.50%) as a white solid. ESI-MS (M+1): 648.3 calc. for $C_{33}H_{49}N_3O_8S$.

Preparation of Compound 1-81

N-hydroxy-3-(4-(cyclohexanecarbonylamino)Phe-nylsulfonyl)-8-azaspiro[4.5]decane-3-carboxamide A solution of compound I-20a (65 mg, 0.1 mmol) in HCl/dioxane (3 mL) was stirred at r.t for 1 h, then concentrated to give the crude product which was purified by prep-HPLC (General procedure, Method 1) to obtained pure compound 1-81 (22.0 mg, 45.74%) as a yellow solid. ESI-MS (M+1): 464.2 calc. for $C_{23}H_{33}N_3O_5S$. Rt is 1.89.

Synthetic Route 3a

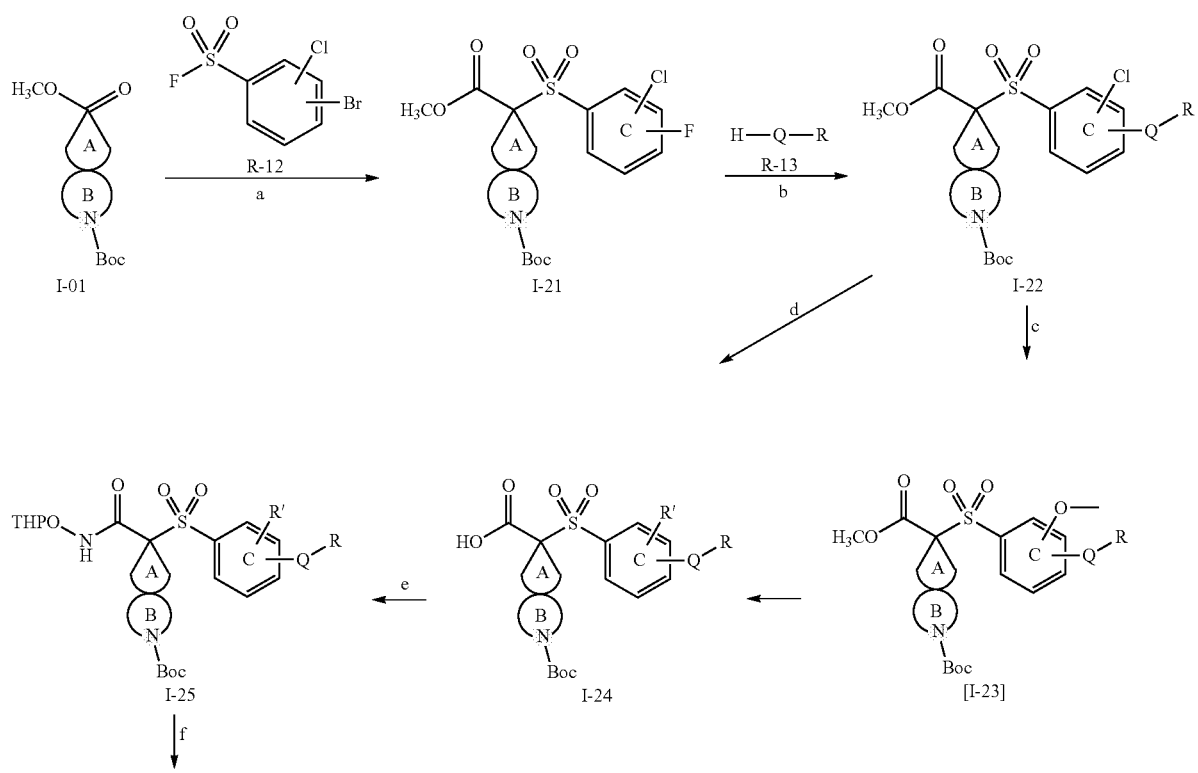

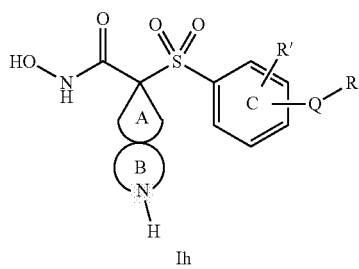

Ih

Conditions: a. LDA (1.20M) in THF, 1 hour at -78° C.; then, R-12 (1.2 eq), 1 hour at -78° C.; b. R-13 (3-10 eq), NaH (0-3 eq) in THF, r.t. - reflux overnight; c. CuI (2 eq), MeOH/MeONa (25%, 20 eq) in DMF, 20 minutes at 110° C.; d. LiOH·H$_2$O (10 eq) in THF/MeOH/H$_2$O (3/3/2), r.t.; e. EDC·HCl (2 eq), HOBt (2 eq), THP—O—NH$_2$ (1.5 eq), NMM (3 eq) in DMF, r.t.; f. HCl/Dioxane, r.t. for 1 hour.

In the scheme above Q is O or NH, R is a 3- to 7-heterocyclic or carbocyclic aliphatic ring or a hydrocarbon chain which can be optionally substituted and R' is halogen or alkoxy.

Preparation of Reagent R-12a 3-chloro-4-fluorobenzenesulfonyl Fluoride

To a solution of the commercially available 3-chloro-4-fluorobenzenesulfonyl chloride (7 g, 30 mmol) in CH$_3$CN (40 mL) was added KF (7 g, 120 mmol) and 18-crown-6 (0.5 g), then the mixture was stirred at room temperature overnight. The mixture was quenched with aqueous water and extracted with EtOAc, the organic layer was washed with brine, dried over anhydrous Na$_2$SO$_4$, concentrated to give the crude product which was purified by column to give the reagent R-12a (4.2 g, 95.5%) as a pale yellow solid. ESI-MS (M+1): 213.2 calc. for C$_6$H$_3$ClF$_2$O$_2$S.

Preparation of Intermediate I-21a 8-tert-butoxycarbonyl-3-(3-chloro-4-fluorophenyl-sulfonyl)-8-azaspiro[4.5]decane-3-carboxylic Acid Methyl Ester To a solution of compound I-01a (743 mg, 2.5 mmol) in THF (20 mL) was added LDA (4.2 mL, 1.2 M, 5 mmol) at -78° C. After stirring at -78° C. for 1 hour, the reagent R-12a (640 g, 3.0 mmol) was added to the solution, the reaction was stirred at -78° C. for 1 hour, and then the mixture was stirred at r.t overnight. After TLC (PE/AE 5:1) showed the starting material was consumed, the mixture was quenched with aqueous NH$_4$Cl and extracted with EtOAc, the organic layer was washed with brine, dried over anhydrous Na$_2$SO$_4$, concentrated to give the crude product which was purified by column chromatography (eluting with EA/PE=100:1 to 10:1) to give pure intermediate I-21a (349 mg, 29%) as a pale yellow oil. ESI-MS (M-55): 434.1 calc. for C$_{22}$H$_{29}$ClFNO$_6$S.

Preparation of Intermediate I-22a 8-tert-butoxycarbonyl-3-(3-chloro-4-(cyclohexy-lamino)Phenylsulfonyl)-8-azaspiro[4.5]decane-3-carboxylic Acid Methyl Ester The intermediate I-21a (240 mg, 0.51 mmol) was dissolved in cyclohexylamine (505 mg, 5.1 mmol), R13a. The solution was stirred at 85° C. overnight. The mixture was quenched with aqueous water and extracted with EtOAc, the organic layer was washed with brine, dried over anhydrous Na$_2$SO$_4$, concentrated to give the crude product which was purified by prep-TLC to give the compound I-22a (110 mg, 38%) as a pale yellow solid. ESI-MS (M-55): 513; calc. for C$_{28}$H$_{41}$ClN$_2$O$_6$S.

Preparation of Intermediate I-24a 8-tert-butoxycarbonyl-3-(3-methoxy-4-(cyclohexy-lamino)Phenylsulfonyl)-8-azaspiro[4.5]decane-3-carboxylic Acid The compound I-22a (179 mg, 0.326 mmol), CuI (124.5 mg, 0.652 mmol) and MeOH/MeONa (25%, 1.41 g, 6.52 mmol) was dissolved in DMF (10 mL). The solution was stirred at 110° C. for 20 min. The mixture was quenched with aqueous water and extracted with EtOAc, the organic layer was washed with brine, dried over anhydrous Na$_2$SO$_4$, concentrated to give the crude product which was purified by prep-TLC to give the compound I-24a (160 mg, 88%) as a pale yellow solid. The hydrolysis of the methyl ester to the corresponding carboxylic acid occurred simultaneously together with the methoxylation; thus, compound I-23a was not isolated and the intermediate I-24a was directly obtained from I-22a. ESI-MS (M-55): 495.2; calc. for C$_{28}$H$_{42}$N$_2$O$_7$S.

Preparation of Intermediate I-25a 8-tert-butoxycarbonyl-3-(3-methoxy-4-(cyclohexy-lamino)Phenylsulfonyl)-N-(tetrahydro-2H-pyran-2-yloxy)-8-azaspiro[4.5]decane-3-carboxamide To a solution of compound I-24a (160 mg, 0.29 mmol) in DMF (15 mL) was added EDC.HCl (112 mg, 0.58 mmol), HOBt (79 mg, 0.58 mmol), THPONH$_2$ (68 mg, 0.58 mmol) and NMM (88 mg, 0.87 mmol) at r.t, then the mixture was stirred at room temperature overnight. The mixture was quenched with aqueous water and extracted with EtOAc, the organic layer was washed with brine, dried over anhydrous Na$_2$SO$_4$, concentrated to give the crude product which was purified by prep-TLC to give the intermediate I-25a (100 mg, 53%) as a pale yellow solid. ESI-MS (M-139): 510.1; calc. for C$_{33}$H$_{51}$N$_3$O$_8$S.

Preparation of Compound 1-90

N-hydroxy-3-(3-methoxy-4-(cyclohexylamino)Phe-nylsulfonyl)-8-azaspiro[4.5]decane-3-carboxamide A solution of compound I-25a (100 mg, 0.15 mmol) in HCl/dioxane (10 mL) was stirred at r.t for 2 h, then concentrated to give the crude product which was purified by prep HPLC (General procedure, Method 1) to obtained pure compound 1-90 (39.7 mg, 58%) as a white solid. ESI-MS (M+1): 466.1 calc. for $C_{23}H_{35}N_3O_5S$. Rt is 2.48.

Preparation of Compound 1-116

N-hydroxy-3-(3-chloro-4-fluorophenylsulfonyl)-8-azaspiro[4.5]decane-3-carboxamide Following the same process as described for compound 1-90 but skipping the second and third step (b and c) from synthetic route described above (3a), compound 1-116 was obtained. Rt is 2.96, ESI-MS (M+1): 391.2 calc. for $C_{16}H_{20}ClFN_2O_4S$.

Following the same synthetic route 3a, and using the same reagents as for compound 1-90 unless otherwise indicated in the table below, the following compounds were obtained:

| Example | $R_t$ | $[M + 1]^+$ | LC-MS Method | Starting materials |
|---------|-------|-------------|--------------|--------------------|
| 1-80 | 2.26 | 470.1 | 1 | Cyclohexylamine (R-13) |
| 1-107 | 2.42 | 403.1 | 1 | Sodium trimethylsilanoate (R-13) |
| 1-121 | 2.64 | 389.1 | 1 | Sodium trimethylsilanoate (R-13) |
| 1-122 | 2.49 | 479.2 | 1 | Benzyl alcohol (R-13) |

Synthetic Route 3b was added $Cs_2CO_3$ (700 mg, 2.2 mmol). The mixture was stirred at reflux under $N_2$ overnight. The resulting mixture was cooled to room temperature and water was added. The organic layer was separated and the aqueous layer was extracted 3 times with EtOAc. The combined organic layers were washed with brine, dried over sodium sulfate and concentrated under reduced pressure and purified by prep TLC to afford the desired product I-26a (380 mg, 75%). ESI-MS (M-55): 538.2 calc. for $C_{29}H_{36}ClNO_8S$.

Preparation of Intermediate I-27a 8-tert-butoxycarbonyl-3-(3-chloro-4-(4-methoxyphenoxy)phenylsulfonyl)-8-azaspiro[4.5]decane-3-carboxylic acid To a solution of compound I-26a (310 mg, 0.52 mmol) in $THF/MeOH/H_2O$ (3/3/2, 16 mL) was added $LiOH·H_2O$ (225 mg, 10 eq). The resulting mixture was stirred at r.t. for 4 h, after TLC (PE/AE 5:1) showed the staring materials were consumed completely, then the mixture was diluted with water and adjusted pH to 3~4 with 1N HCl and the mixture was extracted with EtOAc, washed with brine, dried over anhydrous $Na_2SO_4$, concentrated and purified by prep-TLC to afford the desired product I-27a (120 mg, 40%). ESI-MS (M-55): 524.2; calc. for $C_{28}H_{34}ClNO_8S$.

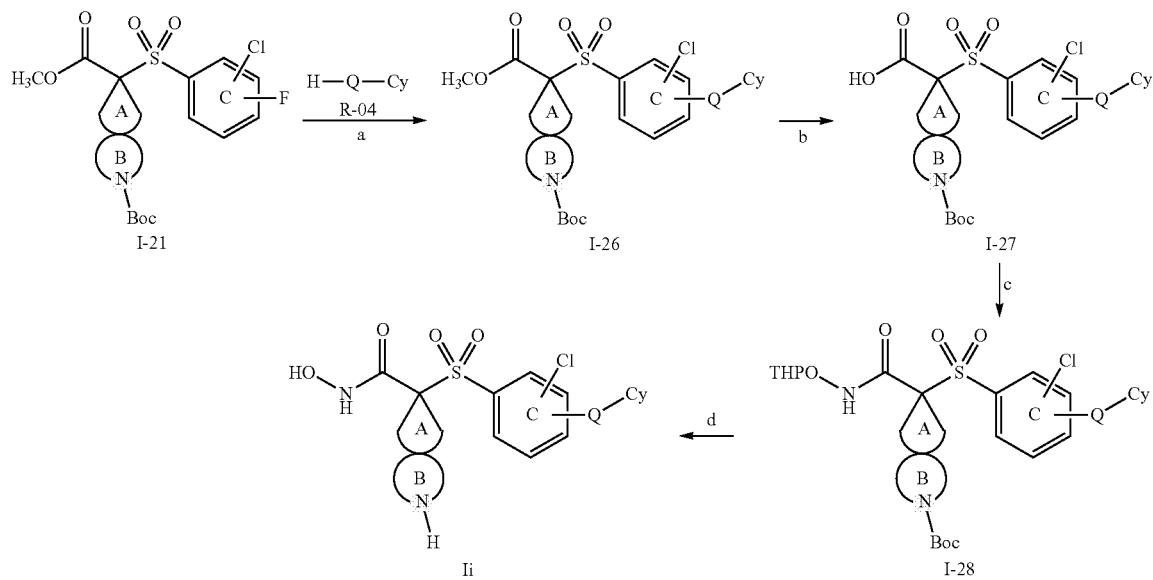

Conditions: a. R-04 (1.5-3 eq), $Cs_2CO_3$ (2-3 eq), 12 hours at 90° C.; b. LiOH•$H_2O$ (10 eq) in THF/MeOH/$H_2O$ (3/3/2), r.t.; c. EDC•HCl (2 eq), THP—O—$NH_2$ (1.5 eq), NMM (3 eq) in DMF, r.t.; d. HCl/Dioxane, r.t. for 1 hour.

In the scheme above Q is O or S and Cy is phenyl or a 5- to 6-membered heteroaryl and can be optionally substituted.

Preparation of Intermediate I-26a 8-tert-butoxycarbonyl-3-(3-chloro-4-(4-methoxyphenoxyl)Phenylsulfonyl)-8-azaspiro[4.5]decane-3-carboxylic Acid Methyl Ester To a suspension of compound 1-21a (420 mg, 0.86 mmol) and p-methoxyphenol (214 mg, 1.72 mmol), in DMF (5 mL)

Preparation of Intermediate I-28a 8-tert-butoxycarbonyl-3-(3-chloro-4-(4-methoxyphenoxyl)Phenylsulfonyl)-N-(tetrahydro-2H-pyran-2-yloxy)-8-azaspiro[4.5]decane-3-carboxamide To a solution of intermediate I-27a (120 mg, 0.21 mmol) in DMF (10 mL) was added EDC.HCl (81 mg, 0.42 mmol), HOBt (57 mg, 0.42 mmol), $THPONH_2$ (50 mg, 0.42 mmol), NMM (64 mg, 0.63 mmol), then the mixture was stirred at room temperature overnight. The mixture was quenched with aqueous water and extracted with EtOAc, the organic layer was washed with brine, dried over anhydrous $Na_2SO_4$, concentrated to give the crude product I-28a (160 mg, ~100%) as a pale yellow oil which was used directly in the next step. ESI-MS (M-139): 539.2; calc. for $C_{33}H_{43}ClN_2O_9S$.

Preparation of Compound 1-56

N-hydroxy-3-(3-chloro-4-(4-methoxyphenoxyl)Phenylsulfonyl)-8-azaspiro[4.5]decane-3-carboxamide A solution of intermediate I-28a (160 mg, ~0.21 mmol) in HCl/dioxane (10 mL, 1 N) was stirred at r.t for 2 h, then concentrated to give the crude product which was purified by prep-HPLC (General procedure, Method 1) to obtained pure compound 1-56 (30.8 mg, 29.7%) as a yellow solid. ESI-MS (M+1): 495.2 calc. for $C_{23}H_{27}ClN_2 6S$. Rt is 2.66.

Following the same synthetic route 3b, and using the same reagents as for compound 1-56 unless otherwise indicated in the table below, the following compounds were obtained:

| Example | $R_t$ | $[M + 1]^+$ | LC-MS Method | Starting materials |
|---|---|---|---|---|
| 1-111 | 3.51 | 549.2 | 1 | 4-(trifluoromethoxy)phenol (R-04) |

Synthetic Route 3c

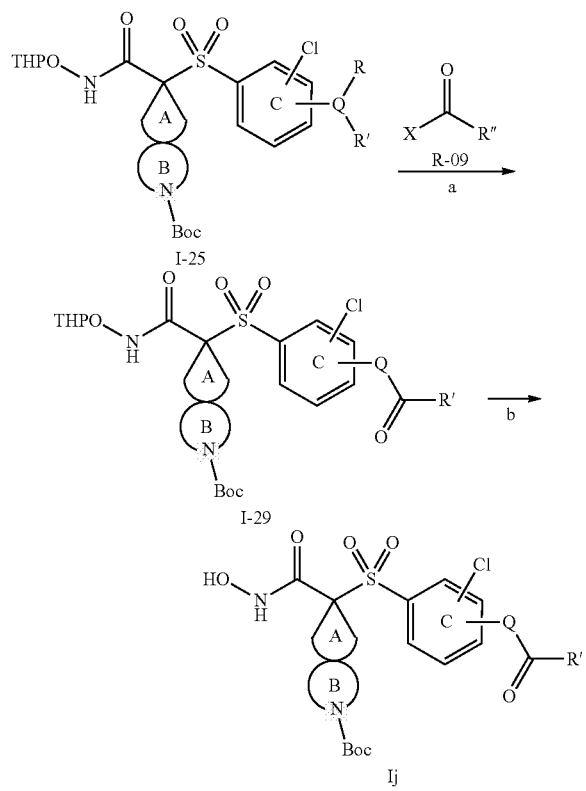

Conditions: a. R-09 (1.2 eq), Et3N (4 eq) in DCM, r.t. overnight;
b. HCl/Dioxane, r.t. for 1 hour.

In the scheme above Q is O or NH, R is hydrogen, X is a halogen and R' is phenyl or a 5- to 6-membered heteroaryl or a 3- to 7-heterocyclic or carbocyclic aliphatic ring or a hydrocarbon chain which can be optionally substituted.

Preparation of Intermediate I-29a 8-tert-butoxycarbonyl-3-(3-chloro-4-(4-(trifluoromethoxy)Benzoyloxy)Phenylsulfonyl)-N-(tetrahydro-2H-pyran-2-yloxy)-8-azaspiro[4.5]decane-3-carboxamide To a solution of compound I-25e (115 mg, 0.2 mmol), intermediate obtained to synthesize 1-121 (following synthetic route 3a), and $Et_3N$ (61 mg, 0.6 mmol) in DCM (10 mL) was added dropwise the commercially available 4-(Trifluoromethoxy)benzoyl chloride, R-09, (0.3 mmol) in DCM (5 mL) with stirring at 0° C. under $N_2$. The mixture solution was stirred at r.t overnight. The mixture solution was added water and extracted with EtOAc, the organic layer was washed with brine, dried over anhydrous $Na_2SO_4$, concentrated to give the crude product which was purified by prep-TLC to give the intermediate I-29a (40 mg, 26%) as a yellow solid. ESI-MS (M-139): 621.1; calc. for $C_{34}H_4O ClF_3N_2O_{10}S$.

Preparation of Compound 1-128

N-hydroxy-3-(3-chloro-4-(4-(trifluoromethoxy)Benzoyloxy)Phenylsulfonyl)-8-azaspiro[4.5]decane-3-carboxamide A solution of intermediate I-29a (40 mg, 0.053 mmol) in HCl/dioxane (15 mL, 1 N) was stirred at r.t for 4 h, then concentrated to give the crude product which was purified by prep-HPLC (General procedure, Method 1) to obtained pure compound 1-128 (11.2 mg, 37%) as a yellow solid. ESI-MS (M+1): 577.2 calc. for $C_{24}H_{24}ClF_3N_2O_7S$. Rt is 2.96.

Following the same synthetic route 3c, and using the same reagents as for compound 1-128 unless otherwise indicated in the table below, the following compounds were obtained:

| Example | $R_t$ | $[M + 1]^+$ | LC-MS Method | Starting materials |
|---|---|---|---|---|
| 1-129 | 2.60 | 523.2 | 1 | 4-methoxybenzoyl chloride (R-09) |

Synthesized compounds are obtained as racemic mixtures. Corresponding isomers are purified by supercritical fluid chromatography (SFC) to obtain two enantiomers from each racemic compound.

Procedure for Supercritical Fluid Chromatography (SFC):
Details about the preparative SFC separation methods utilized are as follows:
Method 1:
  Instrument: Thar SFC Pre-80
  Column: ChiralPak AD-H, 250×30 mmI.D.
  Mobile phase: A for $CO_2$ and B for Ethanol (0.1% $NH_3.H_2O$)
  Gradient: B 50%
  Flow rate: 60 mL/min
  Back pressure: 100 bar
  Column temperature: 40° C.
  Wavelength: 220 nm
  Cycletime: ~20 min
  Sample preparation: Compound was dissolved in ethanol to ~12 mg/mL Injection: 2.0 mL per injection.
Method 2:
  Instrument: Mg II preparative SFC
  Column: ChiralPak AD-H, 250×30 mmI.D.
  Mobile phase: A for $CO_2$ and B for Methanol (0.1% $NH_3*H_2O$)
  Gradient: B 50%
  Flow rate: 40 mL/min
  Back pressure: 100 bar
  Column temperature: 38° C.
  Wavelength: 220 nm
  Cycletime: ~20 min
  Sample preparation: Compound was dissolved in methanol to ~13 mg/ml
  Injection: 3.5 mL per injection.
Method 3:
  Instrument: Mg II preparative SFC
  Column: ChiralPak AD-H, 250×30 mmI.D.
  Mobile phase: A for $CO_2$ and B for IPA (0.1% $NH_3*H_2O$)
  Gradient: B 35%
  Flow rate: 55 ml/min
  Back pressure: 100 bar
  Column temperature: 38° C.
  Wavelength: 254 nm
  Cycletime: ~8 min
  Sample preparation: Compound was dissolved in methanol to ~5 mg/mL
  Injection: 1.0 mL per injection.

After separation, the fractions were dried off via rotary evaporator at bath temperature 40° C. to get the desired isomers. Then, after concentration, enantiomeric excess (e.e.) for both enantiomers were tested under the analytical separation methods described below:

Method 1:
  Instrument: SHIMADZU-20A UFLC
  Column: ChiralPak AD-3, 100×4.6 mm
  Mobile phase: A for Hexane (0.1% IPAm) and B for Ethanol (0.05% IPAm)
  Gradient: B 40%
  Flow rate: 1.0 mL/min
  Column temperature: 30° C.
  Wavelength: 220 nm
Method 2:
  Instrument: Thar analytical SFC
  Column: ChiralPak AD-H, 250×4.6 mm
  Mobile phase: A for $CO_2$ and B for Methanol (0.05% DEA)
  Gradient: B 50%
  Flow rate: 2.0 mL/min
  Back pressure: 100 bar
  Column temperature: 35° C.
  Wavelength: 220 nm
Method 3:
  Instrument: Thar analytical SFC
  Column: ChiralPak AD-H, 250×4.6 mm
  Mobile phase: A for $CO_2$ and B for IPA (0.1% Ethanolamine)
  Gradient: B 30%
  Flow rate: 2.4 mL/min
  Back pressure: 100 bar
  Column temperature: 35° C.
  Wavelength: 220 nm After concentration, as previously reported, LC-MS was used to test the purity for both enantiomers. Then, optical rotation was measured at 20° C. using the Autopol V polarimeter.

The following isomers were obtained after chiral separation:

| Starting material | Example | $R_t$ (SFC) | SFC Method | e.e. by chiral HPLC (%) | Chiral HPLC Method | Optical Rotation $[\alpha]_D$ |
|---|---|---|---|---|---|---|
| 1-107 | 1-131 | 2.42 | 1 | 100 | 1 | +19.59° |
| 1-107 | 1-132 | 3.15 | 1 | 95.3 | 1 | −19.71° |
| 1-08 | 1-133 | 2.98 | 2 | 100 | 2 | +16.66° |
| 1-08 | 1-134 | 5.88 | 2 | 100 | 2 | −17.10° |
| 1-55 | 1-135 | 4.44 | 1 | 100 | 1 | — |
| 1-55 | 1-136 | 6.08 | 1 | 97.9 | 1 | — |
| 1-79 | 1-137 | 5.85 | 3 | 96.1 | 3 | — |
| 1-79 | 1-138 | 7.63 | 3 | 97.7 | 3 | — |

Antifibrinolytic Effect on Whole Blood Clot Formation and Lysis

Thromboelastometry is a viscoelastometric method for haemostasis testing in whole blood. TEM® measures the interactions of coagulation factors, inhibitors and cellular components during the phases of clotting and subsequent lysis over time. The rheological conditions of this method mimic the sluggish flow of blood in veins.

Detection Method:

Blood samples were obtained between 8-9 a.m. from healthy volunteers and mice in tubes containing citrate solution (0.129 M sodium citrate, Vacutainer BD) and ROTEM tests were performed following the technical details of the ROTEM® analyser (Pentapharm GmbH, Munich, Germany). A modification of in-tem test as described below was used for the examination of antifibrinolytic effects of tested compounds and its interaction with platelets in citrated blood. Kits: START-TEM assay as a recalcification reagent (ref#503-01) and IN-TEM assay for activation of intrinsic coagulation pathway (ref #503-02).

Procedure:

In a pre-warmed cuvette and holder 1 μL of Tissue plasminogen activator (tPA) (150,000 U/mL, Actylise), 20 μL of start-tem reagent ($CaCl_2$), 20 μL of in-tem reagent (activators of coagulation system), 3 μL of DMSO (control) or tested compounds (CMs) in DMSO and 300 μL of citrated blood pre-warmed were pipetted. The cup holder containing the sample mixture was placed immediately on the appropriate channel. The measurement was recorded for 60 min to allow clot formation and lysis.

Table 3 shows the results in human blood as effective concentration to delay lysis time by 50% ($EC_{50LT}$); where, $EC_{50LT} \geq 25$ μM (+), 10 μM≤$EC_{50LT}$<25 μM (++), 1 μM≤$EC_{50\ LT}$<10 μM (+++), $EC_{50\ LT}$<1 μM (++++) at all the assayed concentrations (1000-0.2 μM).

TABLE 3

| Example | $EC_{50LT}$ | Example | $EC_{50LT}$ |
|---|---|---|---|
| TXA | +++ | 1-58 | ++++ |
| 1-01 | ++++ | 1-59 | + |
| 1-02 | ++ | 1-60 | + |
| 1-03 | ++++ | 1-21 | ++++ |
| 1-04 | ++++ | 1-41 | + |
| 1-05 | ++ | 1-43 | ++++ |
| 1-06 | + | 1-54 | +++ |
| 1-07 | ++++ | 1-55 | ++++ |
| 1-08 | ++++ | 1-56 | ++++ |
| 1-09 | ++++ | 1-61 | + |
| 1-10 | ++++ | 1-62 | ++++ |
| 1-11 | ++++ | 1-63 | +++ |
| 1-12 | ++ | 1-64 | + |

TABLE 3-continued

| Example | EC$_{50LT}$ | Example | EC$_{50LT}$ |
|---|---|---|---|
| 1-13 | ++++ | 1-65 | +++ |
| 1-14 | ++++ | 1-66 | + |
| 1-15 | + | 1-67 | ++++ |
| 1-16 | +++ | 1-68 | +++ |
| 1-17 | +++ | 1-69 | +++ |
| 1-18 | +++ | 1-70 | ++++ |
| 1-19 | ++++ | 1-71 | +++ |
| 1-20 | ++++ | 1-72 | +++ |
| 1-22 | +++ | 1-73 | ++++ |
| 1-26 | ++++ | 1-74 | +++ |
| 1-28 | +++ | 1-75 | +++ |
| 1-29 | +++ | 1-76 | + |
| 1-30 | ++++ | 1-77 | +++ |
| 1-31 | ++++ | 1-78 | + |
| 1-32 | +++ | 1-79 | ++++ |
| 1-33 | + | 1-80 | ++++ |
| 1-34 | + | 1-81 | ++++ |
| 1-35 | +++ | 1-82 | ++++ |
| 1-36 | +++ | 1-83 | + |
| 1-37 | + | 1-84 | ++++ |
| 1-39 | + | 1-85 | +++ |
| 1-86 | ++++ | 1-113 | ++++ |
| 1-87 | +++ | 1-114 | ++ |
| 1-88 | ++++ | 1-115 | ++++ |
| 1-89 | + | 1-116 | ++++ |
| 1-90 | + | 1-117 | ++++ |
| 1-91 | + | 1-118 | ++++ |
| 1-92 | +++ | 1-119 | ++++ |
| 1-93 | + | 1-120 | + |
| 1-94 | + | 1-121 | +++ |
| 1-95 | + | 1-122 | + |
| 1-96 | ++++ | 1-123 | ++++ |
| 1-97 | +++ | 1-124 | +++ |
| 1-98 | + | 1-125 | ++++ |
| 1-99 | ++++ | 1-126 | + |
| 1-100 | ++++ | 1-127 | ++++ |
| 1-101 | +++ | 1-128 | + |
| 1-102 | + | 1-129 | +++ |
| 1-103 | ++++ | 1-130 | +++ |
| 1-104 | ++++ | 1-131 | ++++ |
| 1-105 | + | 1-132 | ++++ |
| 1-106 | ++++ | 1-133 | ++++ |
| 1-107 | ++++ | 1-134 | ++++ |
| 1-108 | ++++ | 1-135 | ++++ |
| 1-109 | + | 1-136 | ++++ |
| 1-110 | ++++ | 1-137 | ++++ |
| 1-111 | + | 1-138 | ++++ |
| 1-112 | ++++ | | |

Table 4 shows the results in mice blood as effective concentration to delay lysis time by 50% (EC$_{50LT}$); where, EC$_{50LT}$≥10 µM (+), 1 µM≤EC$_{50LT}$<10 µM (++), 1 nM≤EC$_{50LT}$<1 µM (+++) and EC$_{50LT}$<1 nM (++++) for all the assayed concentrations (1000-0.2 µM).

TABLE 4

| Example | EC$_{50LT}$ |
|---|---|
| TXA | +++ |
| 1-03 | ++++ |
| 1-07 | ++++ |
| 1-08 | +++ |
| 1-14 | +++ |
| 1-62 | ++++ |
| 1-73 | ++ |

As observed in the tables above (Tables 3 and 4), compounds of the invention show significant delay in the lysis time, in most cases higher than TXA.

Antifibrinolytic Effect In Vivo (Tail Bleeding Assay)

Bleeding time was evaluated in 2 months old wild-type C57Bl6 (n=10) mice by removing the tail tip. Mice (20-25 g) were anaesthetized with 2.5% isoflurane and maintained at 37° C. on heating pads. The hemostatic efficacy was evaluated in 2 models, traditional bleeding model and hyperfibrinolytic bleeding model.

Traditional bleeding model consisted in intraperitoneal injection of different compounds (4 mg/mouse, 160 mg/Kg) dissolved in 2% carboxymethyl cellulose or vehicle. Thirty minutes after injection, 5 mm of tail tip were removed using a scalpel blade and the tail tip bathed in 1 mL of sterile saline at 37° C. The time to cessation of bleeding was measured up to 30 min. The time of bleeding was defined as the interval between initial transection and the visual cessation of bleeding. The results are shown in Table 5.

TABLE 5

| | n = 10 Vehicle | n = 10 1-01 | n = 10 1-02 |
|---|---|---|---|
| Bleeding time (s) | 66.6 ± 19.4 | 31.0 ± 3.6* | 39.2 ± 4.7 |

*p < 0.05 vs vehicle

Hyperfibrinolytic bleeding model, consisted in injection of 0.5 mg/kg tPA into the ocular plexus to prolong bleeding time due to excessive fibrinolysis. First, the femoral vein was exposed and cannulated with a saline-filled polyurethane catheter (Microcannula 72-9030, Harvard Apparatus) for agents administration. The catheter was connected to a syringe pump (AL-1000, WPI) for the infusion of 200 µL (10% bolus, 90% perfusion during 40 minutes) of tested agents. Then, tPA (0.5 mg/kg) was injected into the ocular plexus and five minutes after tPA administration, saline or the different compounds was infused through the femoral catheter to ensure systemic distribution of all the agents. Reference compounds, TXA and Aprotinin, were administered at 300 and 10 mg/Kg respectively; however, all compounds of the invention were administered at 1 mg/Kg. Five minutes later, 5 mm of tail tip were removed using a scalpel blade and the tail tip bathed in 1 mL of sterile saline at 37° C.

The time of bleeding was defined as the interval between initial transections and the visual cessation of bleeding, that was measured up to 30 minutes. A value of 30 min was assigned to those animals bleeding longer than the observation period. Table 6 shows the results reporting bleeding time (BT); where BT≥20 minutes (+), 10 minutes≤BT<20 minutes (++), 5 minutes≤BT<10 minutes (+++) and BT<5 minutes (++++). Bleeding time was determined in wild type mice (C57/Bl6), where n≥10 per assayed compound; therefore, BT is reported as a mean value—in the case of saline, BT is reported as mean±ESM.

TABLE 6

| Example | BT |
|---|---|
| Saline | 28.9 ± 0.7 |
| TXA | ++** |
| Aprotinin | ++** |
| 1-03*** | +++**† |
| 1-07 | ++* |
| 1-08 | ++++**†† |
| 1-14 | ++++**†† |
| 1-20 | ++* |
| 1-26 | ++* |
| 1-55 | ++++**†† |
| 1-62 | +++**† |
| 1-73 | ++++**†† |
| 1-79 | ++** |
| 1-80 | +++**† |
| 1-82 | +++** |

TABLE 6-continued

| Example | BT |
|---|---|
| 1-96 | +++** |
| 1-99 | ++++**†† |
| 1-102 | ++* |
| 1-107 | +++** |
| 1-108 | ++++**†† |
| 1-112 | +++** |
| 1-113 | +++** |

*p < 0.05;
**p < 0.01 vs saline;
***compound administered at 10 mg/Kg;
†p < 0.05;
††p < 0.01 vs TXA As shown table 6, tested compounds of the invention show a very significant reduction of the bleeding time when compared to the control or TXA. In all the cases the dose of tested compounds were lower than TXA or Aprotinin doses.

REFERENCES CITED IN THE APPLICATION

Green and P. G. M. Wuts, Protective Groups in Organic Chemistry, Wiley, 3rd ed. 1999, Chapter 2, pp. 17-200 and Chapter 5, pp. 369-451.

D. Bouyssi et al., "Rearrangement of oxaspiroheptanes to cyclohexanones mediated by lithium iodide", *Synlett* 2000, vol. 5, pp. 749-751.

Osamu Kitagawa et al., "Stereoselective Iodine Atom Transfer [3+2] Cycloaddition Reaction with Alkenes Using Unsymmetrical Allylated Active Methine Radicals", *The Journal of Organic Chemistry* 2004, vol. 69, pp. 2607-2610.

The invention claimed is:

1. A compound of formula (I), or a pharmaceutically or veterinary acceptable salt thereof, or any stereoisomer either of the compound of formula (I) or of its pharmaceutically or veterinary acceptable salt

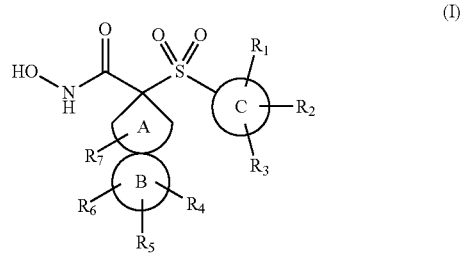

(I)

wherein A and B form a spirocyclic ring system selected from the group consisting of:

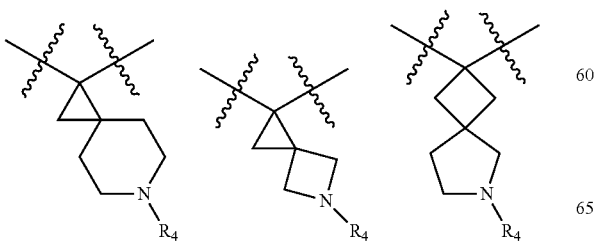

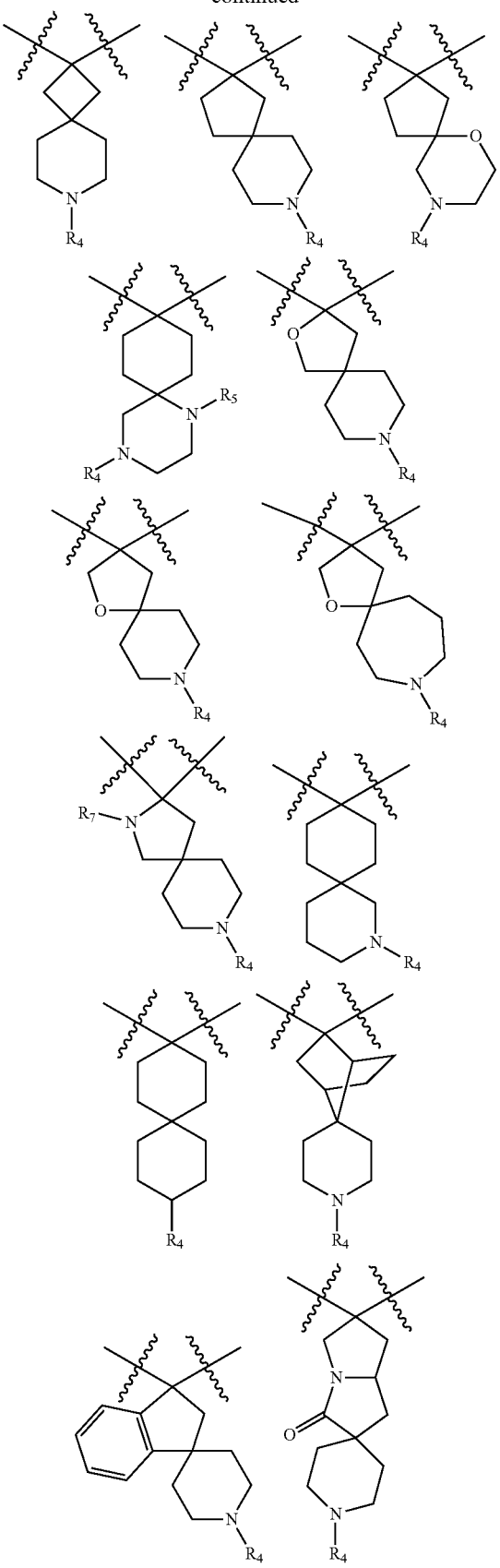

C is phenyl;

$R_1$-$R_3$ are independently selected from H, halogen, —$NO_2$, —CN, $R^a$, —$OR^{a'}$, —$OC(Y)R^{a'}$, —$OC(Y)OR^{a'}$, —$OC(Y)NR^bR^{a'}$, —$OSO_2OR^{a'}$, —$NR^bR^{a'}$, —$NR^bC(Y)R^{a'}$, —$NR^bC(Y)OR^{a'}$, —$NR^bC(Y)NR^bR^{a'}$, —$NR^bS(O)_2R^{a'}$, —$NR^bSO_2NR^bR^{a'}$, —$SR^{a'}$, —$S(O)R^{a'}$, —$S(O)OR^{a'}$, —$SO_2R^{a'}$, —$SO_2(OR^{a'})$, —$SO_2NR^bR^{a'}$, —$SC(Y)NR^bR^{a'}$, —$C(Y)R^{a'}$, —$C(Y)OR^{a'}$, —$C(Y)NR^bR^{a'}$, —$C(Y)NR^bOR^{a'}$, and —$C(O)NR^bSO_2R^{a'}$;

$R_4$—$R_5$ are independently selected from halogen, —$NO_2$, —CN, $R^c$, —$OR^c$, —$NR^dR^c$, —$NR^dC(Y)R^c$, —$NR^dC(Y)OR^c$, —$NR^dC(Y)NR^dR^c$, —$NR^dS(O)_2R^c$, —$NR^dSO_2NR^dR^c$, —$SR^c$, —$S(O)R^c$, —$S(O)OR^c$, —$SO_2R^c$, —$SO_2R(OR^c)$, —$SO_2NR^dR^c$, —$SC(Y)NR^dR^c$, —$C(Y)R^c$, —$C(Y)OR^c$, —$C(Y)NR^dR^c$, —$C(Y)NR^dOR^c$, and —$C(O)NR^dSO_2R^c$;

$R^a$ is a saturated or unsaturated ($C_1$-$C_{12}$)alkyl optionally substituted with one or more substituents $R^e$ and/or one $Cy^1$; or alternatively $R^a$ is $Cy^2$;

wherein $Cy^1$ and $Cy^2$ are independently optionally substituted with one or more substituents selected from $R^e$ and saturated or unsaturated ($C_1$-$C_6$) alkyl optionally substituted with one or more substituents $R^e$;

each $R^{a'}$ and $R^b$ are independently H or $R^a$;

$R^c$ and each $R^d$ are independently selected from H, $Cy^4$, and saturated or unsaturated ($C_1$-$C_6$)alkyl optionally substituted with one or more substituents $R^h$ and/or one $Cy^5$;

wherein $Cy^5$ is optionally substituted with one or more substituents independently selected from $R^h$ and saturated or unsaturated ($C_1$-$C_6$)alkyl optionally substituted with one or more substituents $R^h$; and wherein $Cy^5$ is optionally substituted with one or more substituents independently selected from $R^h$ and saturated or unsaturated ($C_1$-$C_6$) alkyl optionally substituted with one or more substituents $R^h$;

each $R^e$ is independently selected from halogen, —$NO_2$, —CN, —$OR^f$, —$OC(Y)R^f$, —$OC(Y)OR^f$, —$OC(Y)NR^gR^f$, —$NR^gR^f$, —$NR^gC(Y)R^f$, —$NR^gC(Y)OR^f$, —$NR^gC(Y)NR^gR^f$, —$NR^gS(O)_2R^f$, —$NR^gSO_2NR^gR^f$, —$SR^f$, —$S(O)R^f$, —$S(O)OR^f$, —$SO_2R^f$, —$SO_2(OR^f)$, —$SO_2NR^gR^f$, —$SC(Y)NR^gR^f$, —$C(Y)R^f$, —$C(Y)OR^f$, —$C(Y)NR^gR^f$, —$C(Y)NR^gOR^f$ and —$C(O)NR^gSO_2R^f$;

$R^f$ and each $R^g$ are independently selected from H, $Cy^6$, and saturated or unsaturated ($C_1$-$C_6$)alkyl optionally substituted with one or more substituents $R^h$ and/or one $Cy^7$;

wherein $Cy^6$ any $Cy^7$ are optionally substituted with one or more substituents independently selected from $R^h$ and ($C_1$-$C_4$)alkyl optionally substituted with one or more substituents $R^h$;

each $R^h$ is independently selected from halogen, —$NO_2$, —CN, —$OR^i$, —$OC(O)R^i$, —$OC(O)OR^i$, —$OC(O)NR^iR^i$, —$NR^iC(O)R^i$, —$NR^iC(O)OR^i$, —$NR^iC(O)NR^iR^i$, —$NR^iS(O)_2R^i$, —$NR^iSO_2NR^iR^i$, —$SR^i$, —$S(O)R^i$, —$SO_2R^i$, —$SO_2(OR^i)$, —$SO_2NR^iR^i$, —$C(O)R^i$, —$C(O)OR^i$, —$C(O)NR^iR^i$, and —$C(O)NR^iOR^i$;

each $R^i$ is independently H or —($C_1$-$C_4$)alkyl optionally substituted with one or more halogen atoms;

Y is O, S, or $NR^g$;

$Cy^1$, $Cy^2$, $Cy^4$ and $Cy^6$ are independently a C or N-attached known ring system selected from 3- to 8-membered carbocyclic or heterocyclic monocyclic ring, saturated or partially unsaturated; phenyl; 5- or 6-membered heteroaromatic ring; and 6- to 18-membered carbocyclic or heterocyclic polycyclic ring system, saturated, partially unsaturated, aromatic or partially aromatic;

$Cy^3$, $Cy^5$ and $Cy^7$ are independently a C or N-attached known ring system selected from 3- to 8-membered carbocyclic or heterocyclic monocyclic ring, saturated or partially unsaturated; phenyl; and 5- or 6-membered heteroaromatic ring;

wherein in the carbocyclic rings all ring members are carbon atoms; and in the heterocyclic and heteroaromatic rings one or more ring members are selected from N, O and S; and wherein in all saturated or partially unsaturated rings one or two members of the rings are optionally C(O) and/or C(NH) and/or C[N($C_1$-$C_4$)alkyl].

2. The compound of formula (I) according to claim 1, wherein in $R_1$-$R_3$, $R^f$ and each $R^g$ are independently selected from H and saturated or unsaturated ($C_1$-$C_6$)alkyl optionally substituted with one or more fluorine atoms.

3. The compound of formula (I) according to claim 1, wherein $R_1$-$R_3$ are independently selected from H, halogen, —$NO_2$, —CN, $R^a$, —$OR^{a'}$, —$OC(O)R^{a'}$, —$OC(O)OR^{a'}$, —$OC(O)NR^bR^{a'}$, —$NR^bR^{a'}$, —$NR^bC(O)R^{a'}$, —$NR^bC(O)OR^{a'}$, —$NR^bC(O)NR^bR^{a'}$, —$NR^bS(O)_2R^{a'}$, —$SR^{a'}$, —$S(O)R^{a'}$, —$SO_2R^{a'}$, —$SO_2NR^bR^{a'}$, —$C(O)R^{a'}$, —$C(O)OR^{a'}$, —$C(O)NR^bR^{a'}$, and —$C(O)NR^bOR^{a'}$.

4. The compound of formula (I) according to claim 1, wherein $R_4$-$R_7$ are independently selected from halogen, —$NO_2$, —CN, $R^c$, —$OR^c$, —$NR^dR^c$, —$NR^dC(O)R^c$, —$NR^dC(O)OR^c$, —$NR^dC(O)NR^dR^c$, —$NR^dS(O)_2R^c$, —$S(O)R^c$, —$SO_2R^c$, —$SO_2NR^dR^c$, —$C(O)R^c$, —$C(O)OR^c$, and —$C(O)NR^dR^c$.

5. The compound of formula (I) according to claim 1, wherein $R_2$ and $R_3$ are independently selected from H, halogen, $R^a$, —$OR^{a'}$, and —$NR^bR^{a'}$; and $R_5$-$R_7$ are independently selected from H, halogen, $R^c$, —$OR^c$, and —$NR^dR^c$, wherein $R^a$, $R^{a'}$, $R^b$, $R^c$ and $R^d$ are independently selected from H and —($C_1$-$C_4$)alkyl optionally substituted with one or more fluorine atoms.

6. A pharmaceutical or veterinary composition which comprises an effective amount of a compound of formula (I) as defined in claim 1, or a pharmaceutically or veterinary acceptable salt thereof, or any stereoisomer either of the compound of formula (I) or of its pharmaceutically or veterinary acceptable salt, together with one or more pharmaceutically or veterinary acceptable excipients or carriers.

7. A method for antiftifibrinolytic and antihemorrhagic treatment comprising administering an effective amount of a compound of formula (I) as defined in claim 1, or a pharmaceutically or veterinary acceptable salt thereof, or any stereoisomer either of the compound of formula (I) or of its pharmaceutically or veterinary acceptable salt, and one or more pharmaceutically or veterinary acceptable excipients or carriers, in a subject in need thereof.

8. A compound of formula (III)

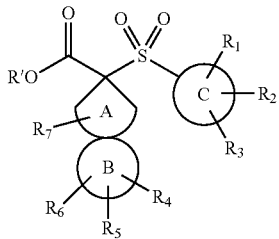

wherein A, B, C, $R_1$-$R_7$ are as defined in claim 1, and R' is H or a carboxy protective group selected from the group consisting of $(C_1$-$C_6)$alkyl, benzyl, p-methoxyphenyl, trimethylsilyl and [2-(Trimethylsilyl)ethoxy]methyl (SEM), with the proviso that compound (III) is other than 7-methoxycarbonyl-7-phenylsulphonyl-2-oxaspiro[2.4]heptane and (2S*,4R*)-2-Phenylsulfonyl-4-iodomethyl-6,11-dioxaspiro[4.6]undecane-2-carboxylic Acid Methyl Ester; or a compound of formula (II)

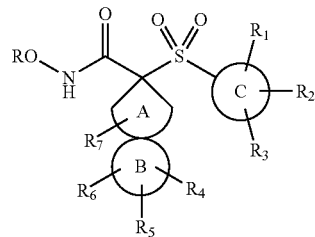

wherein A, B, C, $R_1$-$R_7$ are as defined in claim 1, and R is an hydroxamic acid protective group selected from the group consisting of tetrahydro-2H-pyran-2-yloxy (THP), benzyl, 1-naphthylmethyl and dimethyloxybenzyl (DMB).

* * * * *